(12) United States Patent
Patel et al.

(10) Patent No.: US 11,957,376 B2
(45) Date of Patent: *Apr. 16, 2024

(54) ATHERECTOMY CATHETER WITH SERRATED CUTTER

(71) Applicant: Avinger, Inc., Redwood City, CA (US)

(72) Inventors: Himanshu N. Patel, San Jose, CA (US); Richard R. Newhauser, Redwood City, CA (US); Anthony J. Fernandez, San Mateo, CA (US); Vincent Yeh, Redwood City, CA (US)

(73) Assignee: Avinger, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/816,673

(22) Filed: Aug. 1, 2022

(65) Prior Publication Data
US 2023/0157718 A1 May 25, 2023

Related U.S. Application Data

(63) Continuation of application No. 16/148,246, filed on Oct. 1, 2018, now Pat. No. 11,399,863, which is a
(Continued)

(51) Int. Cl.
*A61B 17/3207* (2006.01)
*A61B 5/00* (2006.01)
(Continued)

(52) U.S. Cl.
CPC .... *A61B 17/320758* (2013.01); *A61B 5/0066* (2013.01); *A61B 5/0084* (2013.01);
(Continued)

(58) Field of Classification Search
CPC .... A61B 17/320758; A61B 17/320783; A61B 2017/00477; A61B 2017/22052;
(Continued)

(56) References Cited

U.S. PATENT DOCUMENTS 3,367,727 A 2/1968 Ward et al.
3,908,637 A 9/1975 Doroshow
(Continued)

FOREIGN PATENT DOCUMENTS

CN 1875242 A 12/2006
CN 1947652 A 4/2007
(Continued)

OTHER PUBLICATIONS

Rosenthal et al.; U.S. Appl. No. 18/337,852 entitled "Atherectomy catheter with laterally-displaceable tip," filed Jun. 20, 2023.
(Continued)

*Primary Examiner* — Ashley L Fishback
(74) *Attorney, Agent, or Firm* — Shay Glenn LLP

(57) ABSTRACT

An atherectomy catheter device includes an elongate body, a drive shaft extending proximally to distally within the elongate body, and a cutter attached to the drive shaft. The cutter includes a serrated annular cutting edge formed on a distal edge of the cutter and a recessed bowl extending radially inwards from the annular cutting edge to a center of the cutter. The recessed bowl has a first curvature. The cutter further includes a plurality of grinding segments extending inwardly from the distal edge within the bowl. Each of the plurality of segments has a second curvature that is different from the first curvature.

20 Claims, 55 Drawing Sheets

Related U.S. Application Data continuation-in-part of application No. PCT/US2017/025555, filed on Mar. 31, 2017.

(60) Provisional application No. 62/317,214, filed on Apr. 1, 2016, provisional application No. 62/317,231, filed on Apr. 1, 2016.

(51) Int. Cl.

| | | |
|---|---|---|
| *A61B 17/00* | (2006.01) | |
| *A61B 17/22* | (2006.01) | |
| *A61B 17/32* | (2006.01) | |
| *A61B 90/50* | (2016.01) | |
| *A61B 90/00* | (2016.01) | |
| *A61B 90/57* | (2016.01) | |

(52) U.S. Cl.
CPC ...... *A61B 17/320783* (2013.01); *A61B 90/50* (2016.02); *A61B 2017/00477* (2013.01); *A61B 2017/22052* (2013.01); *A61B 2017/22055* (2013.01); *A61B 2017/22067* (2013.01); *A61B 2017/22071* (2013.01); *A61B 2017/22079* (2013.01); *A61B 2017/320004* (2013.01); *A61B 2017/320791* (2013.01); *A61B 2090/3735* (2016.02); *A61B 2090/571* (2016.02); *A61B 2217/007* (2013.01)

(58) Field of Classification Search
CPC ........... A61B 2017/22067; A61B 2017/22071; A61B 2017/22079; A61B 2017/320004; A61B 2017/320775; A61B 2017/320791
See application file for complete search history.

(56) References Cited

U.S. PATENT DOCUMENTS

| | | | |
|---|---|---|---|
| 4,178,935 A | 12/1979 | Gekhaman et al. | |
| 4,487,206 A | 12/1984 | Aagard | |
| 4,527,553 A | 7/1985 | Upsher | |
| 4,552,554 A | 11/1985 | Gould et al. | |
| 4,578,061 A | 3/1986 | Lemelson | |
| 4,598,710 A | 7/1986 | Kleinberg et al. | |
| 4,611,600 A | 9/1986 | Cohen | |
| 4,621,353 A | 11/1986 | Hazel et al. | |
| 4,639,091 A | 1/1987 | Huignard et al. | |
| 4,651,753 A | 3/1987 | Lifton | |
| 4,654,024 A | 3/1987 | Crittenden et al. | |
| 4,681,106 A | 7/1987 | Kensey et al. | |
| 4,686,982 A | 8/1987 | Nash | |
| 4,691,708 A | 9/1987 | Kane | |
| 4,729,763 A | 3/1988 | Henrie | |
| 4,771,774 A | 9/1988 | Simpson et al. | |
| 4,781,186 A | 11/1988 | Simpson et al. | |
| 4,808,163 A | 2/1989 | Laub | |
| 4,841,977 A | 6/1989 | Griffith et al. | |
| 4,842,578 A | 6/1989 | Johnson et al. | |
| 4,850,354 A | 7/1989 | McGurk-Burleson et al. | |
| 4,857,046 A | 8/1989 | Stevens et al. | |
| 4,920,961 A | 5/1990 | Grossi et al. | |
| 4,926,858 A | 5/1990 | Gifford, III et al. | |
| 5,000,185 A | 3/1991 | Yock | |
| 5,002,560 A | 3/1991 | Machold et al. | |
| 5,018,529 A | 5/1991 | Tenerz et al. | |
| 5,041,082 A | 8/1991 | Shiber | |
| 5,047,040 A | 9/1991 | Simpson et al. | |
| 5,085,662 A | 2/1992 | Willard | |
| 5,099,850 A | 3/1992 | Matsui et al. | |
| 5,178,153 A | 1/1993 | Einzig | |
| 5,182,291 A | 1/1993 | Gubin et al. | |
| 5,190,050 A | 3/1993 | Nitzsche | |
| 5,192,291 A | 3/1993 | Pannek, Jr. | |
| 5,217,479 A | 6/1993 | Shuler | |
| 5,312,415 A | 5/1994 | Palermo | |
| 5,312,425 A | 5/1994 | Evans et al. | |
| 5,321,501 A | 6/1994 | Swanson et al. | |
| 5,333,142 A | 7/1994 | Scheps | |
| 5,358,472 A | 10/1994 | Vance et al. | |
| 5,366,464 A | 11/1994 | Belknap | |
| 5,372,601 A | 12/1994 | Lary | |
| 5,383,460 A | 1/1995 | Jang et al. | |
| 5,383,467 A | 1/1995 | Auer et al. | |
| 5,425,273 A | 6/1995 | Chevalier | |
| 5,425,371 A | 6/1995 | Mischenko | |
| 5,429,136 A | 7/1995 | Milo et al. | |
| 5,431,673 A | 7/1995 | Summers et al. | |
| 5,437,284 A | 8/1995 | Trimble | |
| 5,449,372 A | 9/1995 | Schmaltz et al. | |
| 5,459,570 A | 10/1995 | Swanson et al. | |
| 5,460,168 A | 10/1995 | Masubuchi et al. | |
| 5,465,147 A | 11/1995 | Swanson | |
| 5,507,725 A | 4/1996 | Savage et al. | |
| 5,507,760 A | 4/1996 | Wynne et al. | |
| 5,507,795 A | 4/1996 | Chiang et al. | |
| 5,517,998 A | 5/1996 | Madison | |
| 5,529,580 A | 6/1996 | Kusunok et al. | |
| 5,556,405 A | 9/1996 | Lary | |
| 5,607,394 A | 3/1997 | Andersen et al. | |
| 5,613,981 A | 3/1997 | Boyle et al. | |
| 5,620,426 A | 4/1997 | Braithwaite | |
| 5,632,754 A | 5/1997 | Farley et al. | |
| 5,632,755 A | 5/1997 | Nordgren et al. | |
| 5,667,490 A | 9/1997 | Keith et al. | |
| 5,674,232 A | 10/1997 | Halliburton | |
| 5,676,012 A | 10/1997 | Ceriale | |
| 5,681,336 A | 10/1997 | Clement et al. | |
| 5,690,634 A | 11/1997 | Muller et al. | |
| 5,722,403 A | 3/1998 | McGee et al. | |
| 5,728,148 A | 3/1998 | Bostrom et al. | |
| 5,749,846 A | 5/1998 | Edwards et al. | |
| 5,795,295 A | 8/1998 | Hellmuth et al. | |
| 5,807,339 A | 9/1998 | Bostrom et al. | |
| 5,830,145 A | 11/1998 | Tenhoff | |
| 5,836,957 A | 11/1998 | Schulz et al. | |
| 5,843,050 A | 12/1998 | Jones et al. | |
| 5,843,103 A | 12/1998 | Wulfman | |
| 5,851,212 A | 12/1998 | Zirps et al. | |
| 5,868,778 A | 2/1999 | Gershony et al. | |
| 5,872,879 A | 2/1999 | Hamm | |
| 5,904,651 A | 5/1999 | Swanson et al. | |
| 5,907,425 A | 5/1999 | Dickensheets et al. | |
| 5,935,075 A | 8/1999 | Casscells et al. | |
| 5,935,139 A | 8/1999 | Bates | |
| 5,938,602 A | 8/1999 | Lloyd | |
| 5,938,671 A | 8/1999 | Katoh et al. | |
| 5,951,482 A | 9/1999 | Winston et al. | |
| 5,951,581 A | 9/1999 | Saadat et al. | |
| 5,951,583 A | 9/1999 | Jensen et al. | |
| 5,956,355 A | 9/1999 | Swanson et al. | |
| 5,957,952 A | 9/1999 | Gershony et al. | |
| 5,987,995 A | 11/1999 | Sawatari et al. | |
| 5,997,558 A | 12/1999 | Nash | |
| 6,001,112 A | 12/1999 | Taylor | |
| 6,007,530 A | 12/1999 | Dornhofer et al. | |
| 6,010,449 A | 1/2000 | Selmon et al. | |
| 6,013,072 A | 1/2000 | Winston et al. | |
| 6,017,359 A | 1/2000 | Gershony et al. | |
| 6,027,514 A | 2/2000 | Stine et al. | |
| 6,032,673 A | 3/2000 | Savage et al. | |
| 6,048,349 A | 4/2000 | Winston et al. | |
| 6,080,170 A | 6/2000 | Nash et al. | |
| 6,106,515 A | 8/2000 | Winston et al. | |
| 6,110,164 A | 8/2000 | Vidlund | |
| 6,120,515 A | 9/2000 | Rogers et al. | |
| 6,120,516 A | 9/2000 | Selmon et al. | |
| 6,134,002 A | 10/2000 | Stimson et al. | |
| 6,134,003 A | 10/2000 | Tearney et al. | |
| 6,152,938 A | 11/2000 | Curry | |
| 6,152,951 A | 11/2000 | Hashimoto et al. | |
| 6,160,826 A | 12/2000 | Swanson et al. | |
| 6,175,669 B1 | 1/2001 | Colston et al. | |
| 6,176,871 B1 | 1/2001 | Pathak et al. | |
| 6,183,432 B1 | 2/2001 | Milo | |

(56) References Cited

U.S. PATENT DOCUMENTS

| | | |
|---|---|---|
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,009 B1 | 9/2002 | Dasilva et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,673,042 B1 | 1/2004 | Samson et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,776,062 B2 | 8/2010 | Bessellink et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,213,224 B2 | 2/2019 | Guggenheimer et al. |
| 10,244,934 B2 | 4/2019 | Tachibana et al. |

(56) References Cited

U.S. PATENT DOCUMENTS

| | | |
|---|---|---|
| 10,314,667 B2 | 6/2019 | Garvey et al. |
| 10,335,173 B2 | 7/2019 | Carver et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,406,316 B2 | 9/2019 | Garvey et al. |
| 10,470,795 B2 | 11/2019 | Patel et al. |
| 10,548,478 B2 | 2/2020 | Simpson et al. |
| 10,568,520 B2 | 2/2020 | Patel et al. |
| 10,568,655 B2 | 2/2020 | Simpson et al. |
| 10,722,121 B2 | 7/2020 | Smith et al. |
| 10,729,326 B2 | 8/2020 | Spencer et al. |
| 10,860,484 B2 | 12/2020 | McKenna et al. |
| 10,869,685 B2 | 12/2020 | Patel et al. |
| 10,932,670 B2 | 3/2021 | Smith et al. |
| 10,952,615 B2 | 3/2021 | Kankaria |
| 10,952,763 B2 | 3/2021 | Newhauser et al. |
| 11,033,190 B2 | 6/2021 | Patel et al. |
| 11,076,773 B2 | 8/2021 | Patel et al. |
| 11,096,717 B2 | 8/2021 | Gupta et al. |
| 11,134,849 B2 | 10/2021 | Simpson et al. |
| 11,135,019 B2 | 10/2021 | Spencer et al. |
| 11,147,583 B2 | 10/2021 | Patel et al. |
| 11,206,975 B2 | 12/2021 | Tachibana et al. |
| 11,224,459 B2 | 1/2022 | Patel et al. |
| 11,278,248 B2 | 3/2022 | Christensen |
| 11,284,839 B2 | 3/2022 | Black et al. |
| 11,284,916 B2 | 3/2022 | Patel et al. |
| 11,344,327 B2 | 5/2022 | Fernandez et al. |
| 11,382,653 B2 | 7/2022 | Patel et al. |
| 11,399,863 B2 | 8/2022 | Patel et al. |
| 11,406,412 B2 | 8/2022 | Gupta et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0138091 A1 | 9/2002 | Pflueger |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0114875 A1 | 6/2003 | Sjostrom |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0021075 A1 | 1/2005 | Bonnette et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0149096 A1 | 7/2005 | Hilal et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |

(56) References Cited

U.S. PATENT DOCUMENTS

| | | |
|---|---|---|
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2008/0287795 A1 | 11/2008 | Klingensmith et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0073455 A1 | 3/2009 | Onimura |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196477 A1 | 8/2009 | Cense |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0234220 A1 | 9/2009 | Maschke |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0268159 A1 | 10/2009 | Xu et al. |
| 2009/0275966 A1 | 11/2009 | Mitusina |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0198081 A1 | 8/2010 | Hanlin et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0137140 A1 | 6/2011 | Tearney et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0136350 A1 | 5/2012 | Goshgarian et al. |
| 2012/0203230 A1 | 8/2012 | Adams |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0023865 A1 | 1/2013 | Steinke et al. |
| 2013/0035692 A1 | 2/2013 | Sorensen et al. |
| 2013/0072787 A1 | 3/2013 | Wallace et al. |
| 2013/0184549 A1 | 7/2013 | Avitall et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler et al. |
| 2014/0222047 A1 | 8/2014 | Vreeman |
| 2014/0243881 A1 | 8/2014 | Lees et al. |
| 2014/0275996 A1 | 9/2014 | Stigall |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0146211 A1 | 5/2015 | Bhagavatula et al. |
| 2015/0320975 A1 | 11/2015 | Simpson et al. |
| 2015/0327866 A1 | 11/2015 | Eckhouse et al. |
| 2016/0144155 A1 | 5/2016 | Simpson et al. |
| 2016/0310700 A1 | 10/2016 | Drake et al. |
| 2016/0354109 A1 | 12/2016 | Guggenheimer et al. |
| 2016/0354110 A1 | 12/2016 | Guggenheimer et al. |
| 2017/0100144 A1 | 4/2017 | Zhadkevich |
| 2017/0172666 A1 | 6/2017 | Govari et al. |
| 2018/0084985 A1 | 3/2018 | Saw et al. |
| 2018/0200488 A1 | 7/2018 | Drake et al. |
| 2018/0207417 A1 | 7/2018 | Zung et al. |
| 2018/0364024 A1 | 12/2018 | Baca et al. |
| 2019/0110809 A1 | 4/2019 | Rosenthal et al. |
| 2019/0313941 A1 | 10/2019 | Radjabi |

(56) References Cited

U.S. PATENT DOCUMENTS

| | | |
|---|---|---|
| 2021/0059713 A1 | 3/2021 | Patel et al. |
| 2021/0076949 A1 | 3/2021 | Smith et al. |
| 2021/0177262 A1 | 6/2021 | Spencer et al. |
| 2021/0267621 A1 | 9/2021 | Simpson et al. |
| 2021/0330345 A1 | 10/2021 | Newhauser et al. |
| 2021/0345903 A1 | 11/2021 | Patel et al. |
| 2022/0007941 A1 | 1/2022 | Kankaria |
| 2022/0031168 A1 | 2/2022 | Patel et al. |
| 2022/0039658 A1 | 2/2022 | Smith et al. |
| 2022/0039828 A1 | 2/2022 | Patel et al. |
| 2022/0071656 A1 | 3/2022 | Patel et al. |
| 2022/0079617 A1 | 3/2022 | Gupta et al. |
| 2022/0095926 A1 | 3/2022 | Simpson et al. |
| 2022/0125525 A1 | 4/2022 | Spencer et al. |
| 2022/0168011 A1 | 6/2022 | Patel et al. |
| 2022/0183545 A1 | 6/2022 | Tachibana et al. |
| 2022/0240860 A1 | 8/2022 | Black et al. |
| 2022/0273336 A1 | 9/2022 | Fernandez et al. |
| 2022/0273337 A1 | 9/2022 | Patel et al. |
| 2022/0323099 A1 | 10/2022 | Patel et al. |
| 2022/0346638 A1 | 11/2022 | Patel |
| 2023/0225616 A1 | 7/2023 | Patel et al. |

FOREIGN PATENT DOCUMENTS

| | | | |
|---|---|---|---|
| CN | 101601581 | A | 12/2009 |
| CN | 103027727 | A | 4/2013 |
| CN | 104968285 | A | 10/2015 |
| DE | 202006018883.5 | U | 2/2007 |
| EP | 0347098 | A2 | 12/1989 |
| EP | 0808638 | A1 | 11/1997 |
| EP | 0845692 | B1 | 11/2005 |
| EP | 1859732 | A1 | 11/2007 |
| EP | 2090245 | A1 | 8/2009 |
| EP | 2353526 | B1 | 9/2013 |
| EP | 2942028 | A1 | 11/2015 |
| EP | 3446648 | A1 | 2/2019 |
| JP | S62-275425 | A | 11/1987 |
| JP | 03502060 | A | 2/1990 |
| JP | H05501065 | A | 3/1993 |
| JP | 05103763 | A | 4/1993 |
| JP | 06027343 | A | 2/1994 |
| JP | H07184888 | A | 7/1995 |
| JP | 07308393 | A | 11/1995 |
| JP | 2002214127 | A | 7/2002 |
| JP | 2004509695 | A | 4/2004 |
| JP | 2004516073 | A | 6/2004 |
| JP | 2005114473 | A | 4/2005 |
| JP | 2005230550 | A | 9/2005 |
| JP | 2005249704 | A | 9/2005 |
| JP | 2005533533 | A | 11/2005 |
| JP | 2008175698 | A | 7/2006 |
| JP | 2006288775 | A | 10/2006 |
| JP | 2006313158 | A | 11/2006 |
| JP | 2006526790 | A | 11/2006 |
| JP | 2006326157 | A | 12/2006 |
| JP | 200783053 | A | 4/2007 |
| JP | 200783057 | A | 4/2007 |
| JP | 2007225349 | A | 9/2007 |
| JP | 2007533361 | A | 11/2007 |
| JP | 2008023627 | A | 2/2008 |
| JP | 2008128708 | A | 6/2008 |
| JP | 2008145376 | A | 6/2008 |
| JP | 2008183208 | A | 8/2008 |
| JP | 2008253492 | A | 10/2008 |
| JP | 200914751 | A | 1/2009 |
| JP | 2009509690 | A | 3/2009 |
| JP | 200978150 | A | 4/2009 |
| JP | 2009066252 | A | 4/2009 |
| JP | 2009201969 | A | 9/2009 |
| JP | 2010042182 | A | 2/2010 |
| JP | 2010518900 | A | 6/2010 |
| JP | 2011521747 | A | 7/2011 |
| JP | 2012143558 | A | 8/2012 |
| JP | 2012229976 | A | 11/2012 |
| JP | 2012533353 | A | 12/2012 |
| JP | 2013512736 | A | 4/2013 |
| JP | 2013/524930 | A | 6/2013 |
| JP | 2015533584 | A | 11/2015 |
| JP | 2016508758 | A | 3/2016 |
| KR | 2007/0047221 | A | 5/2007 |
| RU | 2185859 | C2 | 7/2002 |
| RU | 2218191 | C2 | 12/2003 |
| WO | WO91/17698 | A1 | 11/1991 |
| WO | WO99/23958 | A1 | 5/1999 |
| WO | WO00/54659 | A1 | 9/2000 |
| WO | WO01/15609 | A1 | 3/2001 |
| WO | WO01/76680 | A1 | 10/2001 |
| WO | WO2006/133030 | A2 | 12/2006 |
| WO | WO2008/005888 | A2 | 1/2008 |
| WO | WO2008/029506 | A1 | 3/2008 |
| WO | WO2008/042987 | A2 | 4/2008 |
| WO | WO2008/051951 | A1 | 5/2008 |
| WO | WO2008/065600 | A2 | 6/2008 |
| WO | WO2008/086613 | A1 | 7/2008 |
| WO | WO2008/087613 | A2 | 7/2008 |
| WO | WO2008/151155 | A2 | 12/2008 |
| WO | WO2009/005779 | A1 | 1/2009 |
| WO | WO2009/006335 | A1 | 1/2009 |
| WO | WO2009/009799 | A1 | 1/2009 |
| WO | WO2009/009802 | A1 | 1/2009 |
| WO | WO2009/023635 | A1 | 2/2009 |
| WO | WO2009/024344 | A1 | 2/2009 |
| WO | WO2009/094341 | A2 | 7/2009 |
| WO | WO2009/140617 | A1 | 11/2009 |
| WO | WO2009/148317 | A1 | 12/2009 |
| WO | WO2010/039464 | A1 | 4/2010 |
| WO | WO2010/056771 | A1 | 5/2010 |
| WO | WO2011/044387 | A2 | 4/2011 |
| WO | WO2011/062087 | A1 | 5/2011 |
| WO | WO2012/057940 | A1 | 5/2012 |
| WO | WO2012/061935 | A1 | 5/2012 |
| WO | WO2012/123737 | A1 | 9/2012 |
| WO | WO2012/166332 | A1 | 12/2012 |
| WO | WO2013/033490 | A1 | 3/2013 |
| WO | WO2013/056262 | A1 | 4/2013 |
| WO | WO2014/077870 | A1 | 5/2014 |
| WO | WO2014/093148 | A2 | 6/2014 |
| WO | WO2015/074018 | A1 | 5/2015 |
| WO | WO2015/101747 | A1 | 7/2015 |
| WO | WO2015/120146 | A1 | 8/2015 |
| WO | WO2015/165736 | A1 | 11/2015 |
| WO | WO2017/007853 | A1 | 1/2017 |
| WO | WO2017/132247 | A1 | 8/2017 |
| WO | WO2017/161166 | A1 | 9/2017 |
| WO | WO2018/094041 | A1 | 5/2018 |

OTHER PUBLICATIONS

Aziz et al.; Chronic total occlusions—a stiff challenge requiring a major breakthrough: is there light at the end of the tunnel ?; Heart; vol. 91; suppl. III; pp. 42-48; Jun. 2005.

Bayer Material Science: ; Snap-Fit Joints for Plastics; 26 pages; retrieved from the Internet: ( https://web.archive.org/web/20121119232733if_/http://fab.cba.mit.edu:80/classes/S62.12/people/vernelle.noel/Plastic_Snap_fit_design.pdf) on Sep. 26, 2018.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Leitgeb et al.; Performance of fourier domain vs time domain optical coherence tomography; Optics Express; 11(8); pp. 889-894; Apr. 21, 2003.

(56) References Cited

OTHER PUBLICATIONS

Linares et al.; Arbitrary single-mode coupling by tapered and nontapered grin fiber lenses; Applied Optics; vol. 29; No. 28; pp. 4003-4007; Oct. 1, 1990.

Merriam Webster; Proximal (Definition); 10 pages; retrieved from the internet (https://www.merriam-webster.com/dictionary/proximal) on Jun. 9, 2021.

Muller et al.; Time-gated infrared fourier-domain optical coherence tomography; CFM5; San Jose, California; CLEO May 4, 2008; 2 pages.

Rollins et al.; Optimal interferometer designs for optical coherence tomography; Optics Letters; 24(21); pp. 1484-1486; Nov. 1999.

Schmitt et al.; A new rotational thrombectomy catheter: System design and first clinical experiences; Cardiovascular and Interventional Radiology; Springer-Verlag; 22(6); pp. 504-509; Nov. 1, 1999.

Sharma et al.; Common-path optical coherence tomography with side-viewing bare fiber probe for endoscopic optical coherence tomography; Rev. Sci. Instrum.; vol. 78; 113102; 5 pages; Nov. 6, 2007.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Stamper et al.; Plaque characterization with optical coherence tomography. Journal of the American College of Cardiology. 47(8); pp. 69-79; Apr. 18, 2006.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp. (011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Wikipedia; Hinge; 4 pages; retrieved from the internet (https://en.wikipedia.org/w/index.php?title=Hinge&oldid=479569345) on Jun. 9, 2021.

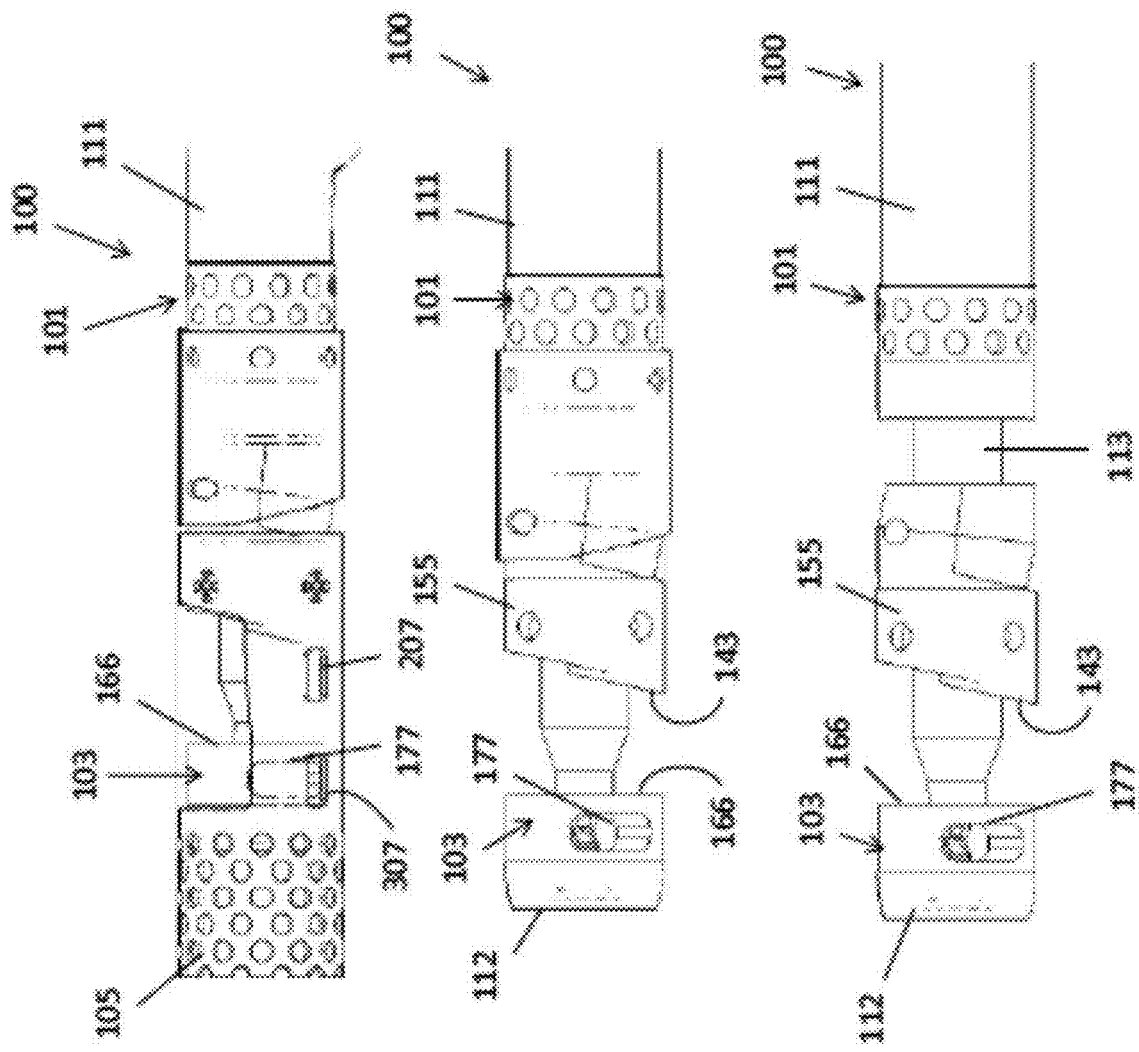

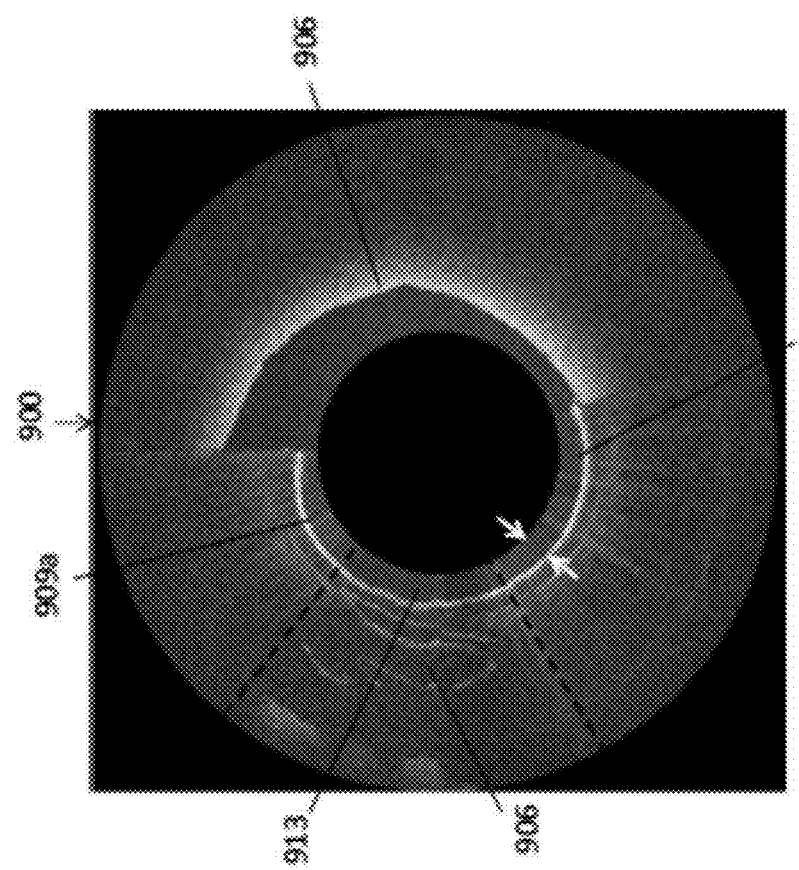
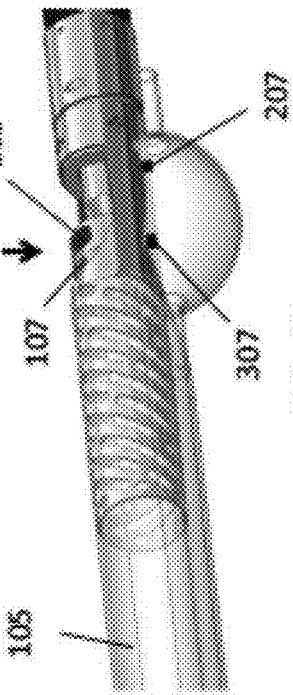
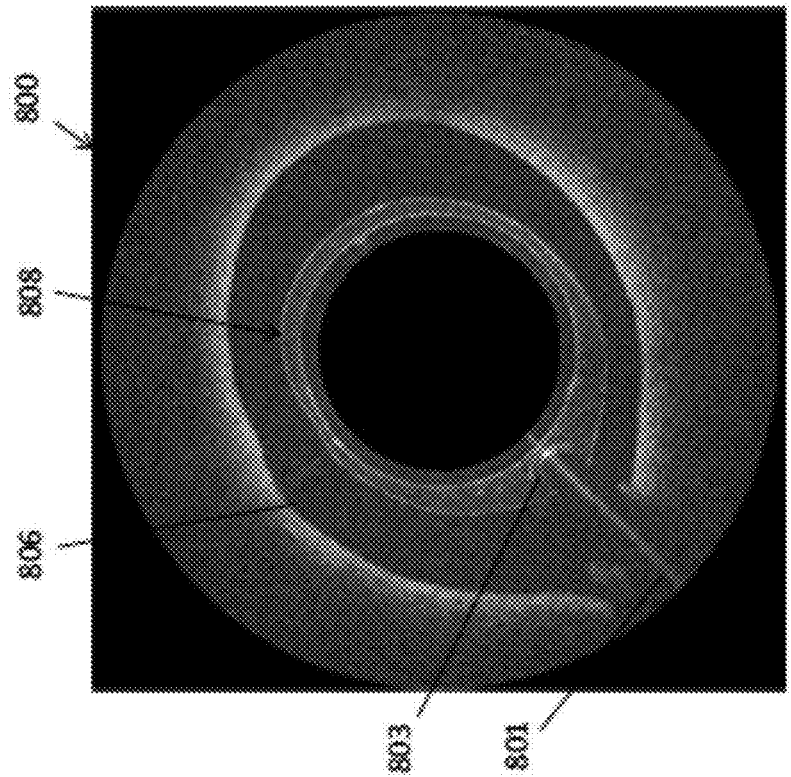
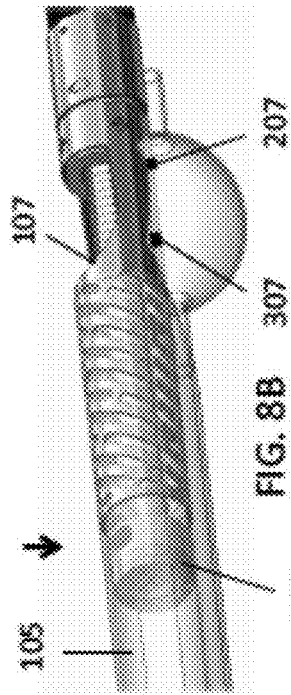
FIG. 9A
FIG. 9B
FIG. 8A
FIG. 8B

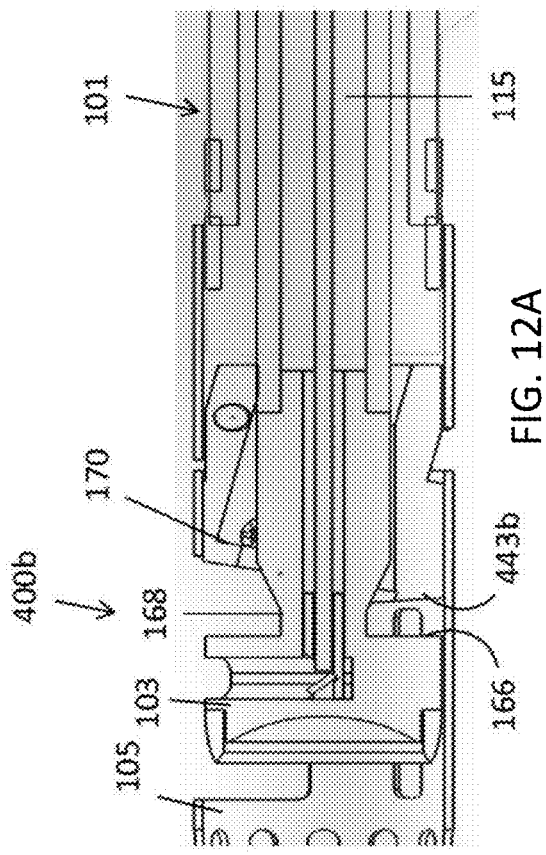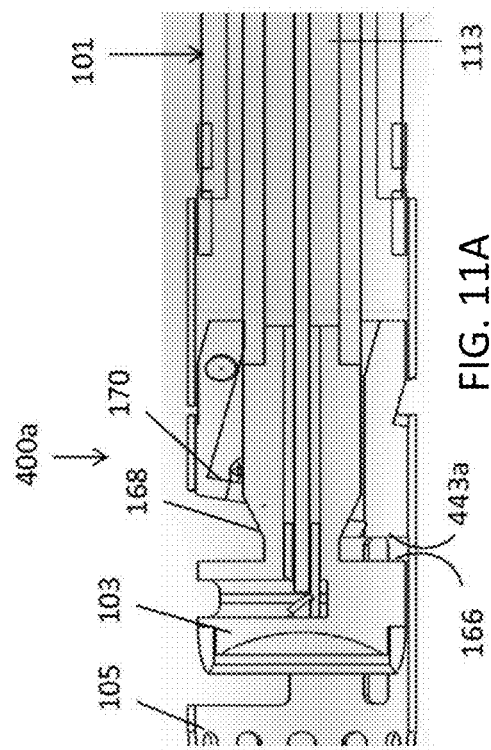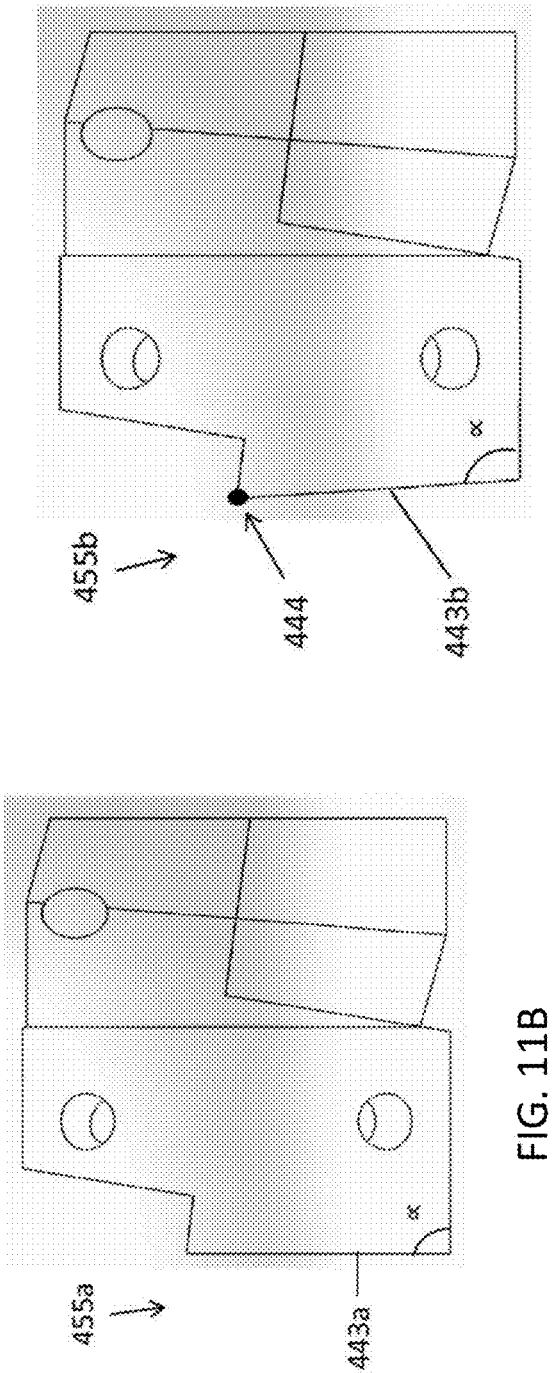

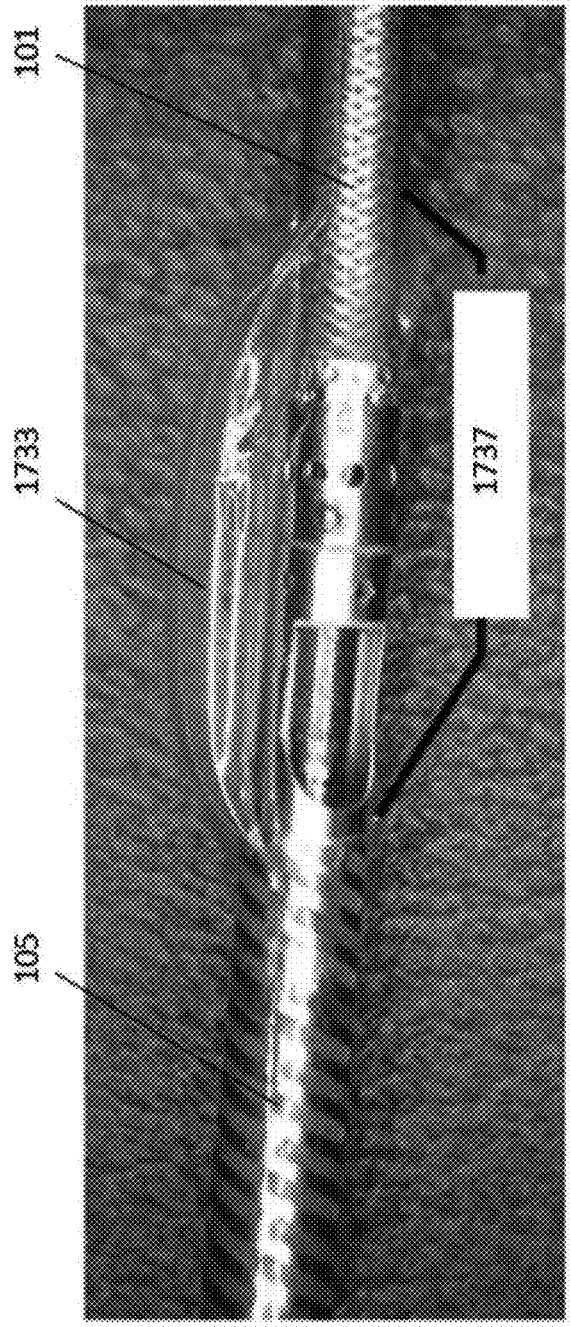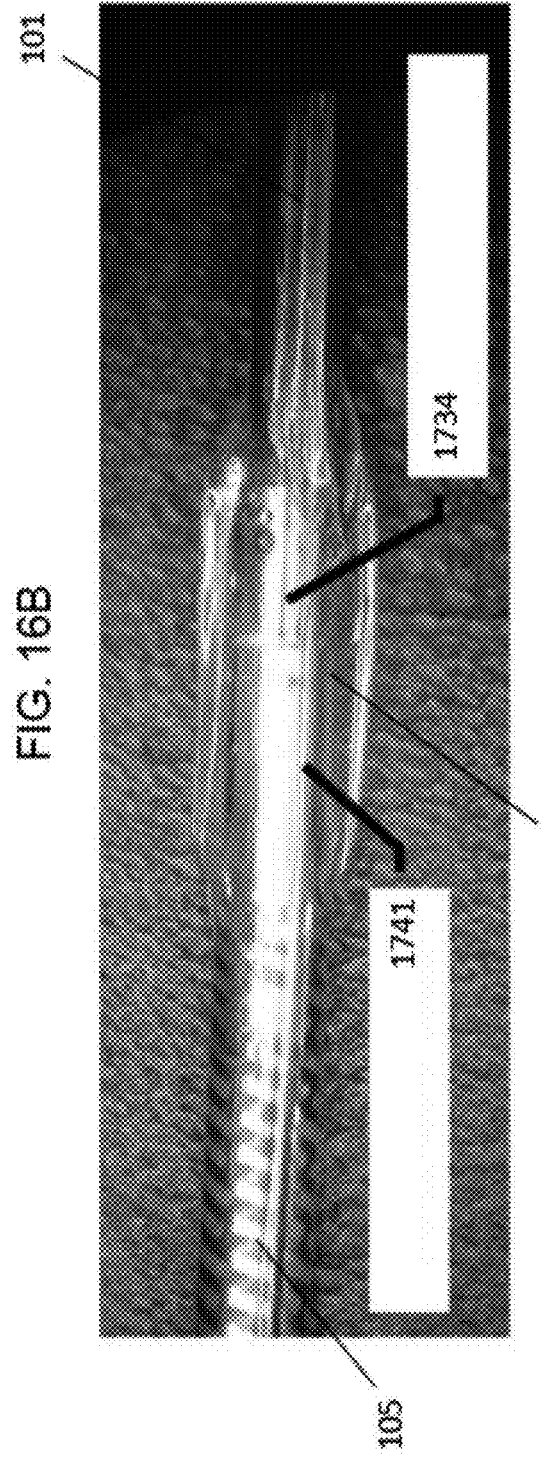
FIG. 16B
FIG. 16C

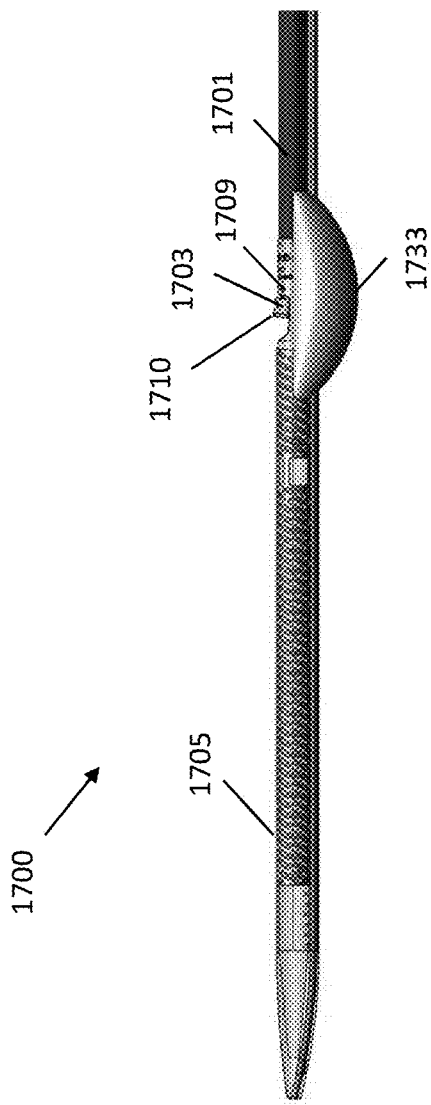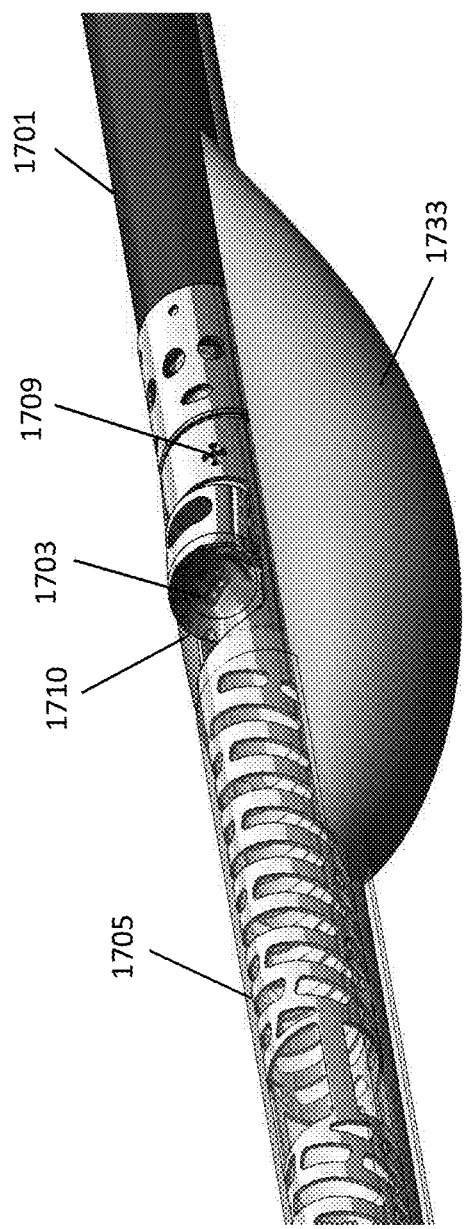
FIG. 17A
FIG. 17B

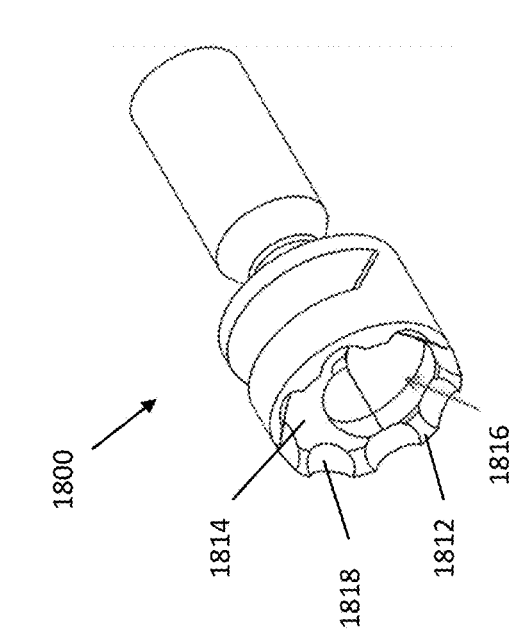
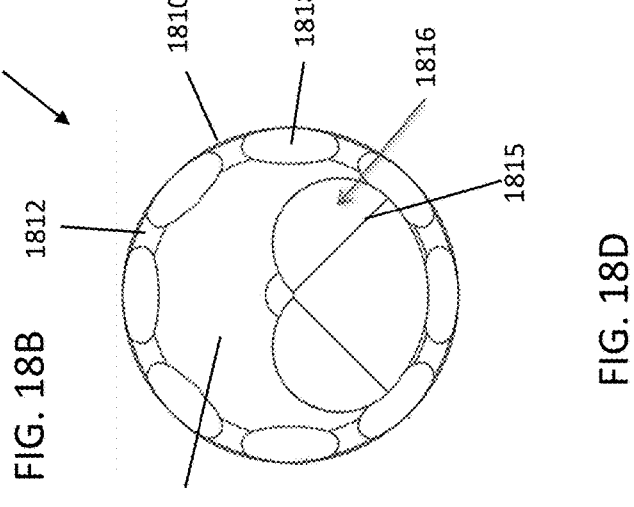
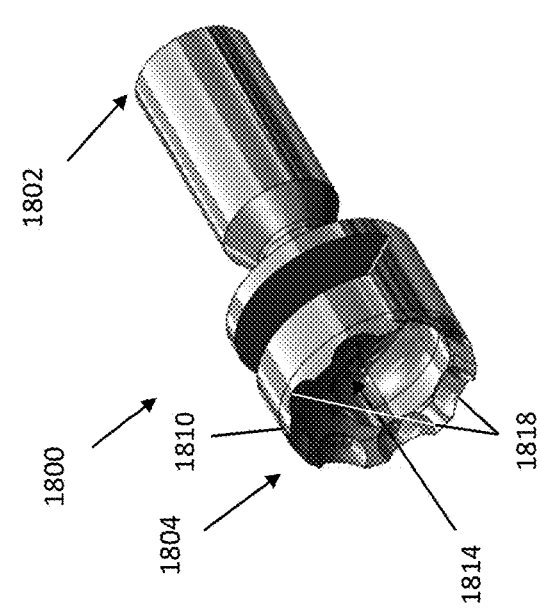
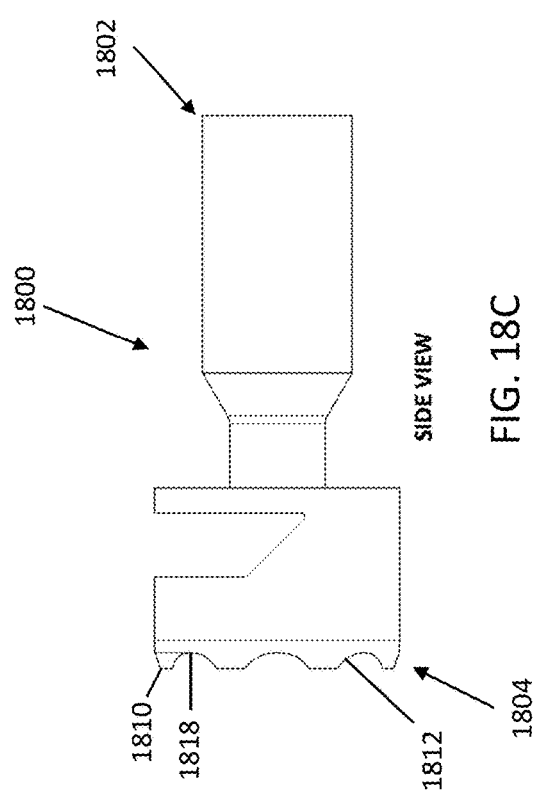
FIG. 18A
FIG. 18B
FIG. 18C
FIG. 18D

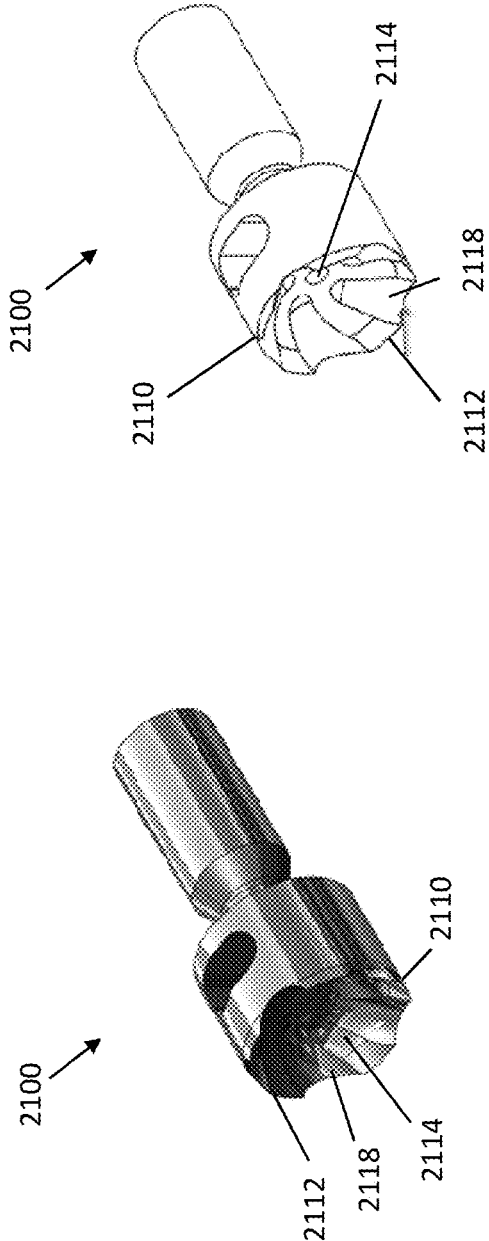
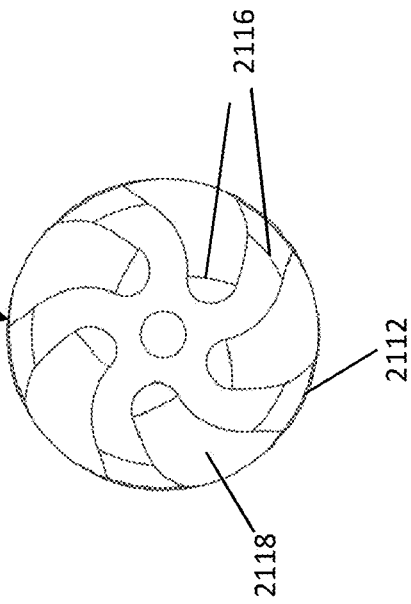
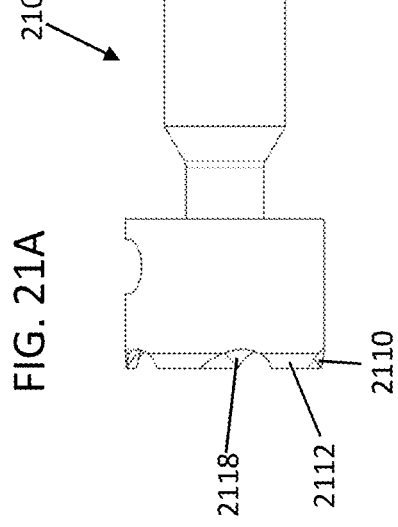
FIG. 21A
FIG. 21B
FIG. 21C
FIG. 21D

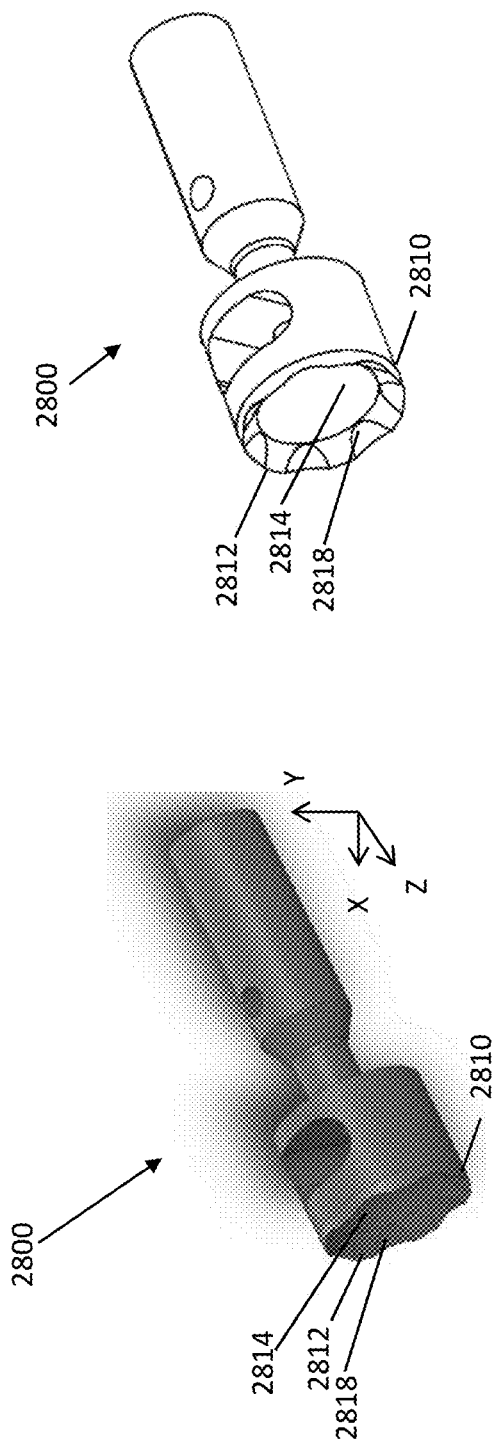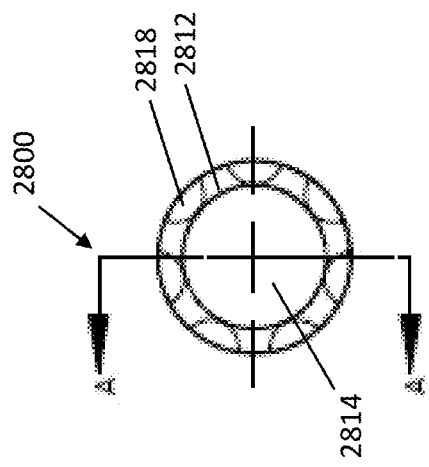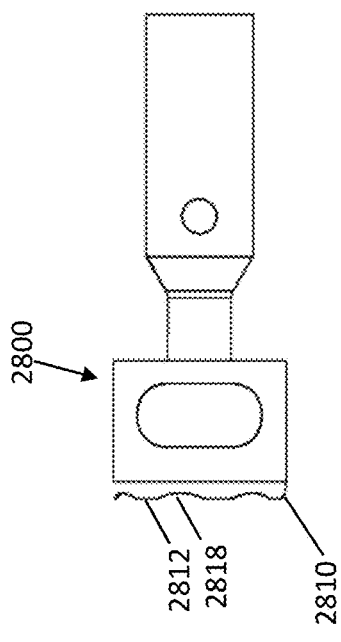

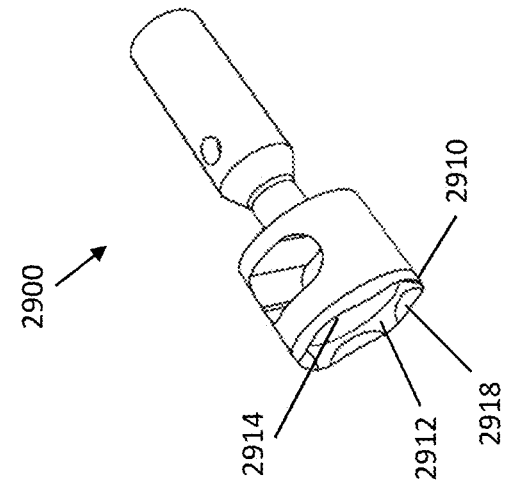
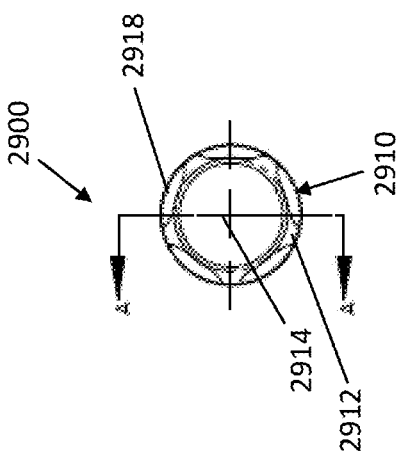
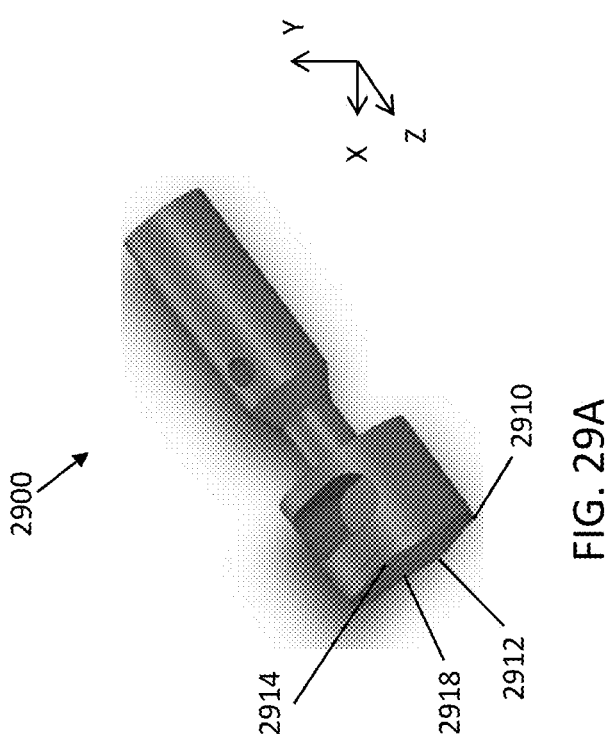
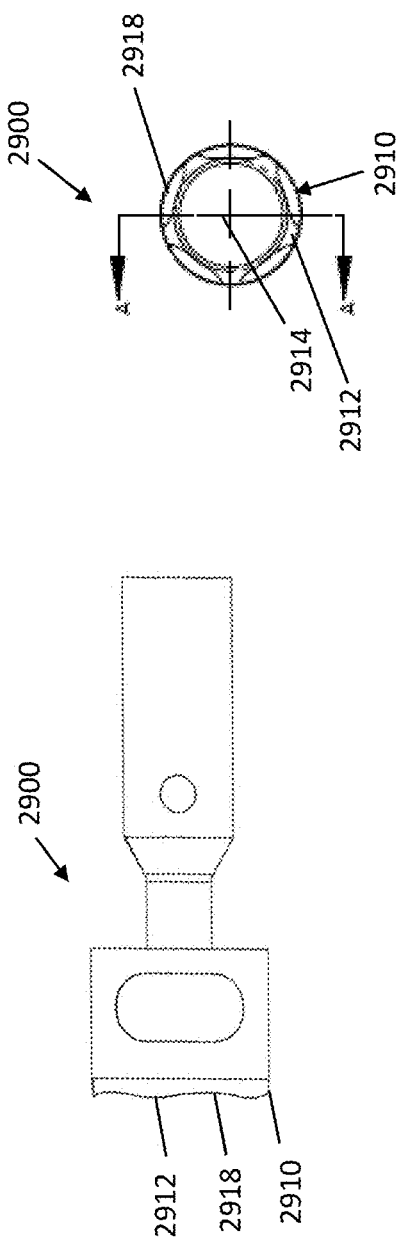
FIG. 29B
FIG. 29D
FIG. 29A
FIG. 29C

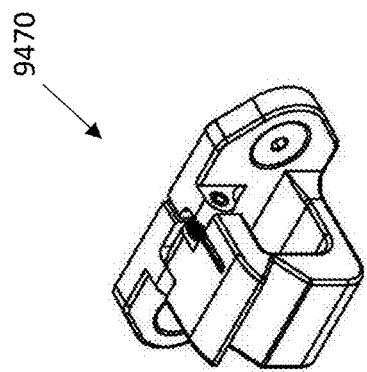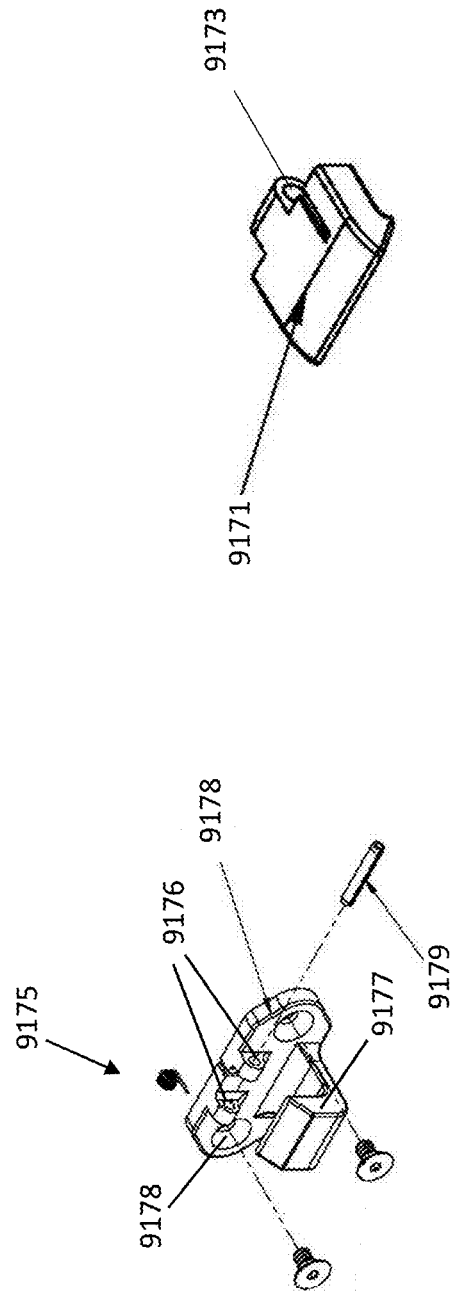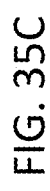
FIG. 35A
FIG. 35B
FIG. 35C

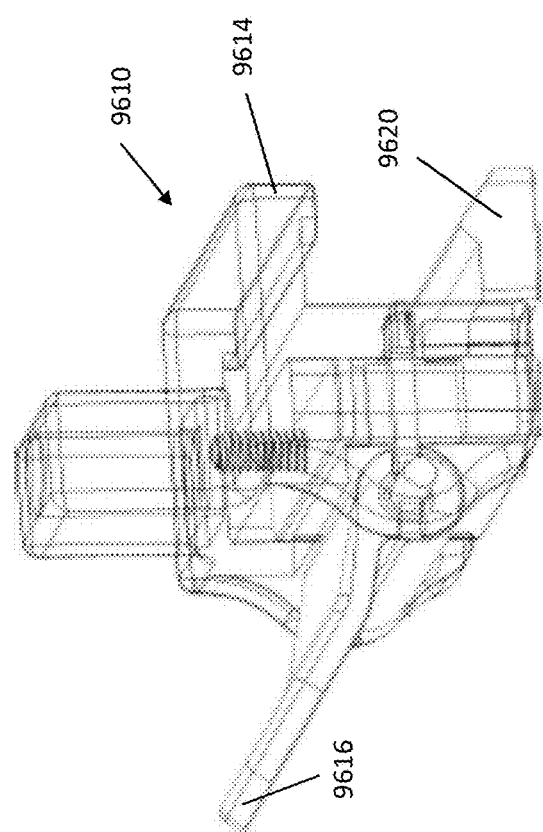
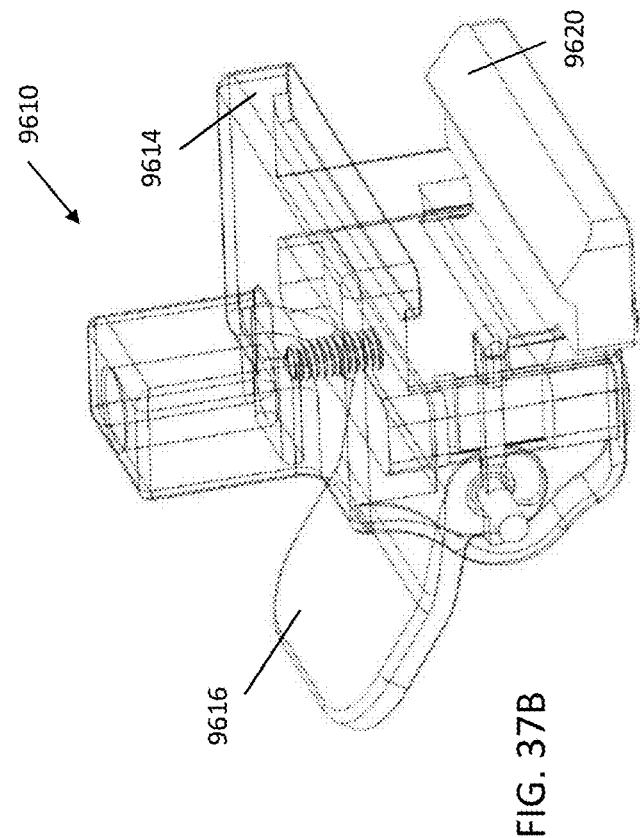
FIG. 37A
FIG. 37B

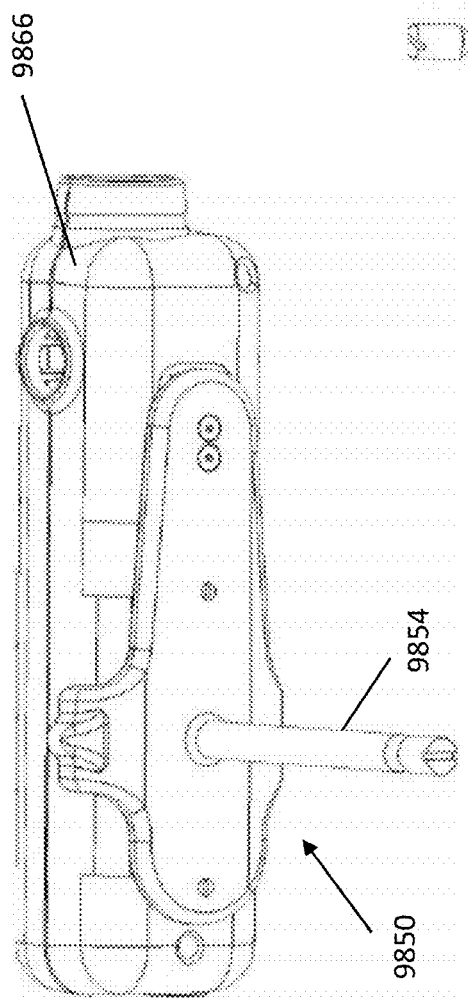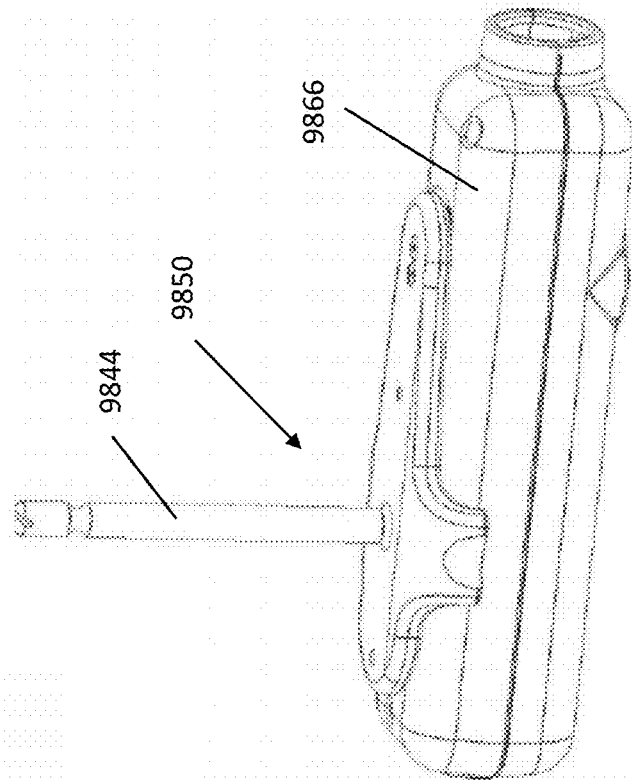
FIG. 39A
FIG. 39B

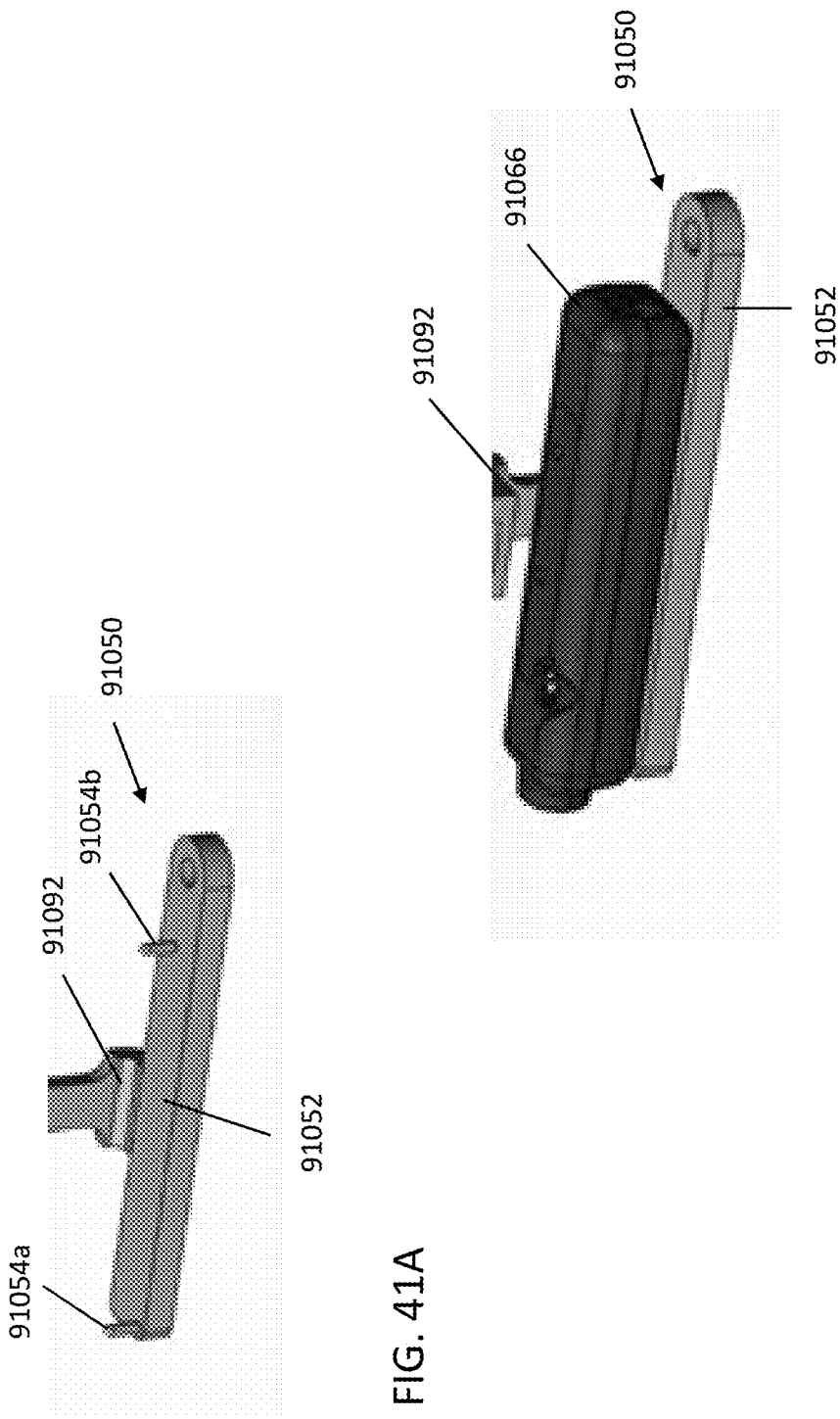

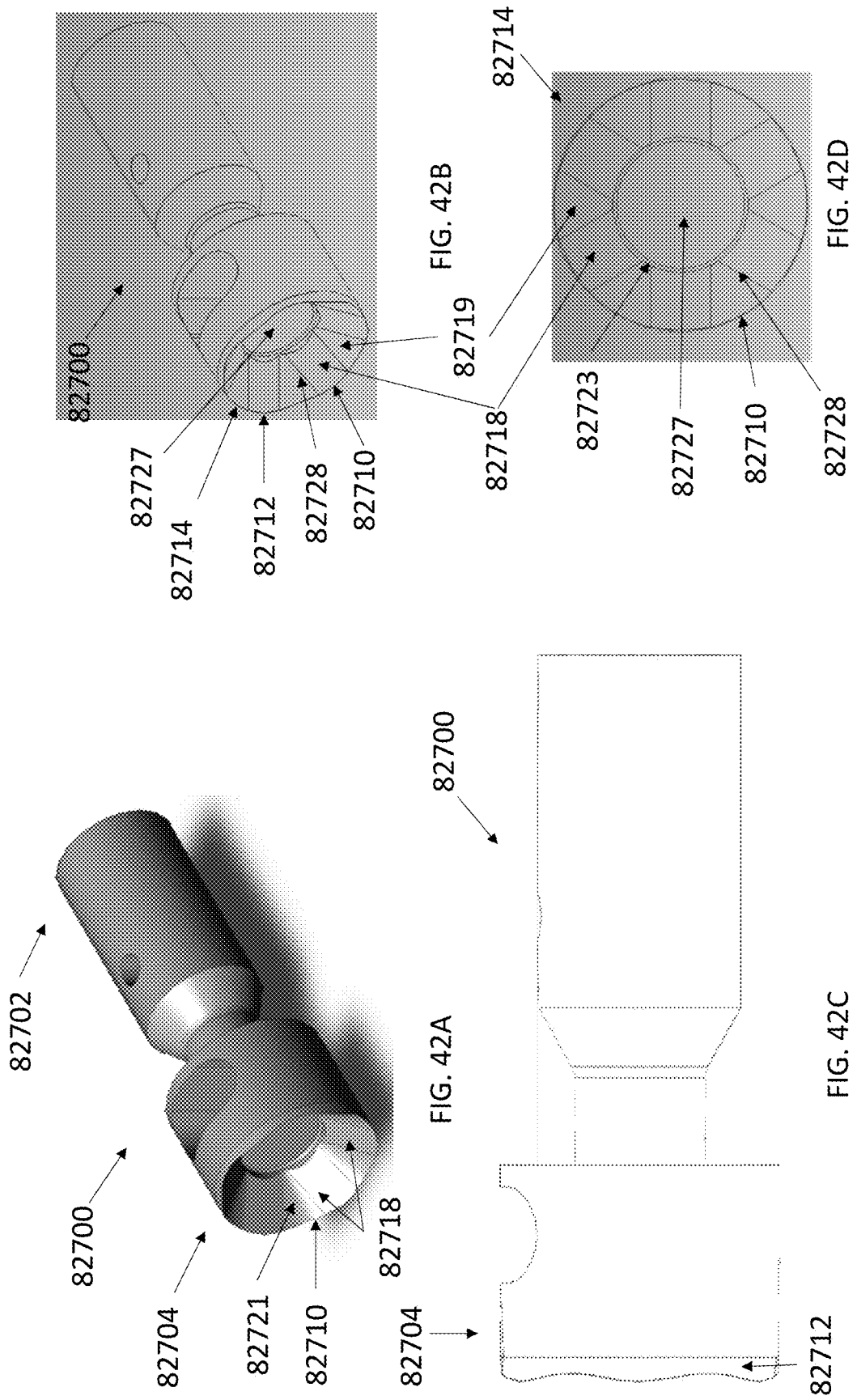

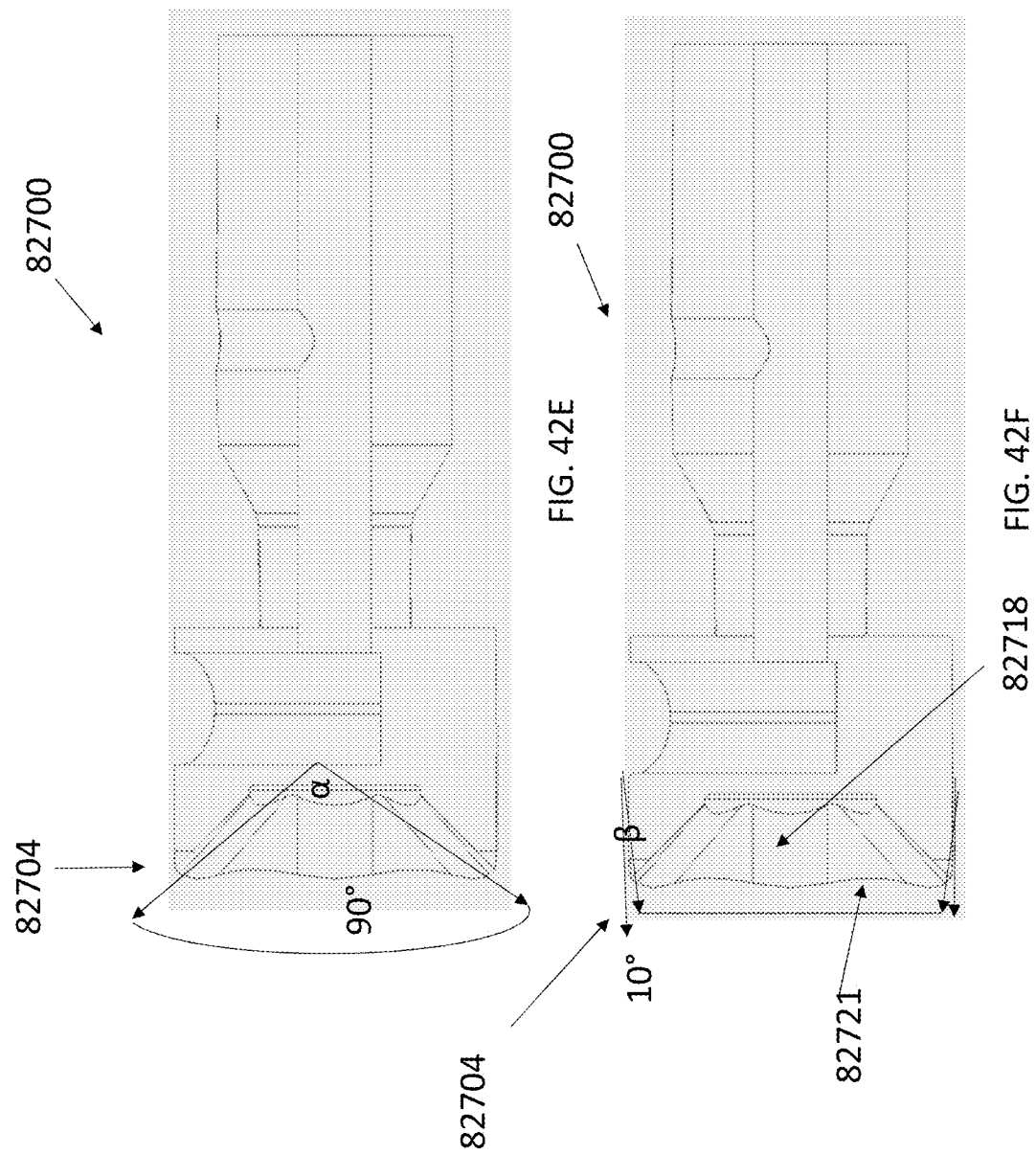

ATHERECTOMY CATHETER WITH SERRATED CUTTER

CROSS REFERENCE TO RELATED APPLICATIONS

This application is a continuation of U.S. patent application Ser. No. 16/148,246, filed Oct. 1, 2018, titled "ATHERECTOMY CATHETER WITH SERRATED CUTTER," now U.S. Patent Application Publication No. 2019/0029714 which is a continuation-in-part of PCT/US2017/025555, filed Mar. 31, 2017, titled "ATHERECTOMY CATHETER WITH SERRATED CUTTER," now International Publication No. WO 2017/173370 which claims priority to U.S. Provisional Patent Application No. 62/317,214, filed Apr. 1, 2016, titled "ATHERECTOMY CATHETERS AND OCCLUSION CROSSING DEVICES" and to U.S. Provisional Patent Application No. 62/317,231, filed Apr. 1, 2016, titled "SUPPORT ARM ASSEMBLY," the entireties of which are incorporated by reference herein.

This application may be related to PCT Patent Application No. PCT/US2015/014613, filed Feb. 5, 2015, titled, "ATHERECTOMY CATHETERS AND OCCLUSION CROSSING DEVICES", Publication No. WO2015/120146A1, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Peripheral artery disease (PAD) and coronary artery disease (CAD) affect millions of people in the United States alone. PAD and CAD are silent, dangerous diseases that can have catastrophic consequences when left untreated. CAD is the leading cause of death in the United States while PAD is the leading cause of amputation in patients over 50 and is responsible for approximately 160,000 amputations in the United States each year.

Coronary artery disease (CAD) and Peripheral artery disease (PAD) are both caused by the progressive narrowing of the blood vessels most often caused by atherosclerosis, the collection of plaque or a fatty substance along the inner lining of the artery wall. Over time, this substance hardens and thickens, which can cause an occlusion in the artery, completely or partially restricting flow through the artery. Blood circulation to the arms, legs, stomach and kidneys brain and heart may be reduced, increasing the risk for stroke and heart disease.

Interventional treatments for CAD and PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked.

In certain instances of CAD and PAD, extensive coronary calcification may occur. An increased risk of coronary heart disease is associated with extensive coronary calcification and is a sign of advanced atherosclerosis. Calcified plaque is more difficult to break apart than non-calcified plaque masses. As such, current atherectomy cutters used may not be as effective for breaking down calcified plaques. Thus, it would be advantageous to have a cutter that is better able to attack calcified plaque deposits during an atherectomy procedure.

Atherectomy catheter devices and the corresponding systems and methods that may address some of these concerns are described and illustrated below.

SUMMARY OF THE DISCLOSURE

Described herein are atherectomy catheters and methods of using them.

In general, in one embodiment, an atherectomy catheter device includes an elongate body, a drive shaft extending proximally to distally within the elongate body, and a cutter attached to the drive shaft. The cutter includes a serrated annular cutting edge formed on a distal edge of the cutter and a recessed bowl extending radially inwards from the annular cutting edge to a center of the cutter. The recessed bowl has a first curvature. The cutter further includes a plurality of grinding segments extending inwardly from the distal edge within the bowl. Each of the plurality of segments has a second curvature that is different from the first curvature.

This and other embodiments can include one or more of the following features. Each of the plurality of grinding segments can be a flat facet configured to break calcified and hard fibrous disease in an artery. The second curvature can be larger than the first curvature, or smaller than the first curvature. The plurality of facets can be flat such that the second curvature is zero. The second curvature can be smaller than the first curvature. Each of the plurality of grinding segments can form a convex portion of the serrated annular cutting edge. Each of the plurality of grinding segments can form a concave portion of the serrated annular cutting edge. The serrated annular cutting edge can be angled radially inward relative an outer diameter of the elongate body. The serrated annular cutting edge can extend radially inward relative an outer diameter of the elongate body by 2 degrees to 12 degrees. The plurality of grinding segments can be disposed symmetrically around a circumference of the recessed bowl. The plurality of grinding segments can be disposed asymmetrically around a circumference of the bowl. The recessed bowl can further include a second recessed cavity off-center within the bowl. The bowl can further include a symmetric helical pattern of depressions that can extend from the serrated cutting edge inward towards the center of the cutter. The serrated annular cutting edge can include V-shaped cutouts extending along an outer wall of the cutter. The serrated annular cutting edge can include a plurality of shallow cutouts.

In general, in one embodiment, an atherectomy catheter device includes an elongate body, a drive shaft extending proximally to distally within the elongate body, and a cutter attached to the driveshaft. The cutter includes a serrated annular cutting edge formed on a distal edge of the cutter, the serrated annular cutting edge angled radially inward relative an outer diameter of the elongate body, and a recessed bowl extending radially inwards from the annular cutting edge to a center of the cutter.

This and other embodiments can include one or more of the following features. The cutter can further include a plurality of grinding segments extending inwardly from the distal edge within the bowl. Each of the plurality of grinding segments can have a second curvature that can be different from the first curvature. The plurality of segments can be configured to break calcified and hard fibrous disease in an artery. Each of the plurality of grinding segments can be a flat facet. The second curvature can be smaller than the first curvature. Each of the plurality of grinding segments can form a convex portion of the serrated annular cutting edge. Each of the plurality of grinding segments can form a concave portion of the serrated annular cutting edge. The serrated annular cutting edge can be angled radially inward relative an outer diameter of the elongate body by 2 degrees to 12 degrees.

In general, in one embodiment, an atherectomy catheter device includes an elongate body, a drive shaft extending proximally to distally within the elongate body, and a cutter attached to the driveshaft. The cutter includes a serrated annular cutting edge formed on a distal edge of the cutter. The serrated annular cutting edge includes a plurality of portions. Each of the plurality of portions have a convex shape and a recessed bowl extending radially inwards from the annular cutting edge to a center of the cutter.

This and other embodiments can include one or more of the following features. The cutter can further include a plurality of grinding segments extending inwardly from the distal edge within the bowl. Each of the plurality of grinding segments can have a second curvature that is different from the first curvature. The plurality of grinding segments can be configured to break calcified and hard fibrous disease in an artery. Each of the plurality of grinding segments can form a convex portion of the serrated annular cutting edge. Each of the plurality of grinding segments can be a flat facet. The second curvature can be smaller than the first curvature. The serrated annular cutting edge can be angled radially inward relative an outer diameter of the elongate body. The annular cutting edge can extend radially inward relative an outer diameter of the elongate body by 2 degrees to 12 degrees. The plurality of grinding segments can be disposed symmetrically around a circumference of the recessed bowl. The plurality of grinding segments can be disposed asymmetrically around a circumference of the recessed bowl.

In general, in one embodiment, an atherectomy catheter device includes an elongate body, a hollow distal tip extending from a distal end of the elongate body, a drive shaft extending proximally to distally within the elongate body, and a cutter attached to the driveshaft. The cutter has a serrated annular cutting edge formed on the distal end of the cutter and a recessed bowl extending radially inwards from the cutting edge to the center of the cutter.

This and other embodiments can include one or more of the following features. The bowl may be symmetric. The bowl may further include a second recessed cavity. The second recessed cavity may be positioned off center within the bowl. The second recessed cavity may cover about a third to about half of an area of the bowl. The secondary recessed cavity may include three regions. In this case, the seams delineating the three regions may be raised and form sharp edges. The recessed bowl may further include protruding features that are configured to contact with and grip onto calcified plaque. The serrated cutting edge may further include a series of half-circle scooped cutouts disposed around the perimeter of the serrated cutting edge. The recessed bowl may further include a plurality of off-axis scooped indentations that extend from the serrated cutting edge inward towards the center of the cutter. Intersections between the serrated cutting edge and the plurality of off-axis scooped indentations may form curved cutouts. The plurality of off-axis scooped indentations may further include seams that are raised relative to the rest of the off-axis scooped indentation surface and where the seams may have a sharp edge. The recessed bowl may further include a symmetric helical pattern of depressions that extends from the serrated cutting edge inward towards the center of the cutter, where seams that define the helical pattern can be raised relative to the rest of the symmetric helical pattern surface, and where the seams may have a sharp edge. The serrated annular cutting edge may include V-shaped cutouts that extend along an outer wall of the cutter. The serrated annular cutting edge can include asymmetric V-shaped cutouts that extend along an outer wall of the cutter. The serrated annular cutting edge may also include shallow cutouts disposed along its perimeter that extends along an outer wall of the cutter.

In general, in one embodiment, an atherectomy catheter device includes an elongate body, a hollow distal tip extending from a distal end of the elongate body, a drive shaft extending proximally to distally within the elongate body, and a cutter attached to the driveshaft. The cutter has a smooth annular cutting edge formed on the distal end of the cutter and a recessed bowl extending radially inwards from the cutting edge to a center of the cutter. The recessed bowl includes a series of pockets disposed along the recessed bowl's interior surface.

In general, in one embodiment, an atherectomy catheter device includes an elongate body, a hollow distal tip extending from a distal end of the elongate body, a drive shaft extending proximally to distally within the elongate body, and a cutter attached to the driveshaft. The cutter has a smooth annular cutting edge formed on the distal end of the cutter, a recessed bowl extending radially inwards from the cutting edge to a center of the cutter, and a cutter outer wall having a series of grooves that extend from just beneath the smooth annular cutting edge to the cutter out wall's bottom edge.

In general, in one embodiment, an atherectomy cutter includes a proximal end configured to couple with an atherectomy catheter, a distal end, a cutting edge disposed on the distal end, and a recessed bowl region disposed between the proximal end and the distal end. The cutting edge is disposed on an outer rim of the bowl region and includes a series of half circle cut outs distributed along a perimeter of the cutting edge.

In general, in one embodiment, an atherectomy cutter includes a proximal end configured to couple with an atherectomy catheter, a distal end, a cutting edge disposed on the distal end, and a bowl region disposed between the proximal end and the distal end. The cutting edge is disposed on an outer rim of the bowl region, and the bowl region includes an off-axis second cavity.

In general, in one embodiment, an atherectomy cutter includes a proximal end configured to couple with an atherectomy catheter, a distal end, a cutting edge disposed on the distal end, and a bowl region disposed between the proximal end and the distal end. The cutting edge is disposed on an outer rim of the bowl region, and the bowl region includes a series of off-axes scooped cuts that extend from the cutting edge towards the center of the bowl. An intersection between the cutting edge and each off-axes scooped cut forms an arced cut out.

In general, in one embodiment, an atherectomy cutter includes a proximal end configured to couple with an atherectomy catheter, a distal end, a cutting edge disposed on the distal end, and a bowl region disposed between the proximal end and the distal end. The cutting edge is disposed on an outer rim of the bowl region, and the bowl region includes a series of helically-patterned depressions that extend from an interior of the bowl region to the cutting edge. The cutting edge includes curved cut outs where the helically-patterned depressions intersect the cutting edge.

In general, in one embodiment, an atherectomy catheter includes an elongate body, a hollow distal tip extending from a distal end of the elongate body, a drive shaft extending proximally to distally within the elongate body, and a cutter attached to the driveshaft. The cutter has a recessed bowl extending radially inwards from the cutting edge to a center of the cutter, a cutter outer wall, and a serrated annular cutting edge formed on a distal end of the cutter. The serrated annular cutting edge includes a series of V-shaped grooves that extend from the serrated annular cutting edge and along the cutter outer wall to a proximal end of the cutter.

In general, in one embodiment, an atherectomy catheter includes an elongate body, a hollow distal tip extending from a distal end of the elongate body, a drive shaft extending proximally to distally within the elongate body, and a cutter attached to the driveshaft. The cutter has a recessed bowl extending radially inwards from the cutting edge to a center of the cutter, a cutter outer wall, and a serrated annular cutting edge formed on a distal end of the cutter. The serrated annular cutting edge includes a series of shallow cutouts that extend from the serrated annular cutting edge and along the cutter outer wall to a proximal end of the cutter.

In general, in one embodiment, an atherectomy catheter device includes an elongate body, a hollow distal tip extending from a distal end of the elongate body, a drive shaft extending proximally to distally within the elongate body, and a cutter attached to the driveshaft. The cutter has a recessed bowl extending radially inwards from the cutting edge to a center of the cutter, a cutter outer wall, and a serrated annular cutting edge formed on a distal end of the cutter. The serrated annular cutting edge includes a series of asymmetric V-shaped grooves that extend from the serrated annular cutting edge and along the cutter outer wall to a proximal end of the cutter.

In general, in one embodiment, an atherectomy catheter device includes an elongate body, a drive shaft, and a cutter. The drive shaft extends proximally to distally within the elongate body. The cutter is attached to the driveshaft and includes a serrated annular cutting edge and a recessed bowl. The serrated annular edge is formed on a distal edge of the cutter and includes a plurality of convex portions and each of the plurality of portions has a convex shape. The recessed bowl extends radially inwards from the annular cutting edge to a center of the cutter. This and other embodiments can include one or more of the following features.

The cutter further can include a plurality of grinding segments within the recessed bowl extending from the distal edge and each of the plurality of grinding segments can extend radially inwards relative to neighboring portions. The plurality of grinding segments can be configured to break calcified and hard fibrous disease tissue in an artery.

Each of the plurality of grinding segments can form a convex portion of the plurality of convex portions of the serrated annular cutting edge. Each of the plurality of grinding segments may be a flat facet. Each of the plurality of grinding segments may be a curved facet. Each of the plurality of grinding segments may be configured to extend at least 70% distally to proximally along the recessed bowl. Each of the plurality of grinding segments may be substantially square, rectangular, or trapezoidal in shape. Each of the plurality of grinding segments may form a convex portion of the serrated annular cutting edge.

The serrated annular cutting edge can be angled radially inward relative an outer diameter of the elongate body. The serrated annular cutting edge can extend radially inward relative an outer diameter of the elongate body by 2 degrees to 12 degrees. The serrated annular cutting edge can include a continuous wavy shape.

The plurality of grinding segments can be disposed symmetrically around a circumference of the recessed bowl. The plurality of grinding segments can be disposed asymmetrically around a circumference of the recessed bowl.

In general, in one embodiment, an atherectomy catheter device includes an elongate body, a drive shaft, and a cutter. The drive shaft extends proximally to distally within the elongate body. The cutter is attached to the driveshaft and includes a serrated annular cutting edge add a recessed bowl. The serrated annular cutting edge is formed on a distal edge of the cutter and is angled radially inward relative an outer diameter of the elongate body. The recessed bowl extends radially inwards from the annular cutting edge to a center of the cutter. This and other embodiments can include one or more of the following features.

The cutter further can include a plurality of grinding segments within the recessed bowl extending from the distal edge and each of the plurality of grinding segments can extend radially inwards relative to neighboring portions. The plurality of grinding segments can be configured to break calcified and hard fibrous disease tissue in an artery.

Each of the plurality of grinding segments can form a convex portion of the plurality of convex portions of the serrated annular cutting edge. Each of the plurality of grinding segments can be a flat facet. Each of the plurality of grinding segments can be a curved facet. Each of the plurality of grinding segments can extend at least 70% distally to proximally along the recessed bowl. Each of the plurality of grinding segments can be substantially square, rectangular, or trapezoidal in shape. Each of the plurality of grinding segments can form a convex portion of the serrated annular cutting edge. Each of the neighboring portions can form a concave portion of the serrated annular cutting edge.

The serrated annular cutting edge can be angled radially inward relative an outer diameter of the elongate body by 2 degrees to 12 degrees. The serrated annular cutting edge can include a continuous wavy shape.

The plurality of grinding segments can be disposed symmetrically around a circumference of the recessed bowl. The plurality of grinding segments can be disposed asymmetrically around a circumference of the recessed bowl.

Also described herein are support systems for maintaining medical components, such as controller components of an atherectomy catheter, at a convenient location with easy maneuverability relative to the treatment site.

In general, in one embodiment, a catheter controller support apparatus includes a rail clamp configured to releasably attach to a rail, a support arm having at least two segments joined by a swivel joint that is configured to couple with the rail clamp through a coupling post, and a catheter controller mount coupled to the support arm and configured to securely maintain a catheter controller.

This and other embodiments may include one or more of the following features. The rail clamp may include a top surface, a support arm coupler disposed on the top surface, a support arm coupling aperture disposed on the support arm coupler, a top jaw, a bottom jaw hinged with the top jaw, a lever for actuating the up and down movement of the top and the bottom jaw, and a support arm securing aperture for locking the support arm in position. The rail clamp may further include a course adjustment knob for increasing and decreasing the distance between the top jaw and the bottom jaw. The rail clamp may further include at least one sleeve bearing contained within the arm coupling aperture. The support arm may further include a first friction knob configured to maintain the swivel joint in a fixed position once the desired position is obtained. The support arm may further include a second swivel joint and a corresponding second friction knob adjacent to the coupling post configured to provide articulated/segmental adjustment of the support arm. The support arm may further include a catheter mount coupler adapted to couple to the catheter controller mount, wherein the catheter mount coupler may further include a mount positioning lever that configured to adjust the angle at which the catheter controller mount is positioned. The support arm may further include at least one cable retainer. The catheter controller mount may further include a catheter controller coupler, wherein the catheter controller coupler may be a post or other protrusion extending from the base of the catheter controller mount that inserts into a corresponding aperture of the catheter controller. The catheter controller mount may further include a controller mount support latch. The catheter controller mount may include a clip having a jaw wide enough to accommodate the catheter controller. The catheter controller mount may include a mount support base, a mount support coupler configured to couple to a catheter controller unit, and a mount support latch for stabilizing the coupled catheter controller unit.

In general, in one embodiment, a catheter controller support apparatus includes a rail clamp configured to releasably attach to a rail, a support arm coupler disposed on the top surface, a support arm coupling aperture disposed on the support arm coupler, a top jaw, a bottom jaw hinged with the top jaw, a lever for actuating the up and down movement of the top and the bottom jaw, and a support arm securing aperture for locking the support arm in position. The rail clamp includes a top surface. The support arm has at least two segments joined by a swivel joint that is configured to couple with the rail clamp through a coupling post. The at least two segments are coupled by a swivel joint and at least one friction knob maintains the swivel joint in a fixed position once the desired position is obtained. The catheter controller support apparatus further includes a catheter controller mount coupled to the support arm and configured to securely maintain a catheter controller. The catheter controller mount further includes a catheter controller coupler. The catheter controller coupler includes a post or other protrusion extending from the base of the catheter controller mount that inserts into a corresponding aperture of the catheter controller, a mount support base, a mount support coupler able to couple to a catheter controller unit, and a mount support latch configured to stabilize the coupled catheter controller unit.

This and other embodiments may include one or more of the following features. The rail clamp may further include at least one sleeve bearing contained within the arm coupling aperture. The support arm may further include a catheter mount coupler configured to couple to the catheter controller mount, wherein the catheter mount coupler may further include a mount positioning lever that is configured to adjust the angle at which the catheter controller mount is positioned. The support arm may further include at least one cable retainer.

BRIEF DESCRIPTION OF THE DRAWINGS

FIGS. 1A-1C illustrate a side perspective view of the end of an exemplary atherectomy device having an offset hinged region, a bushing, and an imaging/cutting assembly with a neck region that engages the bushing. FIG. 1B shows the catheter with the housing for the hollow distal tip removed. FIG. 1C shows the catheter of FIG. 1B with the proximal connector to the outer sleeve of the elongate body removed, showing the bushing and rotatable drive shaft.

FIGS. 4B, 4C and 4D each show the catheter of FIG. 4A with various components removed to allow description of internal parts.

FIG. 8A shows a panoramic OCT image of a blood vessel through the nosecone of an atherectomy catheter, as identified by the arrow in FIG. 8B.

FIG. 9A shows a panoramic OCT image of a blood vessel taken with an atherectomy catheter through the cutting window(s) when the nosecone is closed and the cutter is in a passive position, as identified by the arrow in FIG. 9B.

FIGS. 11A-11B show another embodiment of an atherectomy catheter having a cutter engaging distal surface that is normal to the longitudinal axis of the catheter. FIG. 11A shows a cross-section of the catheter while FIG. 11B shows a side view of the bushing.

FIGS. 12A-12B show another embodiment of an atherectomy catheter having a cutter engaging distal surface that is at an angle relative to the longitudinal axis so as to provide only a point of contact with the distal surface of the cutter. FIG. 12A shows a cross-section of the catheter. FIG. 12B shows a side view of the bushing.

FIGS. 16A-16C show an atherectomy catheter with a crescent-shaped balloon.

FIG. 17A shows an atherectomy catheter having a serrated cutting edge.

FIG. 17B shows a close-up of the serrated cutter portion of the atherectomy catheter of FIG. 17A.

FIGS. 18A-18E show an atherectomy catheter cutter having a serrated cutting edge and an asymmetric pocket within the cutter body. FIGS. 18A and 18B are isometric views of the cutter. FIG. 18C is a side view of the cutter. FIG. 18D is a front view of the cutter. FIG. 18E is a cross-sectional side view of the cutter.

FIGS. 19A and 19B show isometric views of the cutter. FIG. 19C is a side view of the cutter. FIG. 19D is a front view of the cutter. FIG. 19E is a cross-sectional side view of the cutter.

FIGS. 20A and 20B show isometric views of the cutter. FIG. 20C is a side view of the off-axis cutter. FIG. 20D is a front view of the cutter. FIG. 20E is a cross-sectional side view of the cutter.

FIGS. 21A-21E show an atherectomy catheter cutter having a helical depressions therein. FIGS. 21A and 21B show isometric views of the cutter. FIG. 21C is a side view of the cutter. FIG. 21D is a front view of the cutter. FIG. 21E is a cross-sectional side view of the cutter.

FIG. 22A is a perspective view of the cutter and FIG. 22B is a front view of the bowl region.

FIG. 23A is a perspective view of the cutter and FIG. 22B is a front view of the bowl region.

FIG. 24A shows a perspective view of the cutter, while FIG. 24B is a front view of the bowl region.

FIG. 25A shows a perspective view of the cutter, while FIG. 25B is a front view of the bowl region.

FIG. 26A shows a perspective view of the cutter, while FIG. 26B shows a front view of the bowl region.

FIG. 27A is a shaded perspective view of the cutter, FIG. 27B is a line perspective view of the cutter, FIG. 27C is a side view of the cutter, FIG. 27D is a front view of the cutter and FIG. 27E is a cross-sectional side view of the cutter.

FIGS. 28A-28E illustrate an atherectomy catheter device including a cutter having a serrated annular cutting edge, a recessed bowl, and a plurality of segments according to another embodiment. FIG. 28A is a shaded perspective view of the cutter, FIG. 28B is a line perspective view of the cutter, FIG. 28C is a side view of the cutter, FIG. 28D is a front view of the cutter and FIG. 28E is a cross-sectional side view of the cutter.

FIGS. 29A-29E illustrate an atherectomy catheter device including a cutter having a serrated annular cutting edge, a recessed bowl, and a plurality of segments according to one embodiment. FIG. 29A is a shaded perspective view of the cutter, FIG. 29B is a line perspective view of the cutter, FIG. 29C is a side view of the cutter, FIG. 29D is a front view of the cutter and FIG. 29E is a cross-sectional side view of the cutter.

FIG. 30A is a shaded perspective view of the cutter, FIG. 30B is a line perspective view of the cutter, FIG. 30C is a side view of the cutter, FIG. 30D is a front view of the cutter and FIG. 30E is a cross-sectional side view of the cutter.

FIG. 31A is a shaded perspective view of the cutter, FIG. 31B is a line perspective view of the cutter, FIG. 31C is a side view of the cutter, FIG. 31D is a front view of the cutter and FIG. 31E is a cross-sectional side view of the cutter.

FIG. 35A is a perspective of a cable retainer.

FIG. 35B is an exploded view of the cable retainer of FIG. 35A.

FIG. 35C is a perspective view of a top jaw of the cable retainer of FIG. 35A.

FIGS. 37A-37B shows another embodiment of a rail clamp.

FIGS. 39A-39B show another embodiment of a catheter controller mount coupled to a catheter controller.

FIG. 41A shows another embodiment of a catheter controller mount.

FIG. 41B shows the catheter controller mount of FIG. 41A coupled to a catheter controller.

FIGS. 42A-42F show an atherectomy catheter cutter having a serrated cutting edge. FIGS. 42A and 42B are isometric views of the cutter. FIG. 42C is a side view of the cutter. FIG. 42D is a front view of the cutter. FIGS. 42E-42F are cross-sectional side views of the cutter.

DETAILED DESCRIPTION

Figure 2A:
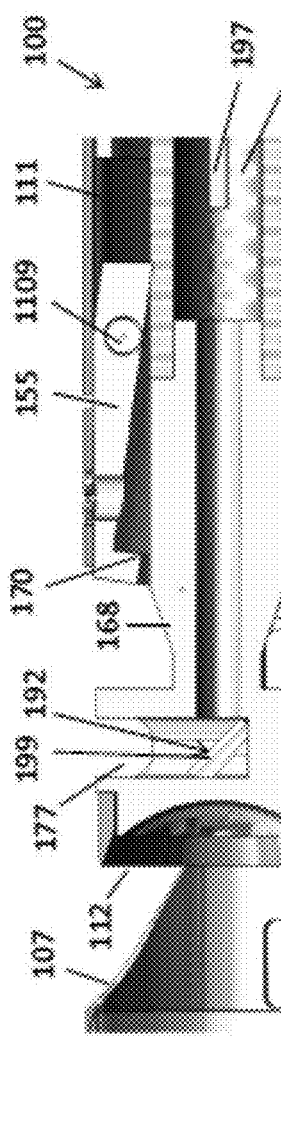
FIG. 2A shows a sectional view though an atherectomy catheter such as the one shown in FIGS. 1A-1C, with the distal tip in-line with the elongate (proximal) body region.

The atherectomy catheters described herein can include a cutter. The cutter, for example, can have a serrated annular cutting edge formed on a distal edge of the cutter and a recessed bowl extending radially inwards from the annular cutting edge to a center of the cutter. The recessed bowl can include a plurality of segments therein configured to help break up hard plaque or diseased tissue that enters the recessed bowl during use.

The atherectomy catheters described herein can further include a catheter shaft with a drive chassis on the end. The drive chassis includes a stout torque coil ("imaging torqueing coil"/drive shaft) for rotating an imaging element, a cutter, and an imaging optical fiber in the center of the torque coil. Both the imaging elements and the cutter can be part of a head that rotates with the driveshaft. The head can rotate in a single direction (e.g., clockwise). The head can further slide distally/proximally by pushing or pulling the torque coil/drive shaft. As a result of the movement of the driveshaft, a nosecone configured to hold tissue can be displaced. In some embodiments, the nosecone can open and close using an off-axis hinge. In other embodiments, a cam member and cam slot can be used to open and close the nosecone.

FIGS. 1A-3 show an example of an atherectomy catheter 100 including a nosecone that deflects to expose a cutter. The atherectomy catheter 100 can include a catheter body 101 having an outer shaft 111, a cutter 103 at a distal end of the catheter body 101, and a nosecone 105 at a distal end of the catheter body 101. The nosecone 105 can further include a cutting window 107 through which the cutting edge 112 of the cutter 103 can be exposed. The nosecone 105 can be configured to deflect away from the longitudinal axis of the catheter body 101 about a hinge point 1109, as described further below. This deflection can expose the cutter 103 through the cutting window 107 and/or radially push the cutter 103 into a wall of the vessel in which the atherectomy catheter is inserted.

Referring to FIGS. 1A-2C, the cutter 103 can be positioned between the catheter body 101 and the nosecone 105 via a bushing 155. In some embodiments, the cutter 103 can be an annular cutter with a sharp distal edge 112. The cutter 103 can be attached to a drive shaft 113 configured to rotate the cutter 103.

Figure 2B:
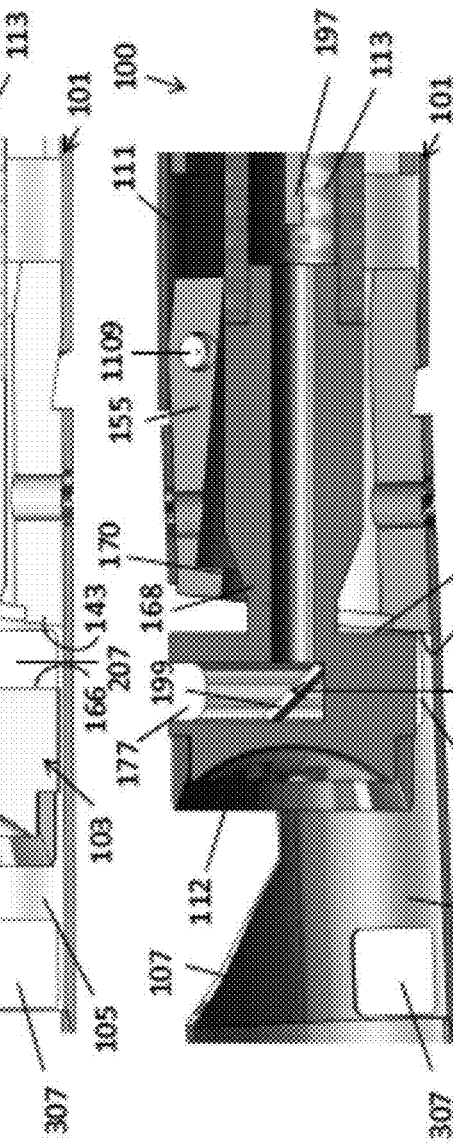
FIG. 2B shows the catheter of FIG. 2A as the tip is beginning to be displaced downward.

Further, referring still to FIGS. 2A-2B, the atherectomy catheter 100 can include an imaging element 192, such as an OCT imaging element, within the cutter 103 and proximal to the cutting edge 112 of the cutter 103. The imaging element 192 can include an optical fiber 197 that runs substantially on-axis through the center of the elongate body, such as through the driveshaft 113, to transmit the OCT signal. Further, the optical fiber 197 can run straight throughout the catheter body 101 without bending. The optical fiber 197 can be attached at the distal end to the cutter 103, such as in a slot 177 in the cutter 103. The slot can have a length that extends at least to the center of the cutter 103 so as to allow the optical fiber 197 to remain on-axis without a bend through the length of the catheter body 101 and the cutter 103. Aside from the attachment to the cutter 103, the optical fiber 197 can be otherwise be free to float within the catheter body or drive shaft 113. In other embodiments, the optical fiber 197 can be attached to the drive shaft 113 along the length thereof.

Figure 2C:
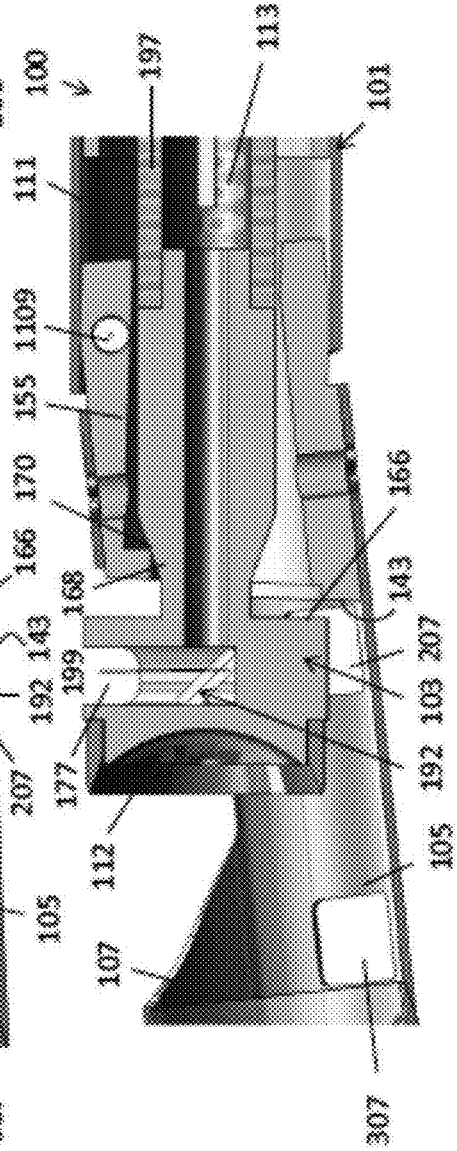
FIG. 2C shows the catheter of FIG. 2A with the tip fully displaced downward, exposing the cutting edge of the cutting/imaging assembly.

As shown in FIGS. 2A-2C, the imaging element 192 can include a reflective element 199, such as a mirror. The reflective element 199 can be located within the slot 177 in the cutter 103 to radially direct light from the optical fiber 197 into the adjacent tissue (through the cutter window 107). The reflective element 199 can be oriented at an angle relative to the axis of the optical fiber 197, such as at a 35-55 degree angle, e.g. 45 degree angle, to reflect light into the tissue. The distal end of the optical fiber 197 can be located less than 3 mm from the cutting edge, such as less than 1 mm from the cutting edge, such as less than 0.5 mm. By having the imaging element 192 close to the cutting edge, the resulting image can advantageously align with the portions of the vessel being cut.

In use, the outer shaft 111 can be configured to be turned, such as turned manually, to position the cutter window 107, cutter 103, and/or the imaging element 192 toward the desired location. The driveshaft 113 can then be rotated to rotate the cutter 103 and the imaging elements 197. Rotation of the cutter can provide cutting due to the rotational motion of the cutting edge and provide the rotation necessary to image the vessel wall via the imaging element. The drive shaft can be rotated at up to 2,000 rpm, such as approximately 1,000 rpm in a single direction, though rotation in both directions or at higher or lower speeds is possible.

Referring to FIGS. 2A-2C, the drive shaft 113 can further be configured to translate axially in the proximal and/or distal directions. Such axial movement of the drive shaft 113 can open and/or close the nosecone 105 about the hinge point 1109 (e.g., a pin in the bushing 155) to expose or conceal and protect the cutting edge 112 of the cutter 103. For example, the bushing 155 can include an inner flange 170 that extends radially inwards. The inner flange 170 can be positioned distal to the hinge point 1109. The bushing 155 can further include sloped outer distal surface 143 that angles radially inward from the distal end to the proximal end. Finally, the cutter 103 can include a proximal edge 166 and a tapered neck 168 that gets narrower from the driveshaft 113 to the head of the cutter 103. The interaction of these various elements can open and close the nosecone 105.

In one embodiment, proximal retraction of the drive shaft 113 opens the nosecone 105 to expose the cutter. For example, as the driveshaft 113 is pulled proximally, the proximal edge 166 of the cutter 103 is forced against the sloped distal surface 143 of the bushing 155. Because the sloped distal surface 143 angles radially inward from the distal end to the proximal end, the cutter 103 forces the bushing 155, and thus the nosecone 105, to deflect away from the longitudinal axis of the catheter body 101, thereby opening the nosecone 105 (see the transition from FIGS. 2A to 2B and 2B to 2C). The cutting window 107 can have an opening that is larger than the diameter of the cutter 103 and cutting edge 112 to allow the cutter 103 to protrude out of the nosecone 105 when the nosecone 105 is deflected.

In one embodiment, distal movement of the drive shaft 113 closes the nosecone 105. For example, as shown in FIGS. 2A-2C, when the drive shaft 113 is pushed distally, the tapered neck 168 of the cutter 103 will correspondingly move distally. The distal movement of the tapered neck 168 causes the inner flange 170 of the bushing 155 to drag along the widening edges of the tapered neck 168, thereby lifting the bushing 155, and correspondingly, closing the nosecone 105 (see the transition from FIGS. 2C to 2B and 2B to 2A). Because the hinge point is proximal to the inner flange 170, a mechanical advantage is achieved that allows for complete closing of the nosecone.

FIGS. 7A-7D show close-ups of the bushing 155. As shown, the bushing 155 can include two intersecting channels 721, 723 configured to hold the necked portion 168 of the imaging subassembly therein when the nosecone is in the open configuration (channel 723) and the closed configuration (channel 721). Channel 721 extends through a long distal to proximal axis of the bushing 155 while channel 723 extends at an angle relative to channel 721 and overlaps therewith. The bushing 155 can further include a hinge channel 745 formed through a top peripheral region of the bushing 155 so as to provide the pivot point 1109. The hinge channel 745 can be transverse to the channel 721.

Other mechanisms of opening and closing the nosecone are possible. For example, as shown in FIGS. 4A-4D, in one embodiment, a catheter 200 (having similar features to catheter 100 except the opening and closing mechanisms) can include a cam slot 228 in the bushing 155 that angles toward the cutting window 107 from the proximal end to the distal end. Further, a cam member 290 can be attached to the cutter 103 and configured to extend through the cam slot 228. Thus, as the driveshaft 113, and thus cam member 290, are pushed distally, the cam member 290 will move within the angled cam slot 180. The movement of the cam member 290 within the angled cam slot 180 causes the bushing 155, and thus the nosecone 150, to drop down. Conversely, to close the nosecone, the driveshaft 113 can be pulled proximally, thereby causing the cam member 290 to ride within the cam slot 228 and pull the bushing 155 back into line with the elongate body 101.

Another mechanism of opening and closing a nosecone of an atherectomy catheter 400a, b is shown in FIGS. 11A-11B and 12A-12B. The catheter 400a, b can have the same features as catheter 100 except that the outer distal surface 443a,b of the bushing 455a,b can be either normal to the longitudinal axis of the device (such that the angle α is 90 degrees), as shown in FIG. 11B or slanted radially outward from the distal end to the proximal end (such that the angle α is greater than 90 degrees and the angle with the longitudinal axis is less than 90 degrees), as shown in FIG. 12B. In the embodiment of FIGS. 12A-12B, an angled space is provided between the proximal edge 166 of the cutter and the distal surface 443b such that the only point of contact is an inner radial edge 444 of the bushing 455b. The catheter 400a will open and close similarly to as described with respect to catheter 100. However, the catheter 500b will open slightly differently in that only the inner-most radial edge 444 will interact with the proximal edge 166 of the cutter 103, as opposed to the entire surface 443, when the driveshaft 113 is pulled proximally. Such a configuration can advantageously reduce friction while opening the nosecone 105. In some embodiments, the proximal edge 166 can be angled with respect to a longitudinal axis of the catheter; in such cases, the opposing surface 443 of the bushing 455 can be either parallel to or angled (acute or obtuse) with respect to the proximal edge 166.

Figure 3:
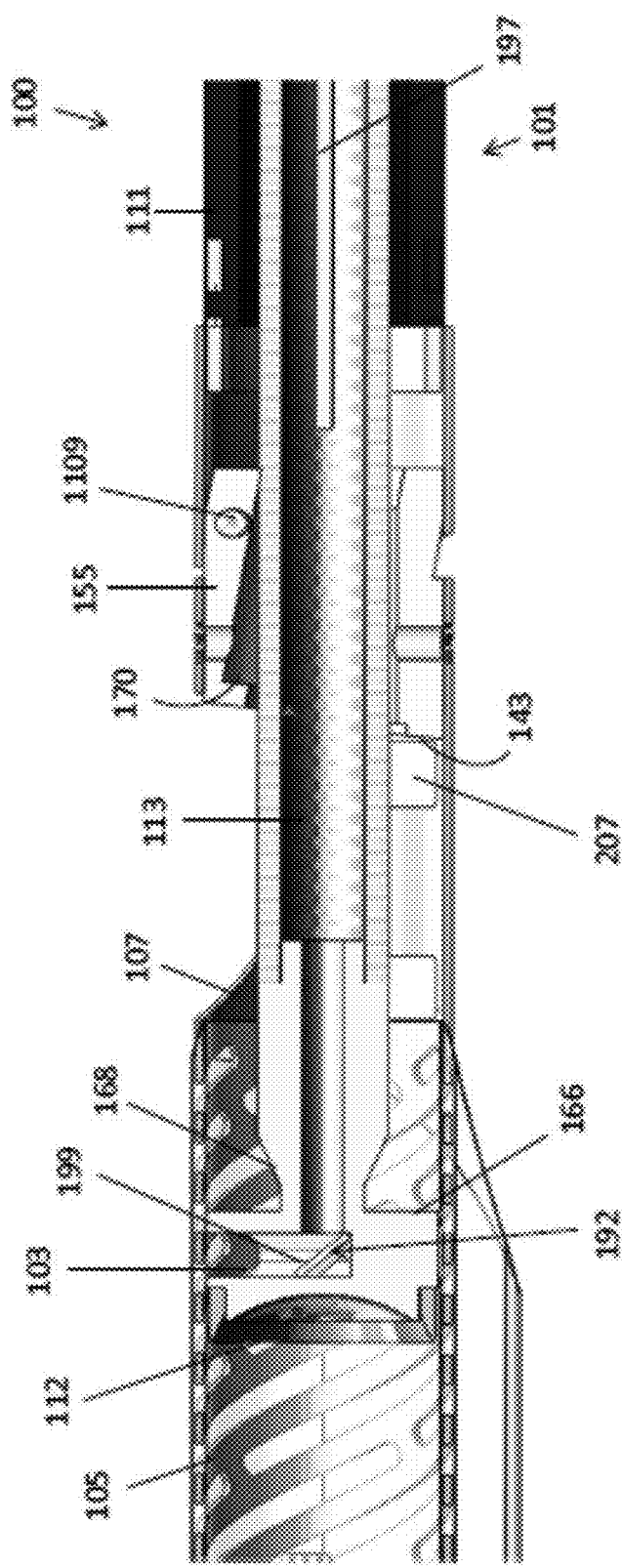
FIG. 3 shows a catheter with the cutting/imaging assembly extended distally into the distal tip region.
Figure 4A:
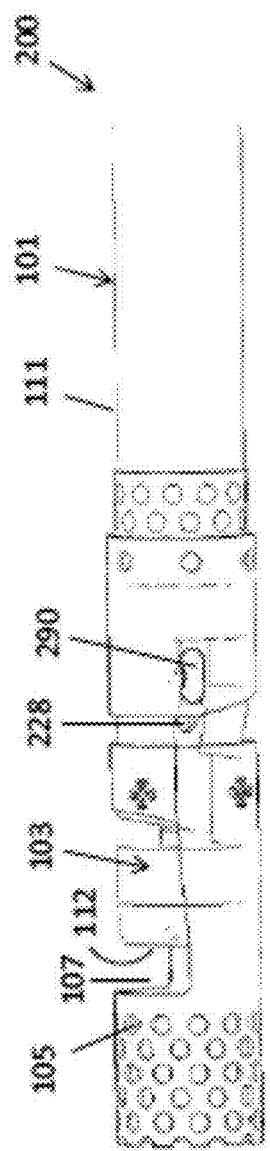
FIGS. 4A-4D illustrate another variation of an atherectomy catheter.
Figure 4B:
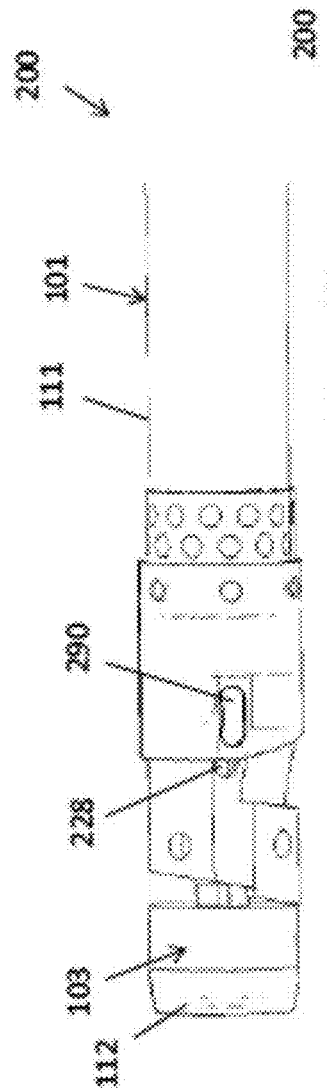
Figure 4C:
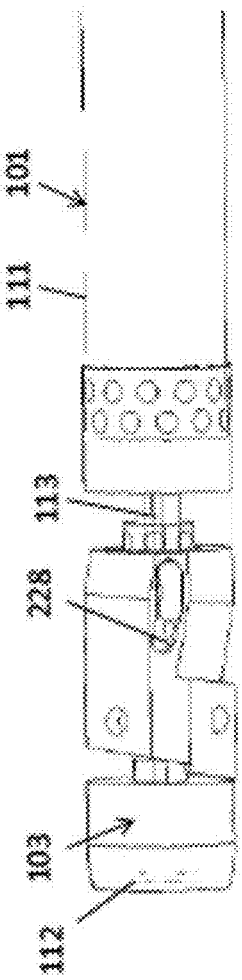
Figure 4D:
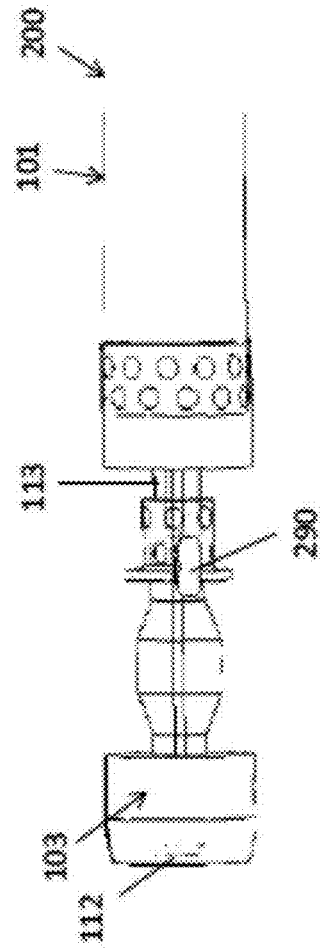

As shown in FIG. 3, the atherectomy catheter 100 (or 200 or 400) can further include a mechanism for packing tissue into the nosecone, such as by moving the drive shaft axially. In one embodiment, movement of the drive shaft 113 distally closes the nosecone 105. Moving the drive shaft 113 further distally will move the cutter 103 into a passive position (i.e., against a distal edge of the window 107) where the cutter 103 can be protected by the edge of the window 107 to avoid undesired cutting of the vessel during use. Moving the drive shaft 113 further distally will move the cutter 103 into the nosecone 105, thus packing tissue with a distal face of the cutter 103, as shown in FIG. 3. The cutter 103 can move more than 0.5 inches, such as more than 1 inch or more than 2 inches into the nosecone 105 to pack the tissue. In some embodiments, the nosecone 105 is formed of a material that is OCT translucent (e.g., non-metallic) so that panoramic OCT images can be taken therethrough.

Figure 14B:
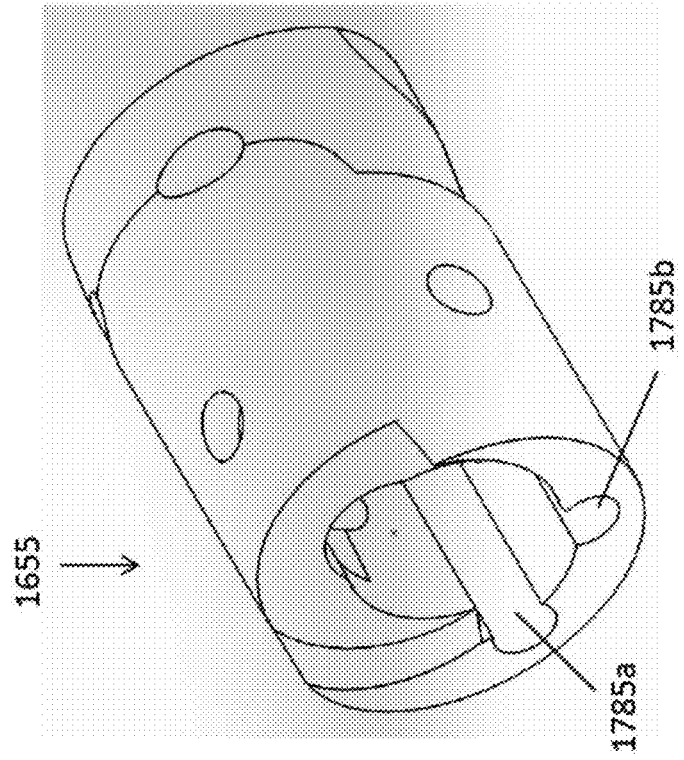
FIGS. 14A and 14B show a bushing having jet channels therethrough to assist in packing of tissue into the nosecone of an atherectomy catheter.
Figure 14A:
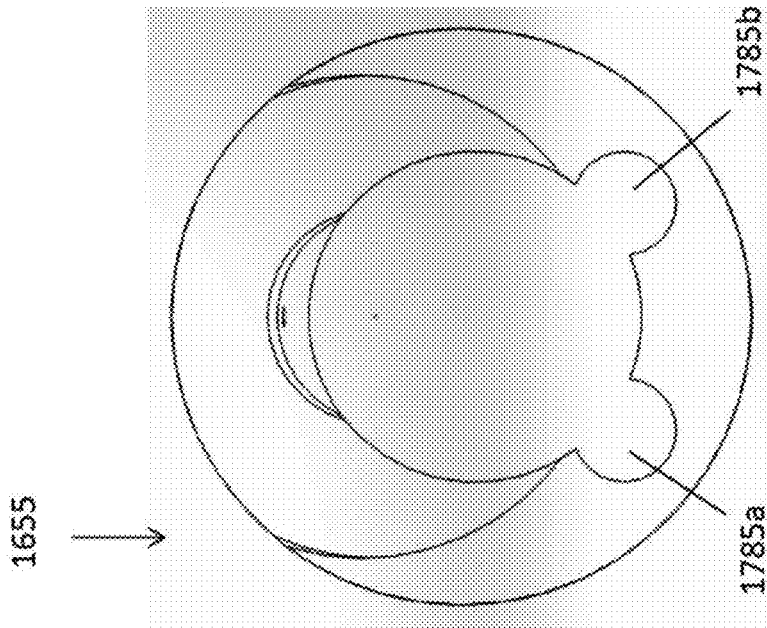

Referring to FIGS. 14A-14B, in some embodiment a bushing 1655 can include all of the features of the bushings described above, but can additionally include jet channels 1785a,b cut into the inner circumference thereof and extending from the proximal end to the distal end. The jet channels 1785a,b can connect a fluid line within the elongate body 101 to the nosecone 105. Fluid flowing through the jet channels 1785a, b can increase speed and thus provide enough force to pack cut material into the nosecone and clear the imaging region within the nosecone. Further, the jet channels can create a venturi effect at the distal end of the bushing 1655, which can suck material into the nosecone and/or away from the imaging/cutting head and/or the distal end region of the elongate body.

In one embodiment, the atherectomy catheter 100 (or 200 or 400) includes a guidewire lumen in the nosecone 105, such as a monorail, for use in guiding the catheter. Advantageously, the guidewire lumen can be used as a marker during imaging.

In some embodiments of atherectomy catheters 100, 200, or 400, there can be one or more small imaging windows 207, 307 in the nosecone 105 opposite to the cutting window 107, as shown in FIGS. 1A and 2A-2C. These additional imaging windows 207 can provide more of a 180 degree view during imaging. Further, one set of windows 207 can be more proximal and configured to be axially aligned with the cutter 103 and the imaging element 192 when the nosecone is opened while the other set of windows 307 can be more distal and configured to be axially aligned with the cutter 103 and the imaging element 192 when the nosecone is closed and the cutter 103 is in the passive position. In some embodiments, the imaging windows 307, 207 have different shapes from one another to further help identify cutter position in the resulting OCT images.

Referring to FIGS. 8A-11B, the OCT image catheter with the device will vary depending upon the placement of the imaging device in the three different configurations (nosecone open, nosecone closed with cutter in cutting position, nosecone closed with cutter in packing position). Accordingly, a user can identify, simply by looking at the imaging display, whether the nosecone 105 is displaced and whether the cutter 103 is in the cutting or packing position.

For example, FIG. 8A shows a panoramic image 800 of a surrounding vessel when the cutter 103 (and, correspondingly, the imaging sensor) is in the cutting position, as shown in FIG. 8B. The wall of the nosecone 105 is displayed as the circular feature 808 in the image 800. Further, because the nosecone 105 is made of a clear material, the vessel tissue 806 can be imaged even through the nosecone 105. As can be seen in image 800, a 180 degree view of the tissue 806 can thus be obtained. The circular artifact 803 in the image (and here, the radial line 801) correspond to a guidewire and/or guidewire channel running alongside the nosecone 105.

In contrast to image 800, FIG. 9A shows a panoramic image 900 of a surrounding vessel when the cutter 103 is in the passive position and the nosecone 105 is closed, as shown in FIG. 9B. A 180 degree view of the vessel tissue 906 is shown on the right side of the image (taken through window 107) while the closed nosecone 909 is shown on the left side of the image (the lines 909a,b correspond to the bushing wall). The space 913 between the lines 909a,b through which tissue 906 can be seen on the left side of the image is taken through the additional window 307 in the bushing. Further, the distance between the arrows in image 900 indicates that the distal tip is "closed" (and close therefore close to the midline of the catheter).

Figure 10A:
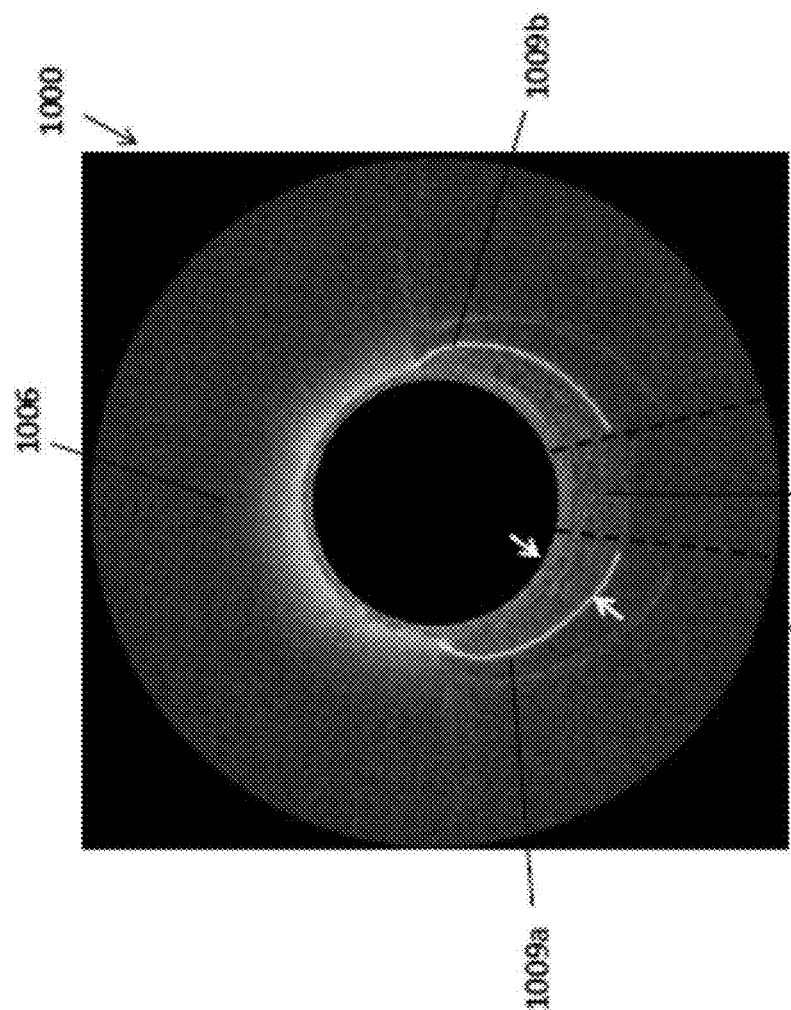
FIG. 10A shows a panoramic OCT image of a blood vessel taken with an atherectomy catheter through cutting window(s) when the nosecone is open, as identified by the arrow in FIG. 10B.
Figure 10B:
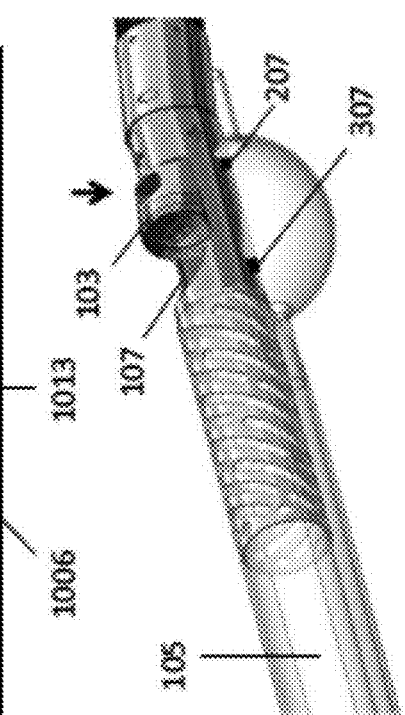

Finally, in contrast to image 900, FIG. 10A shows a panoramic image 1000 of a surrounding vessel when the cutter 103 is in the cutting position and the nosecone 105 is open, as shown in FIG. 10B. The vessel tissue 1006 (taken through window 107) is shown on the right side of the image while the closed nosecone 1009 is shown on the left side of the image (the lines 1009a,b correspond to the bushing wall). The space 1013 between the lines 1009a,b through which tissue 1006 can be seen is taken through the window 207. A comparison of the relative distance between the arrows in FIGS. 9A and 10A shows an increased distance between the catheter body and the nosecone, thereby suggesting to the operator that the nosecone 105 is in an open position. Further, in some embodiments, when the nosecone is open or closed, the image resulting from the window 207/307 will look different due to the angle change between the windows 207/307 and the imaging element 297 and/or the different shape of the windows 207/307.

In one embodiment, the atherectomy catheter 100 (or 200 or 400) includes a flush port close to the cutter 103. The flush port can be used to deliver flushing fluid to the region of imaging, thereby improving image quality. In some embodiments, the flushing can be activated through a mechanism on the handle of the device. The fluid can, for example, be flushed in the annular space between the catheter body 101 and the driveshaft 113. Further, in embodiments with jet channels in the bushing, the annular space can connect to the jet channels to provide fluid thereto.

Figure 6:
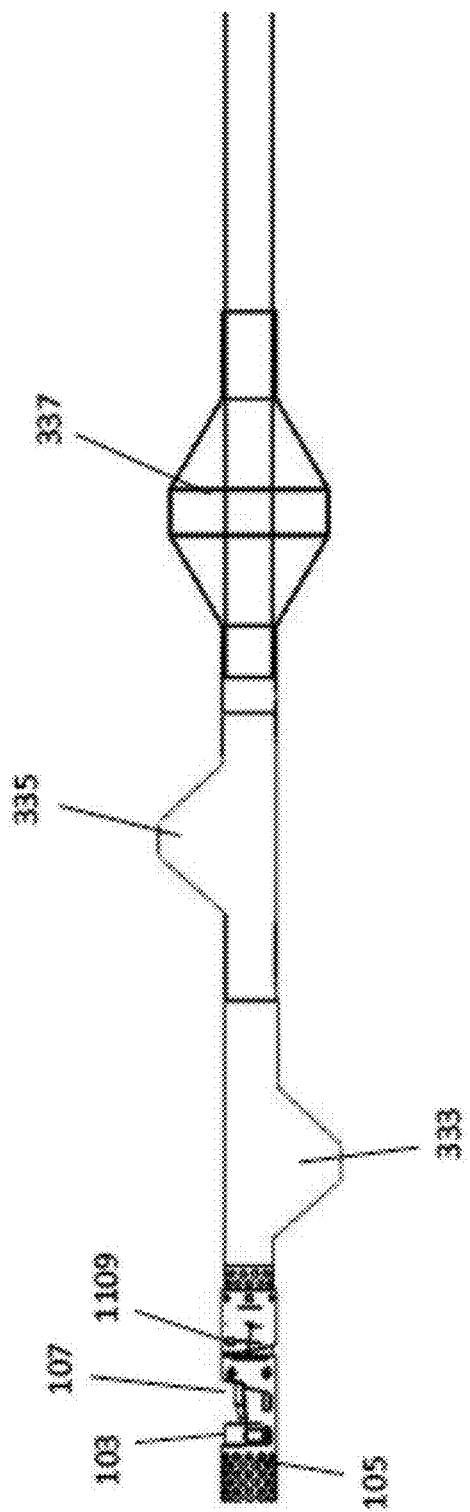
FIG. 6 shows one variation of a distal end of an atherectomy having a plurality of balloons that are arranged and may be used to provide a mechanical advantage in driving the cutting edge against the vessel wall.
Figure 7B:
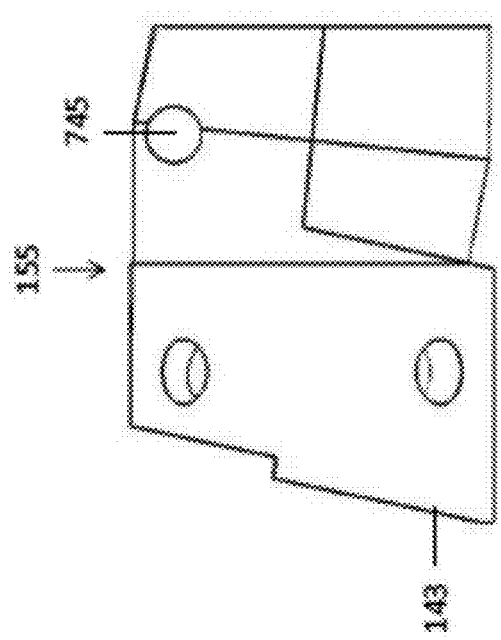
FIGS. 7A-7D show perspective, side, top and front views, respectively of a bushing for an atherectomy device.
Figure 7D:
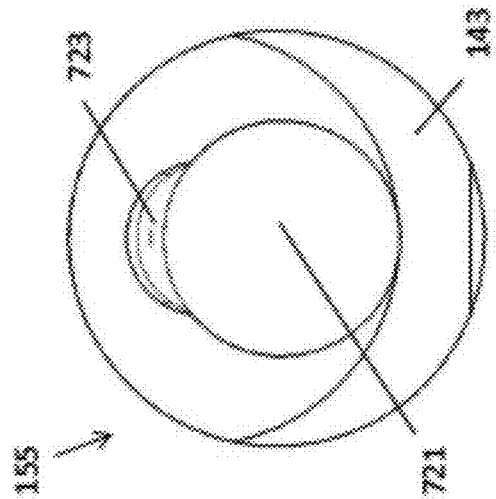
Figure 7A:
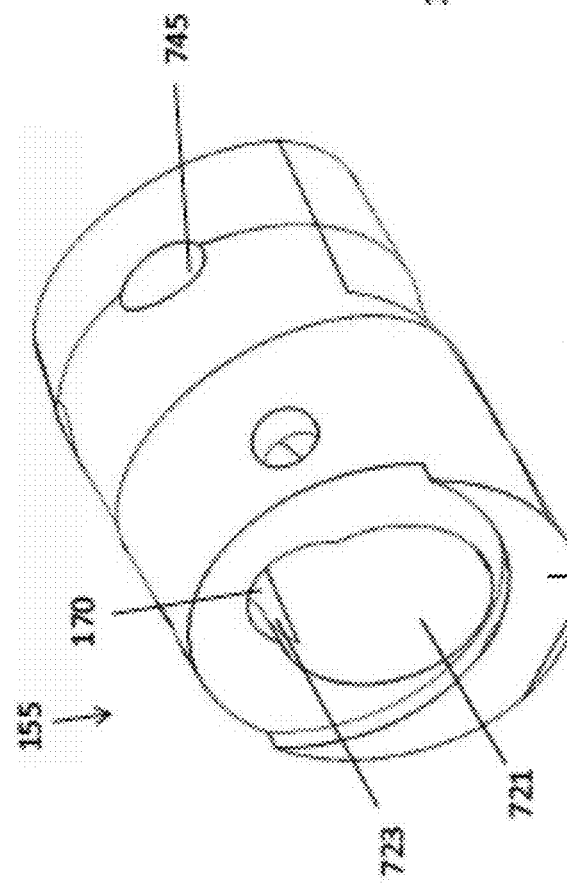
Figure 7C:
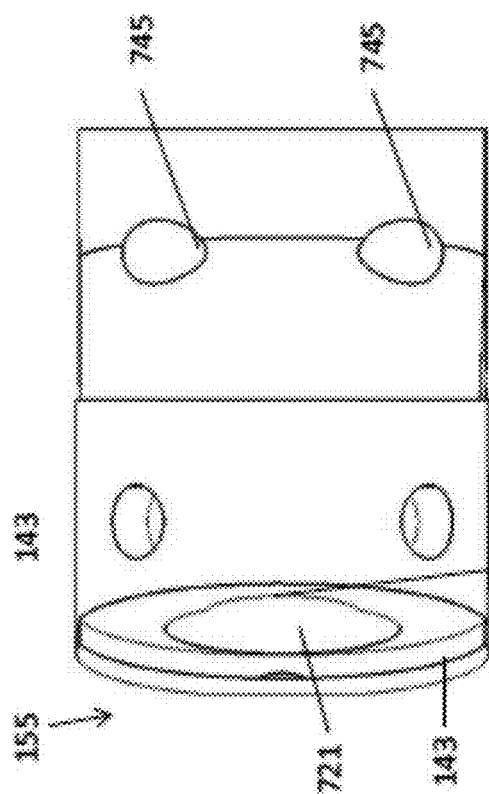

Referring to FIG. 6, in some embodiments, the atherectomy catheters 100, 200, 400 can further include two or more balloons configured to help urge the cutter 103 into the tissue. The first balloon 333 can be the distal-most balloon. The first balloon 333 can be positioned proximate to the hinge point 1109 and opposite to the cutting window 1107. The balloon 333 can urge the cutter 103 against the tissue by deflecting the cutter 103 up and into the tissue. A second balloon 335, proximal to the distal balloon 333, can be on the same side of the catheter 100 as the cutting window 107 and can further help drive the cutter 103 into the tissue by. In some embodiments, the second balloon 335 can be annular. In some embodiments, the second balloon 335 can help occlude the vessel. Further, in some embodiments (and as shown in FIG. 6), a third balloon 337 can be used for occlusion. One or more of the balloons 333, 335, 337 can be configured to as to expand with little pressure, such as less than 2 psi. This low pressure advantageously prevents the balloons 333, 335, 337 from pushing hard against the vessel wall, but still provides enough pressure to urge the cutter 103 into the tissue. The balloons 333, 335, 337 can further include tapered edges on the proximal and distal edges that allow the balloon to slide along the vessel and/or fit through tortuous regions.

Figure 15:
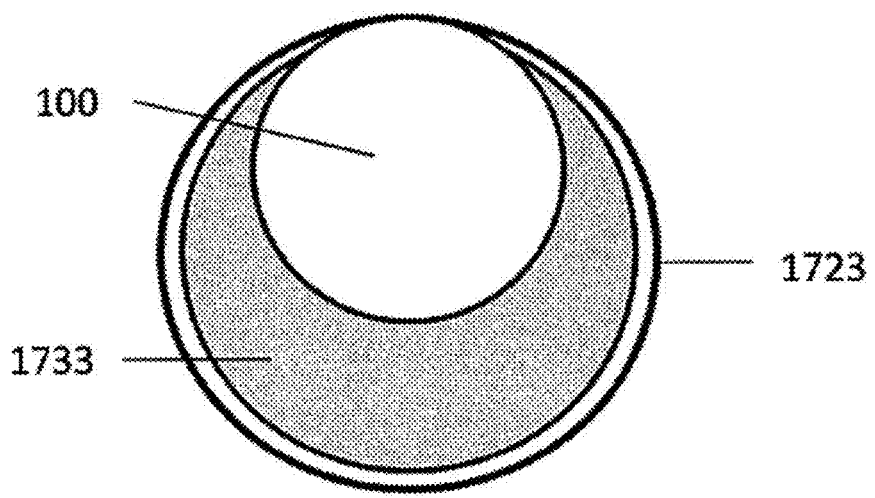
FIG. 15 shows a cross-section of an atherectomy catheter with a crescent-shaped balloon.
Figure 16A:
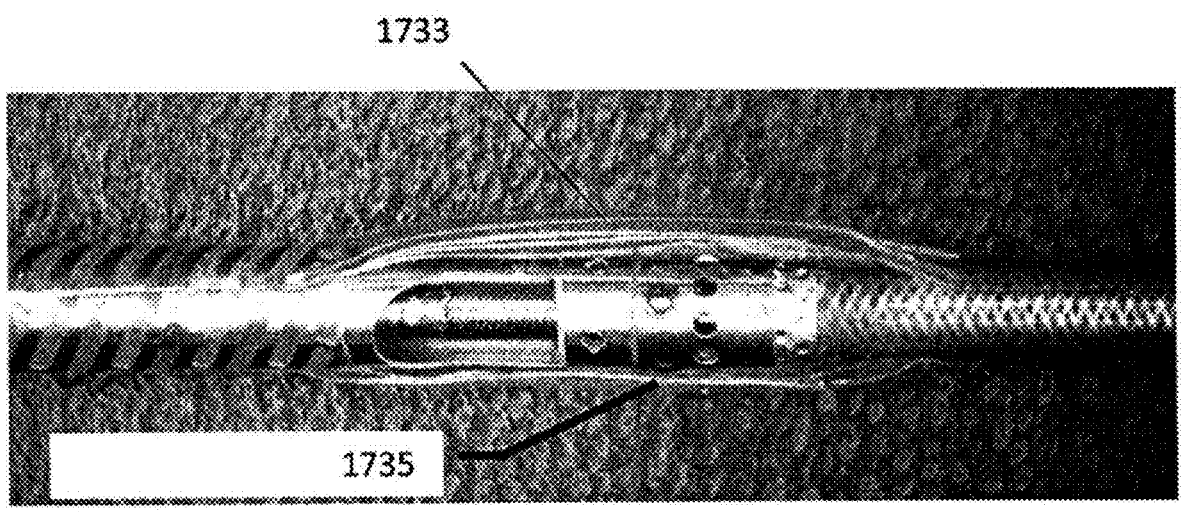

Referring to FIGS. 15 and 16A-16C, in another embodiment, the atherectomy catheters 100, 200, 400 can include a single balloon configured to both urge the cutter 103 into the tissue and occlude blood flow to improve imaging. Referring to FIG. 15, the balloon 1733 can have a crescent shape, i.e., can be wrapped around the catheter 100 so as to cover the entire circumference of the catheter 100 except where the cutter 103 is exposed. By using a balloon 1733 with such a shape, the gaps between the catheter 100 and the vessel 1723 are substantially reduced, advantageously negating or reducing the localized flushing required to displace blood from the visual field. In one embodiment, to create the crescent shape, the balloon includes wide necks at both ends that are then wrapped around the nosecone 105 and elongate body 101 such that they cover at least half of the circumferential surface. FIG. 16A shows the wrapped balloon edges 1735 while FIG. 16B shows the wide necks 1737 fused at both ends. FIG. 16C shows an inflation port 1739 contained inside the balloon 1733 as well as a guidewire lumen 1741 that spans the length of the balloon 1733. In some embodiments, the balloon 1733 can be used to open or close the nosecone without requiring proximal or distal movement of the driveshaft.

Figure 5:
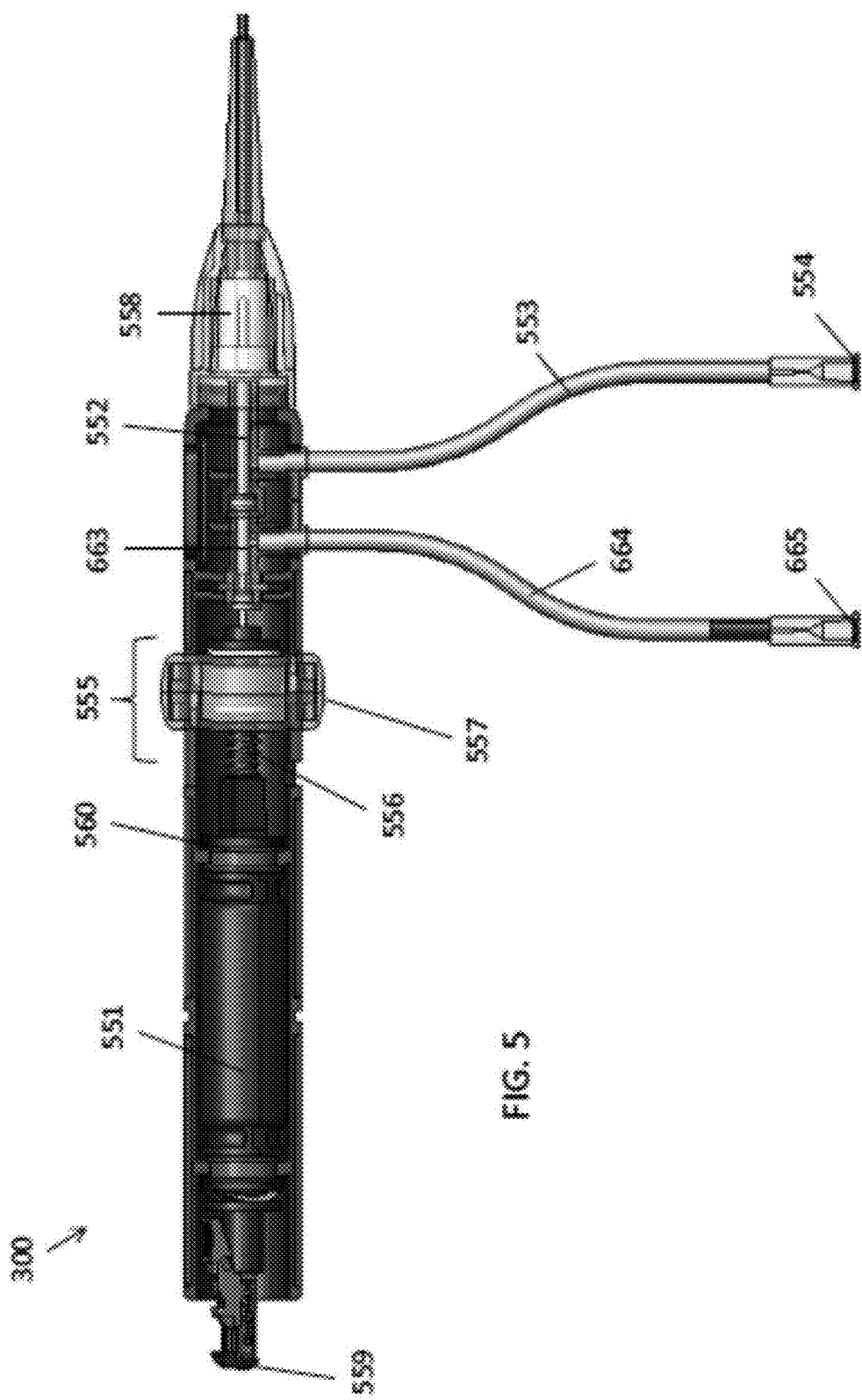
FIG. 5 illustrates a handle for an atherectomy catheter.

Referring to FIG. 5, a handle 300 can be used to control the rotation or translation of the driveshaft for the catheter 100, 200, or 400. The handle 300 can advantageously allow the optical fiber to move distally and proximally with the cutter as it is driven without requiring the fiber to move at a proximal location, e.g., without requiring movement of the optical fiber assembly within the drive assembly. Thus, the handle 300 can be design to completely account for movement of the drive shaft. An exemplary driveshaft management system 555 is shown in FIG. 5. The driveshaft management system 555 allows the user to position the driveshaft distally or proximally as the driveshaft is simultaneously spinning at a high speed. In some embodiments, the driveshaft can be configured such that it is fully tensioned before the driveshaft management system 555 is positioned at its most proximal position. That is, the driveshaft management system 555 can include a driveshaft tensioning spring 556. The spring 556 can be configured such that, as the user positions the slideable user ring 557 (or button) proximally, the driveshaft is fully tensioned and the driveshaft management system 555 is moved proximally, causing the spring 556 to compress and apply a controlled tensile load on the driveshaft. This fiber management system 555 advantageously enhances performance of the catheter by tensioning the driveshaft with a pre-determined load to properly position the cutting and imaging component against the bushing at the distal end of the catheter, improving cutting and imaging of the catheter.

The driveshaft management system 555 can transmit torque originating from a drive assembly, as described further below. Connection to the drive assembly can be made at the optical connector 559. Torque can thus be transmitted from the optical connector 559, through the fiber cradle 551, to the drive key 560, through the driveshaft management system 555, and then directly to the catheter driveshaft, all of which can rotate in conjunction. The fiber cradle 551 can include a set of components (i.e., a pair of pieces to make the whole fiber cradle) that houses the proximal end of the optical fiber and transmits torque within the driveshaft system. The fiber cradle components can be thin-walled by design, thereby creating a hollow space inside. Within this hollow space of the fiber cradle 551, the optical fiber can be inserted or withdrawn as the device driveshaft is positioned proximally or distally. As the fiber is inserted into the fiber cradle 551 when the user ring 557 is positioned proximally, the fiber is able to coil within the internal space of the fiber cradle 551 while maintaining imaging throughout its length to the distal tip. Conversely, as the fiber is withdrawn from the fiber cradle 551 when the user ring 557 is positioned distally, the coiled section of fiber is able to straighten while maintaining imaging throughout its length to the distal tip. This design feature advantageously provides more fiber capacity or "slack" to the overall driveshaft system to increase the range in which the driveshaft system can be translated.

The handle 300 can further include a balloon inflation chamber 552 configured to connect to a balloon inflation lumen (e.g., for use with a balloon on the catheter as described above) on one side and to balloon inflation tubing 553 and/or a port 554 on the other side. Because the inflation fluid transfers to the balloon through the balloon inflation chamber 552, the outer shaft 111 can advantageously rotate (e.g., by rotating the knob 558) independently of the balloon inflation chamber 552, allowing the tubing 553 and/or port 554 to remain stationary during rotation of the outer shaft 111.

Moreover, as shown in FIG. 5, the handle 300 can further include a catheter flush chamber 663 and catheter flush tubing 664 and/or flush port 665 to provide flushing through the catheter, as described above.

Any of the atherectomy catheters described above can be used with a cutter having a serrated distal edge designed to remove calcified and hard fibrous disease in an artery. The calcified and hard fibrous disease can be difficult to remove due to its increased hardness compared to plaque. While a standard cutter may have no problem debulking the majority of arterial plaque, in certain instances, the plaque encountered by an atherectomy catheter may be harder and/or of a greater volume than what is typically encountered. This may be due to plaque having a larger percentage of calcium, fibrin, and other cellular waste relative to the percentage of fat and cholesterol. A serrated or scalloped cutter with a serrated cutting edge can facilitate cutting and breaking away calcified and fibrous disease. The serrated edge can advantageously initiate the cut into the calcium by utilizing a large force over a small area, thereby providing the greatest cut efficiency to engage and cut the hardened disease.

FIGS. 17A-17B show an exemplary atherectomy catheter 1700 with a serrated cutter 1703. The catheter 1700 includes a catheter body 1701 and a nosecone 1705 hinged to the catheter body 1701 at an off-axis hinge point 1709. As in other embodiments, the nosecone 1709 can be configured to collect tissue therein. In some embodiments, the cutter 1703 can be moved distally to pack tissue into the nosecone. When the nosecone 1705 is deflected, the serrated cutting edge 1710 of the cutter 1703 can be pushed into the tissue. A balloon 1733, when inflated, can also aid in moving the cutting edge 1710 towards the tissue.

FIGS. 18A-31E and 42A-42F illustrate various embodiments of serrated cutters that can be used, for example, with atherectomy catheter 1700, to break down calcified and hard fibrous disease in the artery. The serrated cutting edge can spin at a high speed with various serrated geometries configured to engage hard calcified and fibrous disease in the diseased arteries.

Figure 18E:
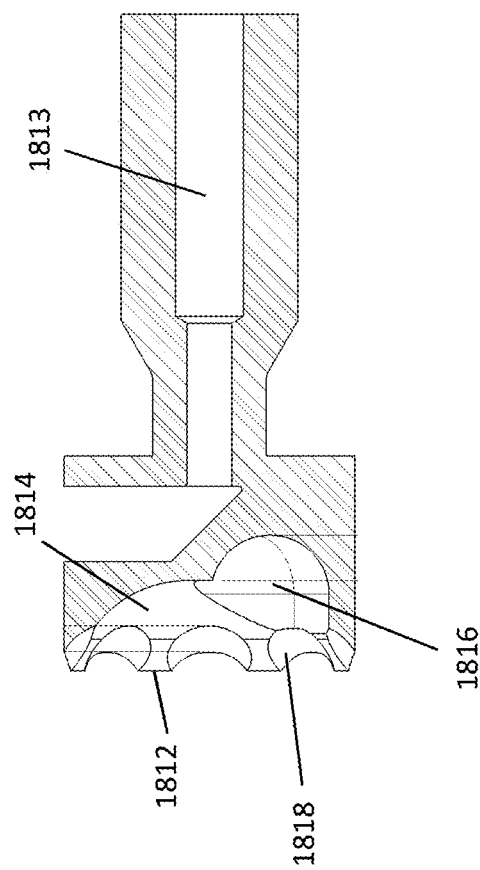
Figure 19B:
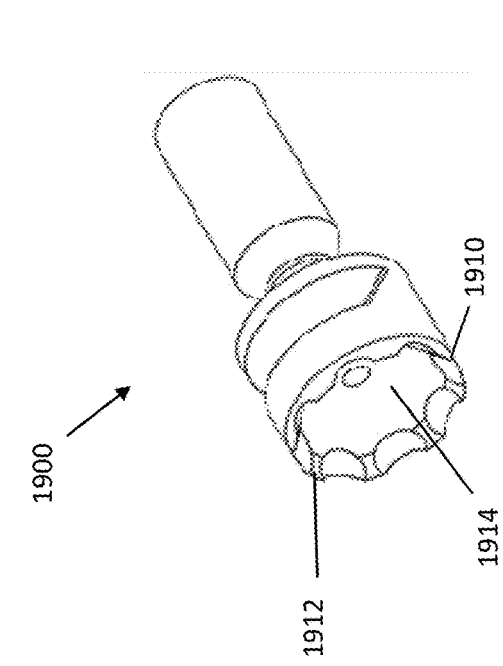
FIGS. 19A-19E show an atherectomy catheter cutter having a serrated cutting edge and a symmetric pocket within the cutter body.
Figure 19D:
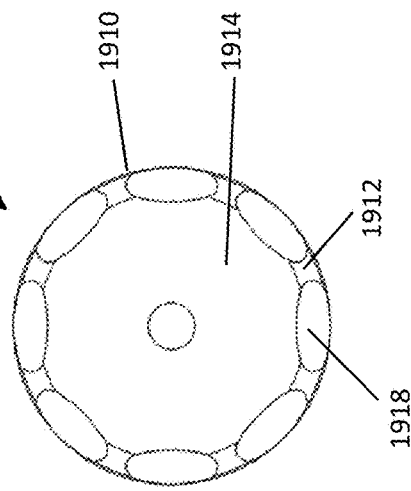
Figure 19A:
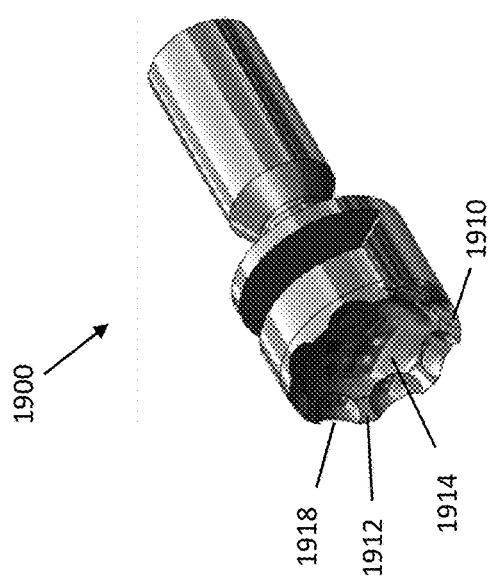
Figure 19C:
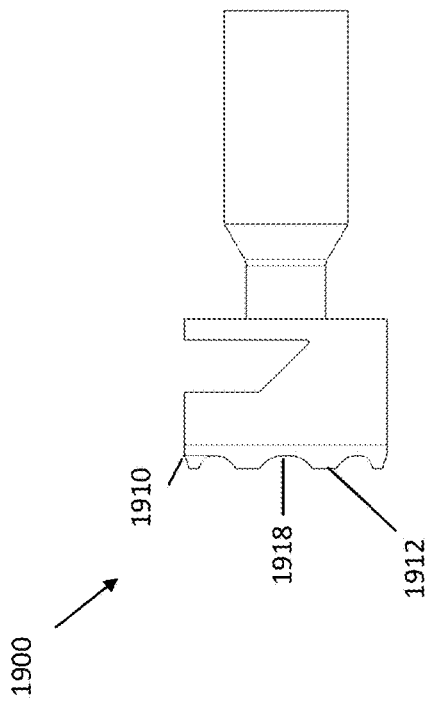
Figure 19E:
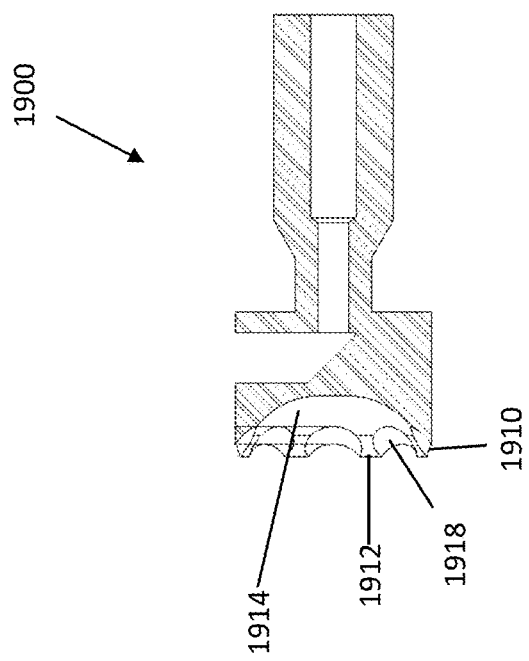

FIGS. 18A-18E show a first variation of a serrated cutter 1800 designed for removing calcified plaque. As FIGS. 18A-18E show, the serrated cutter 1800 has a proximal end 1802 and a distal end 1804. The proximal end 1802 is attachable to drive shaft of an atherectomy catheter. The distal end 1804 includes a cutting edge 1810 along the circumference of the serrated cutter 1800 that includes teeth 1812. The teeth 1812 create saw-like serrations along the edge 1810 that are configured to cut into calcified tissue. Thus, as the cutter 1800 is rotated, the teeth 1812 of the cutting edge 1810 contribute to better purchase and grabbing of calcified deposits for breakage and/or removal of the deposits. FIG. 18E shows the cross-sectional side view of the cutter 1800 attached to a driveshaft 1813.

The serrated cutter 1800 also includes a symmetric and concave or recessed bowl 1814 extending radially inwards from the cutting edge 1810 to the central axis of the cutter 1800. Further contained within the bowl region is an asymmetric cavity 1816 (i.e., extending off of a central axis of the cutter 1800). The asymmetric cavity 1816 covers between ⅓ and ½ of the surface area of the bowl region 1814 of cutter 1800. The asymmetric cavity 1816, as shown in FIG. 18D, includes three regions that further aid with breaking up of the harder forms of plaque. Further, seams 1815 delineate the three regions of the asymmetric cavity 1816 may protrude slightly above the surface of the asymmetric cavity 1816 walls, where the seams 1815 may be sharp or may include grabbing features that further aid with gripping onto and breaking apart calcified plaque deposits. It is also conceivable that the asymmetric cavity includes greater or less than three regions. As the cutter 1800 is rotated, the asymmetric cavity 1816 advantageously breaks up the calcium plaque within the bowl 1814 as the off-axis sidewalls and/or seams hit the rigid pieces within the bowl 1814, advantageously avoiding having the calcified plaque fold back onto itself (which can cause stalling of the cutter).

Each tooth 1812 of the cutter 1800 borders a grinding segment 1818. The grinding segments 1818 are depressions or scoops in the bowl 1814 that have a greater curvature than the bowl 1814. The grinding segments 1818 have a concave curvature at the distal end 1804 of the cutter 1800 (as seen in FIGS. 18C and 18E). The grinding segments 1818 of the serrated cutter 1800 are largely semi-circular in shape and disposed equidistantly about the perimeter of cutter 1800. The grinding segments 1818 can have sharp edges or points therearound that are configured to grind, sever, and/or grab onto the calcified plaque by applying more pinpointed force to the calcified plaque encountered while the cutter is rotating. In other variations, the grinding segments 1818 disposed about the circumference of cutter 1800 may be otherwise shaped (e.g. square or rectangular cut outs, triangular cut outs, symmetric, asymmetric, and so forth). Further, the grinding segments 1818 can be either equidistantly disposed about the cutter perimeter or can be more unevenly or non-uniformly disposed about the cutter perimeter.

FIGS. 19A-19E shows drawing of a second variation of a serrated cutter 1900 designed for removing calcified plaque deposits. The serrated cutter 1900 shown in FIGS. 19A-19E possess many of the same features as the cutter 1800 shown in FIGS. 18A-18D, such as a serrated cutting edge 1910 having teeth 1912 and half-circular grinding segment 1918s disposed evenly along the circumference of the cutting edge 1910. Similar to the design shown in FIGS. 18A-18E, the grinding segments 1918 can be depressions within the bowl 1914 that are disposed along the perimeter of the cutter 1910. The grinding segments 1918 can aid with grabbing and grinding into calcified plaque as the cutter rotates and are able to impart targeted force on the calcified plaque encountered and more easily break off the harder plaque formations. The bowl 1914 is symmetric and recessed in essentially in the shape of a half sphere for accommodating larger plaque formations. In some variations, the bowl region 1914 may also include additional features that can further aid with grabbing and breaking apart calcified plaque as the cutter rotates. Additional features may include protrusions, or cavities about its sidewalls that are either symmetrically or asymmetrically distributed along the wall. The protrusions may have a sharp edge or point while the cavity may have a sharp edge, where these features aid with gaining purchase of the calcified plaque during the procedure. There may also be features at the base of the bowl that aid with gripping and purchase while the serrated cutter is rotating.

Figure 20B:
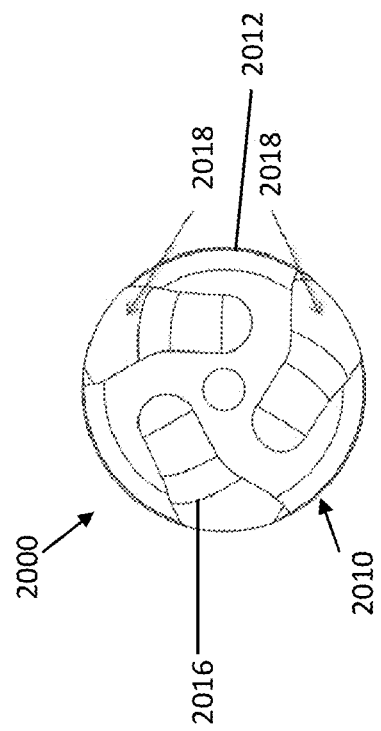
FIGS. 20A-20E show an atherectomy catheter cutter having rotationally asymmetric depressions therein.
Figure 20D:
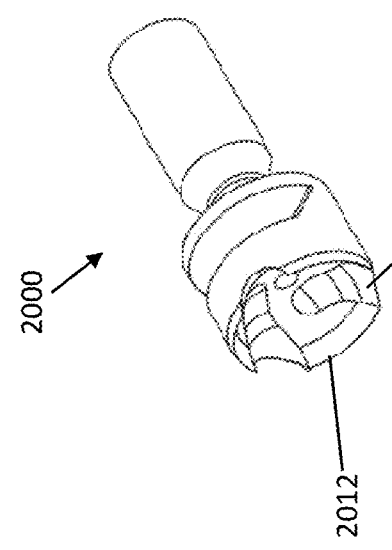
Figure 20A:
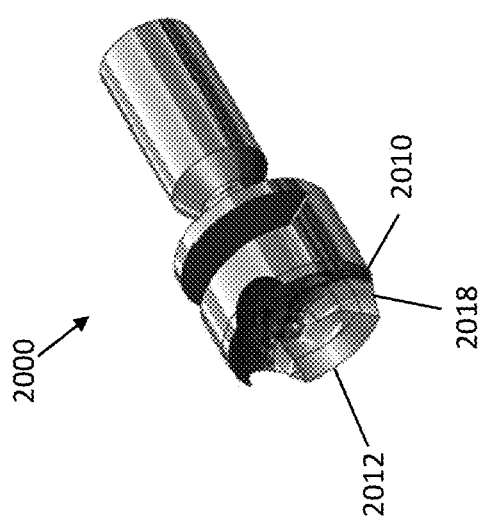
Figure 20C:
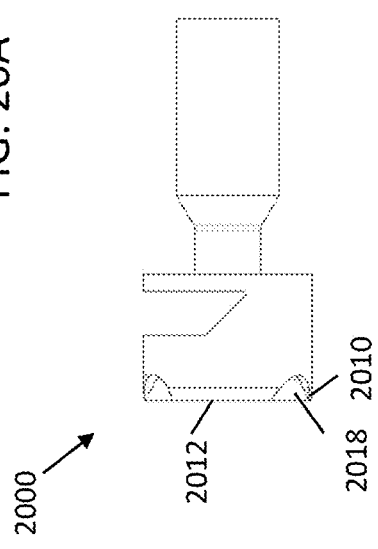
Figure 20E:
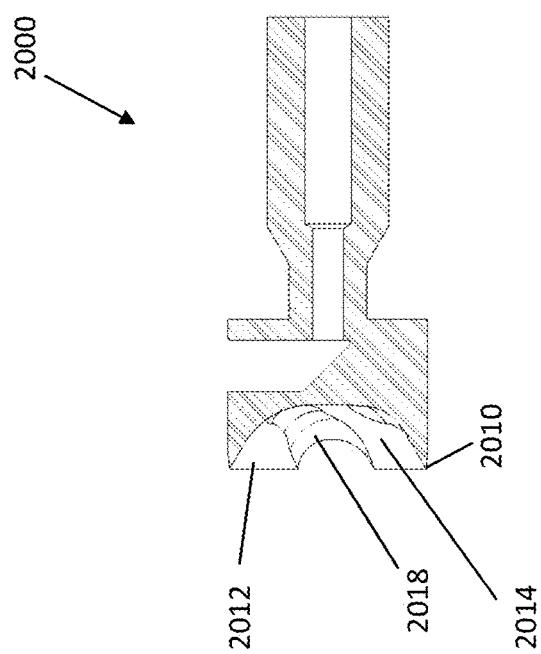
Figure 21E:
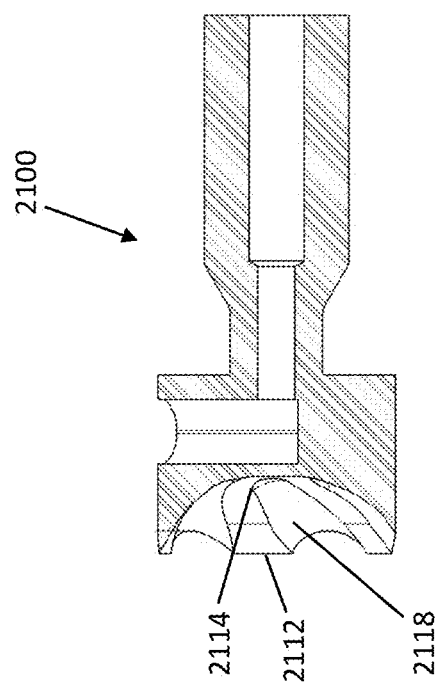

Another variation of a serrated cutter 2000 for easier debulking of calcified plaque is shown in FIGS. 20A-20E. The serrated cutter 2000 includes a bowl region 2014 having a serrated cutting edge 2010 disposed along its perimeter. The cutting edge 2010 includes a plurality of teeth 2012 extending therearound with a plurality of grinding segments 2018 therebetween. The grinding segments 2018 can form a deeper scooped portion along the serrated edge 2010. The grinding segments 1218 can extend radially inwards towards and past the center of the bowl 2014 in an off-axis or spiraled manner. While the scooped grinding segments 2018 are shown in FIG. 20D in a symmetric pattern, as the cutter 2000 rotates, the scooped regions 2018 creates rotational asymmetry within the bowl region 2014 that allows the walls of the grinding segments 2018 to grab onto the plaque and scoop the plaque out and break the plaque up. The combination of the teeth 2012 and the off-axis scoop cuts of the grinding segments 2018 provide enhanced cutting and grinding of calcified plaque as the cutter 2000 rotates. The teeth 2012 and/or grinding segments 2018 may further include edges or seams 2016 that are raised with respect to the surface of the scooped regions 2018 to further aid with gripping the calcified plaque during use. Furthermore, the bowl 2014 and/or the off-axis scooped regions may also include other gripping texture or features that are able to further enhance the purchase of the cutter on plaque deposits encountered during use of the cutter.

FIGS. 21A-21E show another variation of a serrated cutter 2100 that is well-suited for debulking calcified plaque. Serrated cutter 2100 also includes a serrated cutting edge 2110 along the circumference of cutter 2100. Serrated cutter 2100 also includes a bowl region 2114. Cutter 2100 further includes a series of teeth 2112 and a series of scooped out grinding regions 2118 that each begin at the cutting edge 2114 and extend inward towards the center of the bowl region 2114. The edge of the scooped out region 2118 correspond to concave portions along the perimeter of the cutting edge 2110. As the cutter rotates, the teeth 2112 and the scooped grinding segments 2118 aid greatly with gaining purchase of the calcified regions and providing targeted force onto the calcified plaque. In this example, the series of scooped grinding segments 2118 are arranged in a helical patter within bowl region 2114. The helical cutting pattern 2118 can advantageous help grab onto plaque and cut the plaque when the cutter is rotating. Cutter 2100 may also include additional features 2116 within the bowl 2114 that increase the cutter's gripping ability while in use.

Figure 22B:
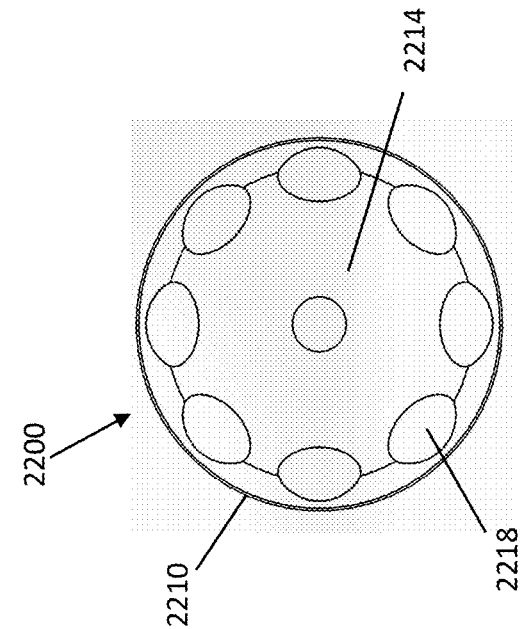
FIGS. 22A-22B show an atherectomy catheter cutter having a smooth cutting edge having a series of pockets disposed within a bowl region.
Figure 22A:
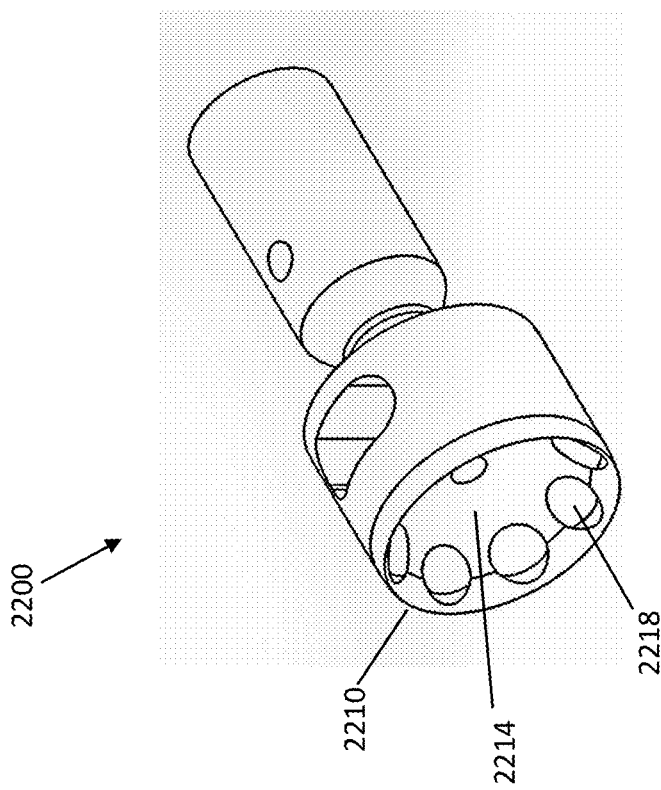

FIGS. 22A and 22B show a cutter 2200 having no serration along the outer circumference. The cutter 2200, similar to the other cutters already described, includes a bowl region 2214. The cutter 2200 has a cutting edge 2210 along its outer perimeter. The cutting edge 2210 is smooth and continuous. Rather than having serrations, cutter 2200 has a series of breaker pockets or grinding segments 2218 distributed along an inner circumference of the bowl region 2214. Each grinding segment 2218 includes a cavity (having a greater curvature than the bowl 2214) for aiding in gripping onto hardened plaque and serve to break up and debulk calcified plaque encountered. The grinding segments 2218 can be in the shape of a circle or an oval. The intersection between the grinding segments 2218 and the areas of the bowl regions 2214 may possess sharpened edges that further aid with gripping and breaking up of hardened plaque. As the cutter 2200 rotates, the grinding segments 2218 can aid with further crushing of the plaque formations and sending these broken down plaque into the nosecone region. While the grinding segments shown in FIGS. 22A and 22B are symmetric and evenly distributed within the bowl region, in some embodiments, the breaker pockets may be asymmetric in shape and may not all be of the same size.

Figure 23B:
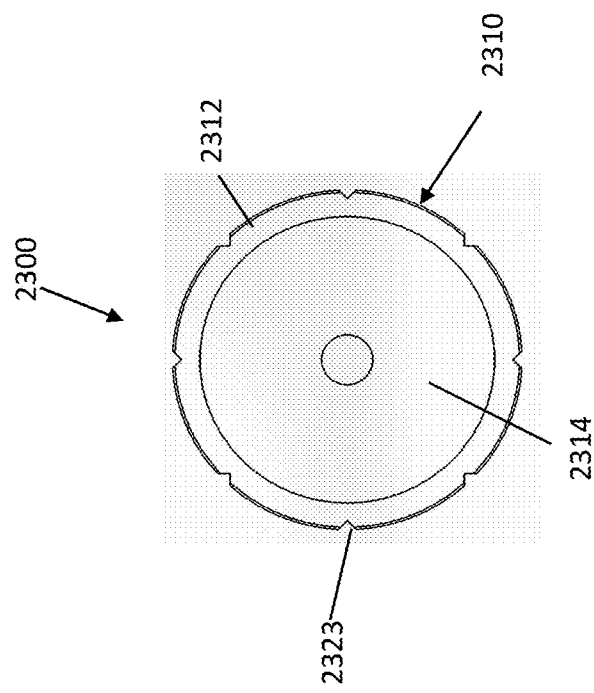
FIGS. 23A-23B show an atherectomy catheter cutter having grooved cutting edges disposed on the outer rim of a bowl region, where the grooves also extend along the outer wall of the cutter.
Figure 23A:
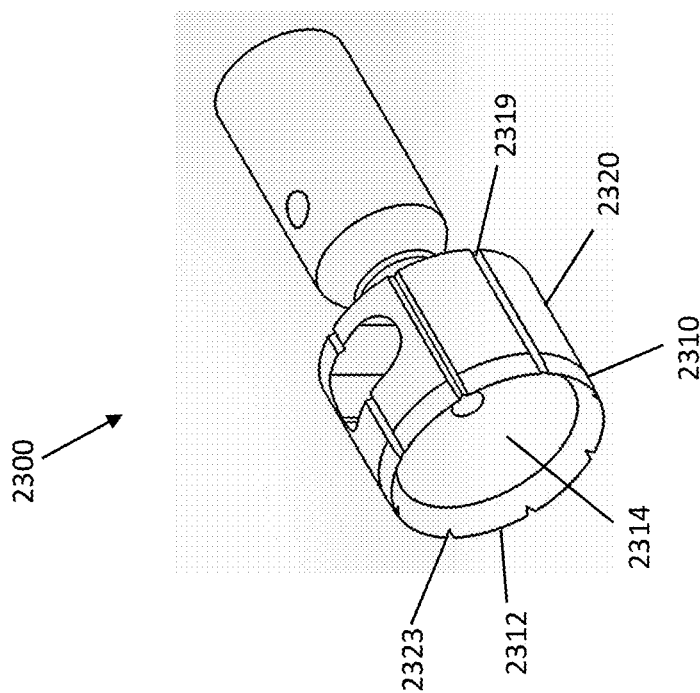

In some instances, hydraulic pressure may be present due to the tight fit between the major, outer diameter of the cutter and the inner diameter of the catheter's nosecone. Turning to FIGS. 23A and 23B, cutter 2300 includes features that may be able to alleviate some or all of the hydraulic pressure. Like many of the cutters previously discussed, the cutter 2300 includes a bowl region 2314 and a serrated cutting edge 2310 disposed therearound. Here, the teeth 2312 are separated by V-shaped grooves 2323 distributed around the perimeter of the bowl region 2314. Further, the V-shaped grooves 2323 of cutter 2300 may extend along an outer wall 2320 of cutter 2300 such that where the V-shaped grooves 2318 occur, corresponding V-shaped channels 2319 extend from the V-shaped groove 2323 along the entire length of cutter 2300's outer wall. The V-shaped channels 2319 spaced around the outer wall of cutter 2300 serve to relieve any hydraulic pressure that may be generated in the nose cone when the cutter is slid forward deeper into the nosecone and subsequently when the cutter is drawn back during rotation of the cutter.

Figure 24B:
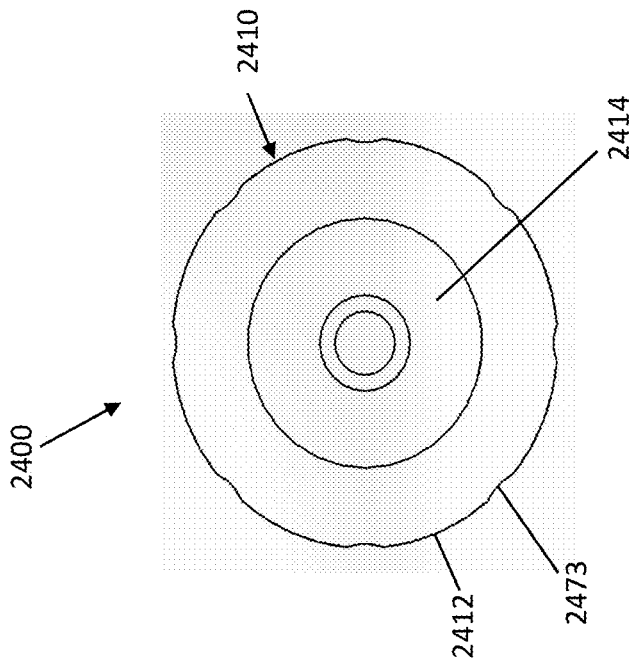
FIGS. 24A-24B show an atherectomy catheter cutter having shallow cutouts in the cutting edge disposed on the outer rim of a bowl region. The shallow cutouts also extend along the outer wall of the cutter.
Figure 24A:
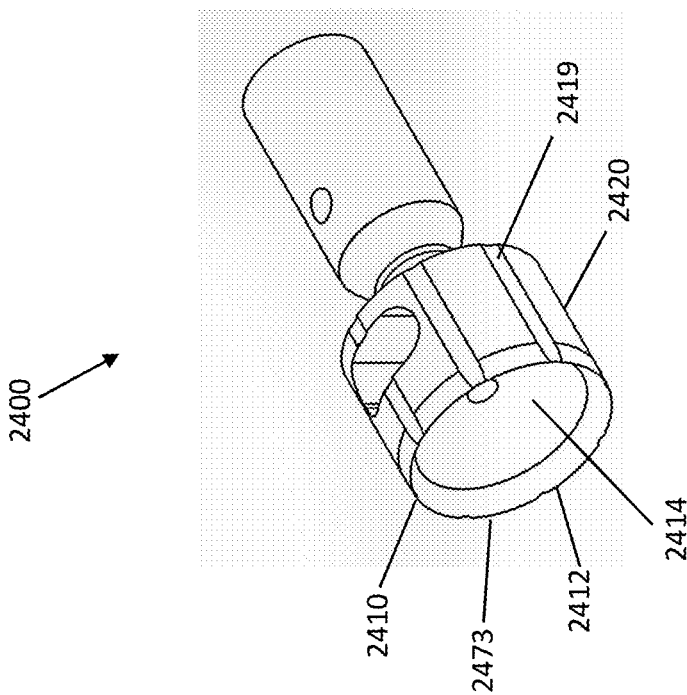

Turning to FIGS. 24A and 24B, a cutter 2400 is shown. The cutter 2400 includes a bowl region 2414 and a serrated cutting edge 2410 disposed along the perimeter of the bowl region 2414. The serrated cutting edge 2410 includes a plurality of teeth 2412 separated by shallow cutouts 2423 in the cutting edge 2410. In this variation of the cutter, the shallow cutouts 2423 extend along an outer wall 2420 of the cutter 2400 to form a rounded channels 2419 that are disposed on the outer wall 2420 of the cutter 2400. The rounded channels 2419, similar to the V-shaped channels 2319 described earlier, can serve to relieve hydraulic pressure that may build up while the rotating cutter is pushed into the nosecone of the catheter.

Figure 25B:
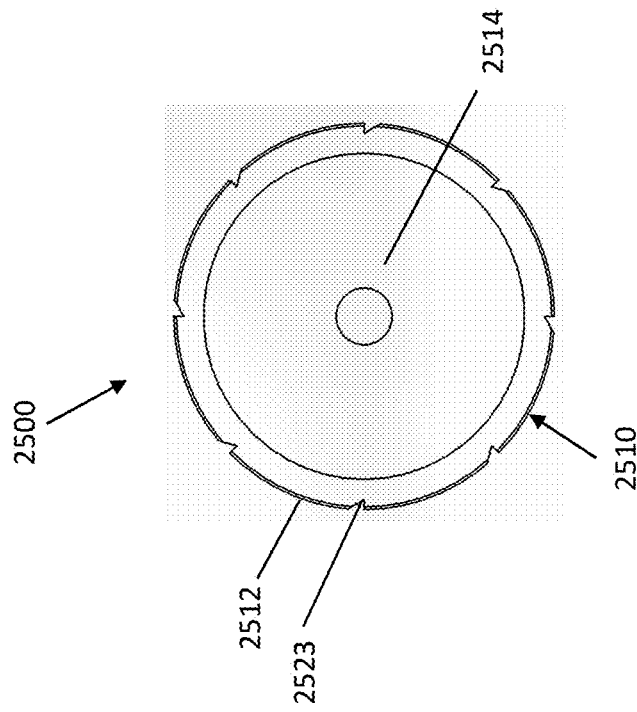
FIGS. 25A-25B show an atherectomy catheter cutter having asymmetric grooves in the cutting edge disposed on the outer rim of a bowl region. The asymmetric groove also extends along the outer wall of the cutter.
Figure 25A:
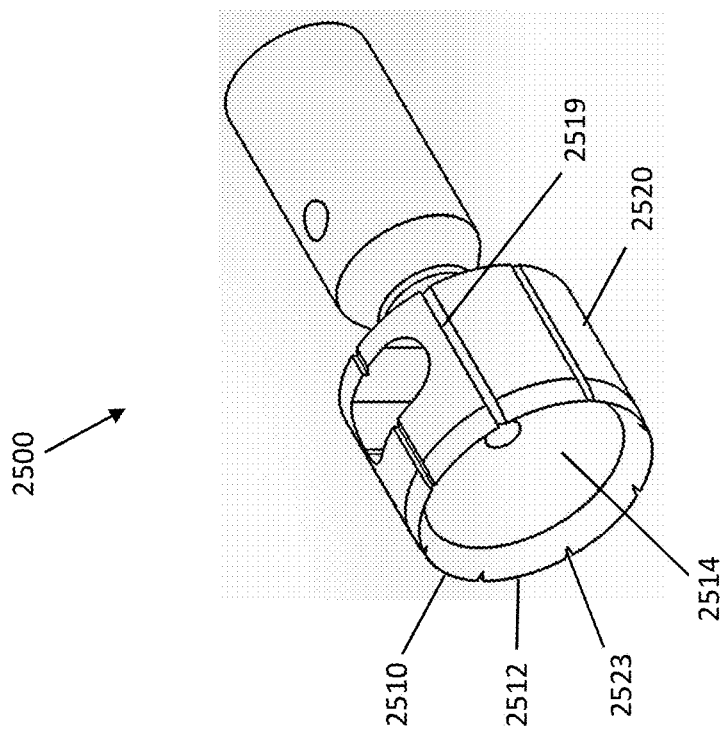

FIGS. 25A and 25B shows a cutter 2500, another variation of cutter designs that include grooves along the outer wall of the cutter. Here, the cutter 2500 includes a bowl region 2514 and a serrated cutting edge 2510 disposed along the perimeter of the bowl region 2514. The cutting edge 2510 is formed by teeth 2510 separated by v-shaped recesses 2512. The v-shaped recesses 2523 are asymmetric such that the channels 2519 that are formed from the asymmetric recessed regions 2512 and that extend along an outer wall 2520 of the cutter 2500 are also asymmetric in nature. An advantage of having asymmetric grooves disposed along the outer wall of the cutter is that there is less likelihood that the groove edges from catching on the inner diameter of the nosecone as the cutter is rotating.

Figure 26B:
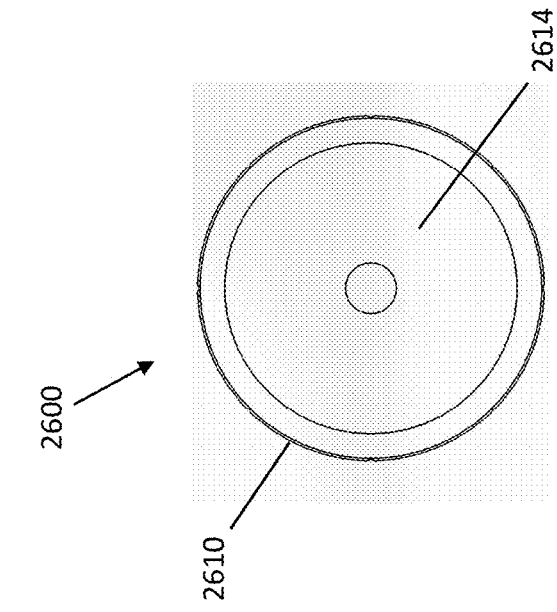
FIGS. 26A-26B show an atherectomy catheter cutter having a smooth cutting edge disposed around a bowl region of the cutter, where the outer wall of the cutter includes a series of grooves.
Figure 26A:
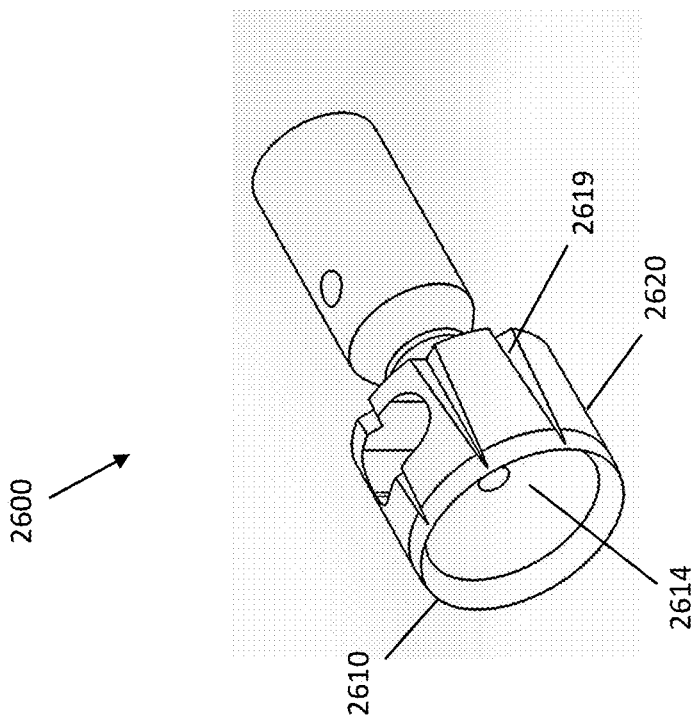

Another variation of a cutter 2600 is shown in FIGS. 26A and 26B. The cutter 2600 includes a bowl region 2614 and a cutting edge 2610 disposed along the perimeter of the bowl region 2614. Here, the cutting edge 2610 has a smooth cutting surface about the outer perimeter of the bowl region 2614. The cutter 2600 further includes angled channels 2619 disposed around the outer wall 2620 of the cutter 2600. The angled channels 2619 preserves the smooth cutting edge 2610 by originating on the outer wall 2620 of the cutter 2600 just below the cutting edge 2610 and extending away from the smooth cutting edge 2610. The cutter 2600 may be used in scenarios where the plaque encountered are not of the hardened and calcified variety and where a smooth cutting edge can successfully debulk the plaque encountered. The grooves arranged around the outer wall 2620 are able to minimize the buildup of hydraulic pressure when the cutter is pushed and subsequently pulled back from the catheter nosecone.

Figure 27B:
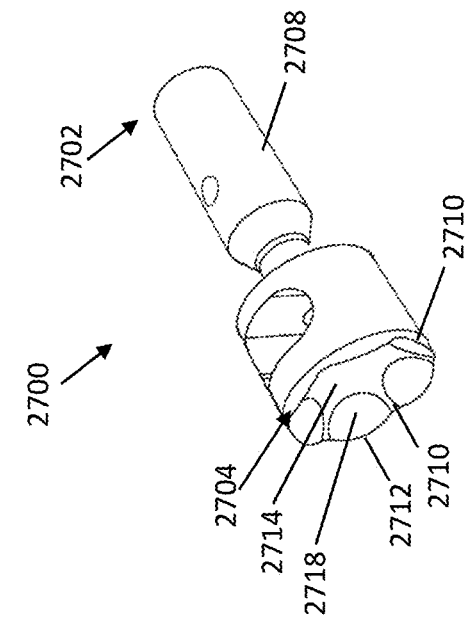
FIGS. 27A-27E illustrate an atherectomy catheter device including a cutter having a serrated annular cutting edge, a recessed bowl, and a plurality of segments according to one embodiment. Each of the segments is a flat facet having a concave portion on the cutting edge.
Figure 27D:
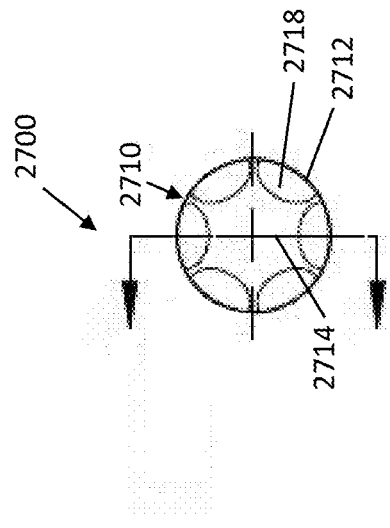
Figure 27A:
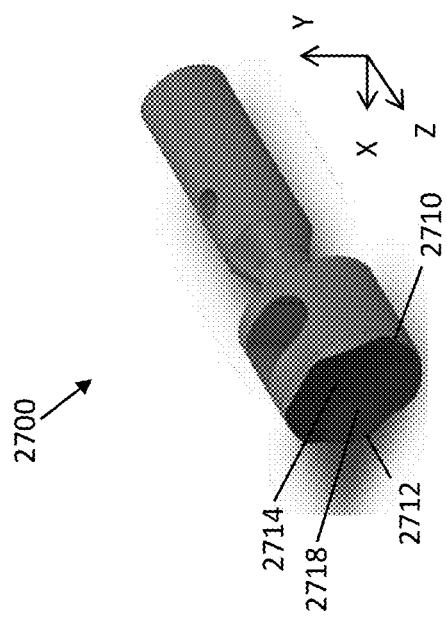
Figure 27C:
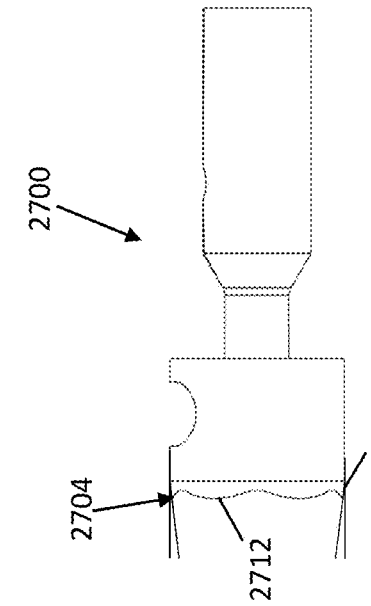
Figure 27E:
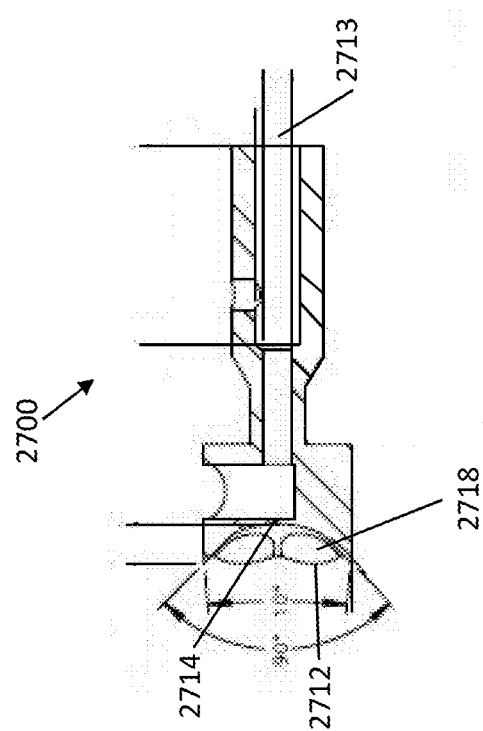

FIGS. 27A-27E illustrate another exemplary embodiment of a serrated cutter 2700 having a serrated annular cutting edge 2710, a recessed bowl 2714, and a plurality of grinding segments 2718. The cutter 2700 can include the recessed bowl 2714 extending radially inwards from the annular cutting edge 2710 to a center of the cutter 2700. The recessed bowl 2714 can extend radially inwards from the cutting edge 2710 with a converge angle. For example, the converge angle of the recessed bowl can be 90 degrees, as shown in FIG. 27E.

The cutter 2700 can further include a plurality of grinding segments 2718 or dimples within the bowl 2714 and extending radially inwardly from the cutting edge 2710. The plurality of segments 2718 can each have a substantially circular or ovoid shape. In some other embodiments, the plurality of segments 2718 may be otherwise shaped. Further, each of the plurality of segments 2718 can have a curvature that less than the curvature of the bowl 2714. As shown in FIGS. 27A-27D, each of the plurality of grinding segments 2718 can be a flat facet (i.e., such that the curvature is zero and the radius of curvature is infinite). The plurality of grinding segments 2718 can advantageously break the uniformity of the recessed bowl 2714, thus facilitating breaking hard substances such as calcium. The number of segments can be 2, 3, 4, 5, 6, 8, 12 or any number therebetween. For example, the cutter 2700 can have six grinding segments 2718 as shown in FIGS. 27A-27E. Further, the plurality of grinding segments 2718 can be either equidistantly disposed about the cutter perimeter or can be more unevenly or non-uniformly disposed about the cutter perimeter. The plurality of segments 2718 can be disposed symmetrically or unsymmetrically around the circumference of the cutting edge 2710.

As shown in FIGS. 27A-27E, each of the plurality of segments 2718 can form a convex tooth 2712 of the serrated annular cutting edge 2710. The convex teeth 2712 can be a portion of a circular shape or elliptical shape or other convex shape. The convex shaped teeth 2712 can be advantageous because there no sharp points are formed along a distal-most circumference of the cutting edge 2710. Since there is a constant force being applied along the arc from cutting tissues, the convex shaped portions are gentle in contact with tissue and have a long cutting length, thus engaging again tissue for a long time. The plurality of convex teeth 2712 can be configured to grind and grab onto the calcified plaque by applying pinpointed force to the calcified plaque encountered while the cutter is rotating.

As shown in FIG. 27C and FIG. 27E, the serrated annular cutting edge 2710 can angled radially inward relative an outer-most circumference of the cutter 2710 (and/or relative to the elongate body of the catheter to which it is attached). The outer side wall of the cutter edge 2710 on the distal tip 2704 can an angle α relative to a sidewall of the outermost circumference of the cutter 2700 (or of the attached catheter body) along a longitudinal direction. The angle α is advantageous such that the cutting edge 2710 does not cut through the nosecone itself. The angle α can be between 2 to 12 degrees in some embodiments. For example, the angle α can be 5 degrees. The distal tip 2704 of the serrated annular cutting edge 2710 can extend radially inward relative an outer diameter of the elongate body by 2 degrees to 12 degrees. The serrated annular cutting edge 2710 can angled radially and converged to a center axis of the cutter 2700 with a converge angle between 4 degrees and 20 degrees. For example, the converge angle can be 10 degrees in some embodiments as shown in FIG. 27E.

FIGS. 42A-42F show another exemplary embodiment of a serrated cutter 82700 designed for removing calcified plaque. Similar to the cutter 2700, serrated cutter 82700 has a proximal end 82702 configured to attach to a drive shaft of an atherectomy catheter and a distal end 82704, a serrated annular cutting edge 82710 along the circumference of the distal end 82704, a recessed bowl 82714, and a plurality of grinding segments 82718.

The cutter recessed bowl 82714 can extend radially inwards from the annular cutting edge 82710 to a center of the cutter 82700 at a converge angle α (see FIG. 42E). For example, the converge angle α of the recessed bowl can be between 80 and 100 degrees, such as 90 degrees.

The grinding segments 82718 can be positioned within the bowl 82714 and extend radially inwardly from the cutting edge 82710. The grinding segments 82718 can extend radially inwards relative to neighboring portions 82719 so as to form segments that break apart rigid pieces of tissue or plaque as the cutter 82700 spins. The segments 82718 can each have a least one inner edge 82728 that extends substantially straight from the cutting edge 82710 to the center of the cutter 82700. Thus, the segments 82718 can be squared, rectangular, or trapezoidal. The portions 82719 between the segments 82718 and radially outwards thereof can be, for example, triangular in shape. The plurality of segments 82718 can have the same shape as one another or can have different shapes (e.g., some rectangular and others trapezoidal). Further, the plurality of segments 82718 can extend distally to proximally part or all of the way along the recessed bowl 82714. For example, the plurality of segments can extend at least 50%, at least 60%, at least 70%, at least 80%, at least 90%, or substantially 100% distally to proximally along the bowl 82714 between annular cutting edge 82710 and the recessed flat section 82727. Each of the plurality of grinding segments 82718 can be a flat facet (i.e., such that the curvature is zero and the radius of curvature is infinite) or can have a curvature (have a "scooped out" configuration). Further, each of the plurality of segments 82718 can have a curvature that is less than the curvature of the bowl 82714. The plurality of grinding segments 82718 can advantageously break the uniformity of the recessed bowl 82714, thus facilitating breaking hard substances such as calcium. The bowl 82714 can have 2-16 grinding segments 82718 therein, such as 2, 3, 4, 5, 6, 8, or 12 grinding segments 82718. For example, the cutter 82700 can have six grinding segments 82718 as shown in FIG. 42D. Having fewer grinding segments may, for example, make the recessed bowl easier to manufacture while having more may better distribute the load as the cutter rotates and cuts material. Further, the plurality of grinding segments 82718 can be either equidistantly disposed about the cutter perimeter or can be more unevenly or non-uniformly disposed about the cutter perimeter. The plurality of segments 82718 can be disposed symmetrically or unsymmetrically around the circumference of the cutting edge 82710.

As shown in FIGS. 42A-42F, each of the plurality of segments 82718 can form a convex tooth 82712 of the serrated annular cutting edge 82710 while the neighboring portions 82719 therebetween can form a concave section 82721 therebetween. The convex teeth 82712 can be a portion of a circular shape or elliptical shape or other convex shape. The convex teeth 82712 and concave section 82721 can form an undulated or wavy cutting edge 82710 (e.g., by a continuous wave of scallops). The undulating cutting edge 82710 can be advantageous because there are no sharp points along a distal-most circumference of the cutting edge 82710, thereby allowing the edge 82710 to last longer without wearing down. Additionally, the entire undulating cutting edge 82710 can contact tissue as the cutter 82700 is rotated, thereby providing sharper cutting through the tissue or plaque. The proximal edge 82723 formed by the segments 82718 and neighboring portions can have a similar undulating shape.

The plurality of convex teeth 82712 and grinding segments 82718 can be configured to grind and grab onto the calcified plaque by applying pinpointed force to the calcified plaque encountered while the cutter is rotating.

As shown in FIG. 42F, the serrated annular cutting edge 82710 can be angled radially inward relative an outer-most circumference of the cutter 82710 (and/or relative to the elongate body of the catheter to which it is attached). The outer side wall of the cutter edge 82710 on the distal tip 82704 can extend inwards at an angle β relative to a sidewall of the outermost circumference of the cutter 82700 (or of the attached catheter body) along a longitudinal direction. The angle β is advantageous such that the cutting edge 82710 does not cut through the distal end of the catheter (e.g., the nosecone). The angle β can be between 2 to 12 degrees in some embodiments. For example, the angle β can be 5 degrees.

The recessed bowl 82714 can further including a flat (i.e., not curved) circular section 82727 at the proximal end of the recessed bowl thereof that is recessed relative to the proximal undulating edge 82723 formed by the grinding segments 82718 and neighboring portions 2719.

FIG. 28A-28E illustrate another embodiment of a serrated cutter 2800 having a serrated annular cutting edge 2810, a recessed bowl 2814, and a plurality of grinding segments 2818. The serrated annular cutting edge 2810 can have a plurality of teeth 2812. As shown in FIGS. 28A-28E, each of the plurality of segments 2818 can form concave edges between the teeth 2812 of the serrated annular cutting edge 2810. The curvature of the grinding segments 1818 can be greater than the curvature of the bowl 2814, thereby forming depressions or cavities in the bowl 2814. The number of segments can be 2, 3, 4, 5, 6, 8, 12 or any numbers therebetween. For example, the cutter 2800 can have seven recessed grinding segments 2818 as shown in FIGS. 28A-28E. Further, the plurality of grinding segments 2818 can be either equidistantly disposed about the cutter perimeter, as shown, or can be more unevenly or non-uniformly disposed about the cutter perimeter. The plurality of segments 2818 can be disposed symmetrically, as shown, or unsymmetrically around the circumference of the cutting edge 2810.

Figure 28E:
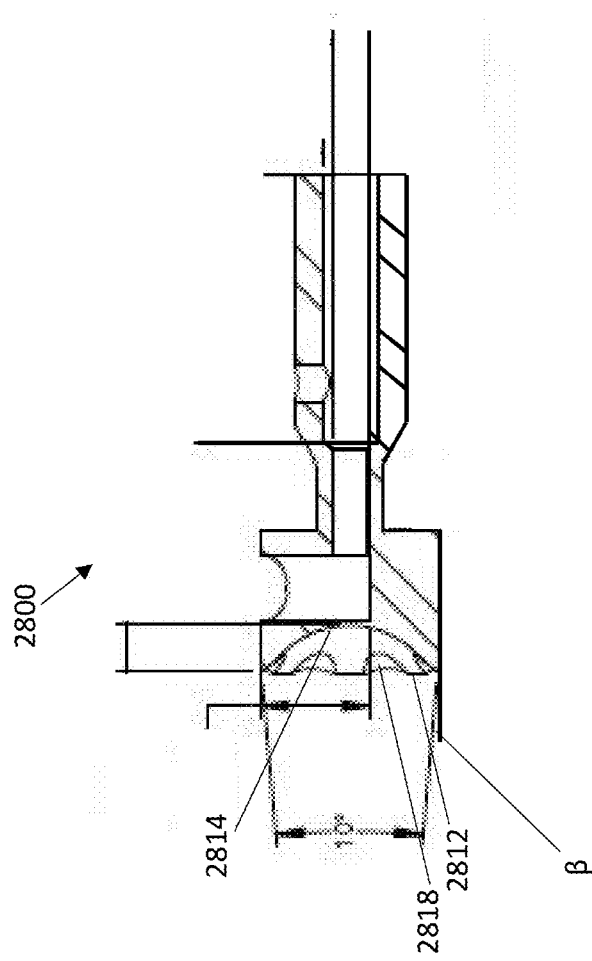
Figure 29E:
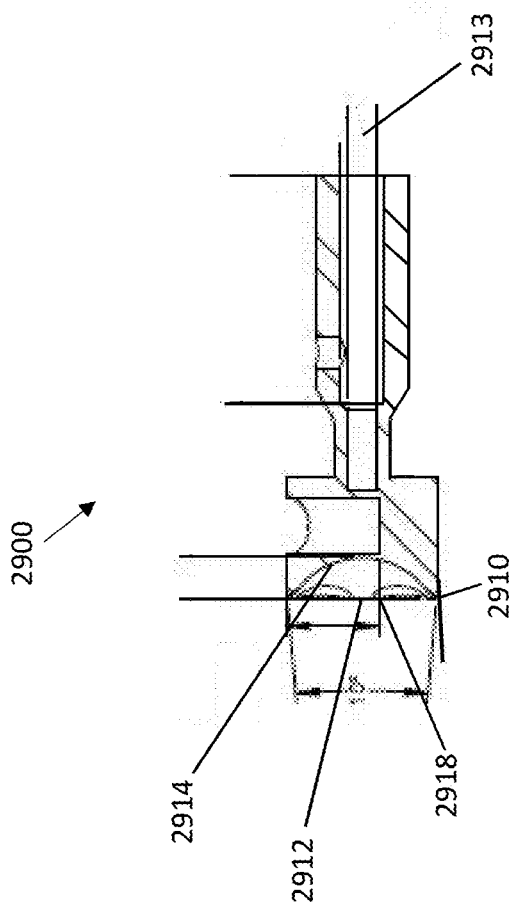
Figure 30B:
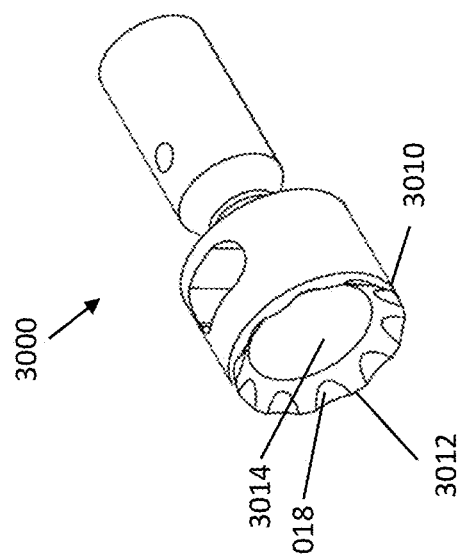
FIGS. 30A-30E illustrate an atherectomy catheter device including a cutter having a serrated annular cutting edge, a recessed bowl, and a plurality of segments according to one embodiment.
Figure 30D:
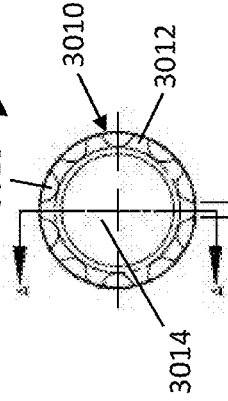
Figure 30A:
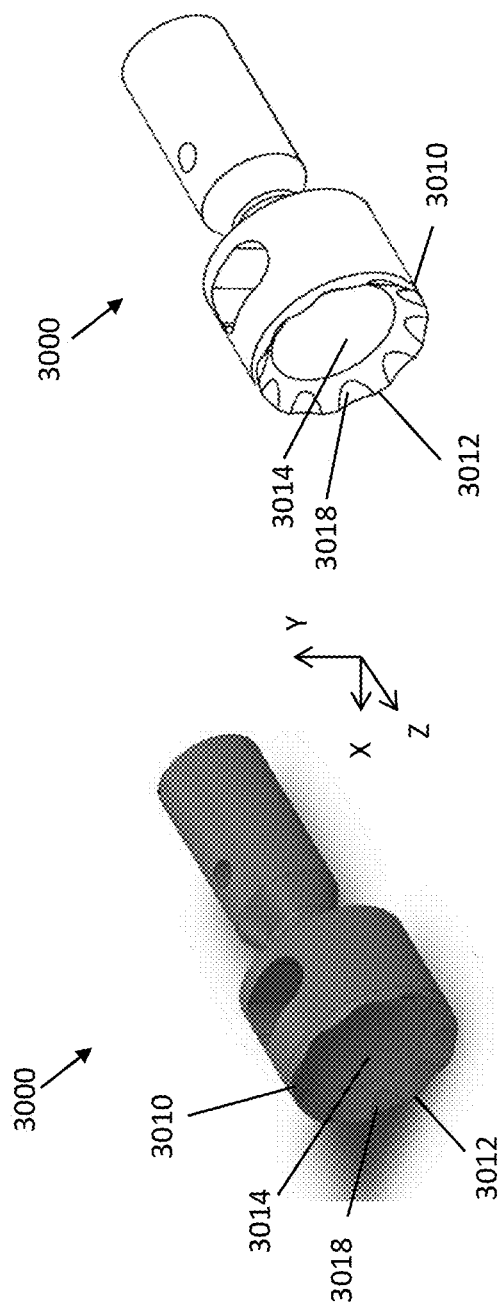
Figure 30C:
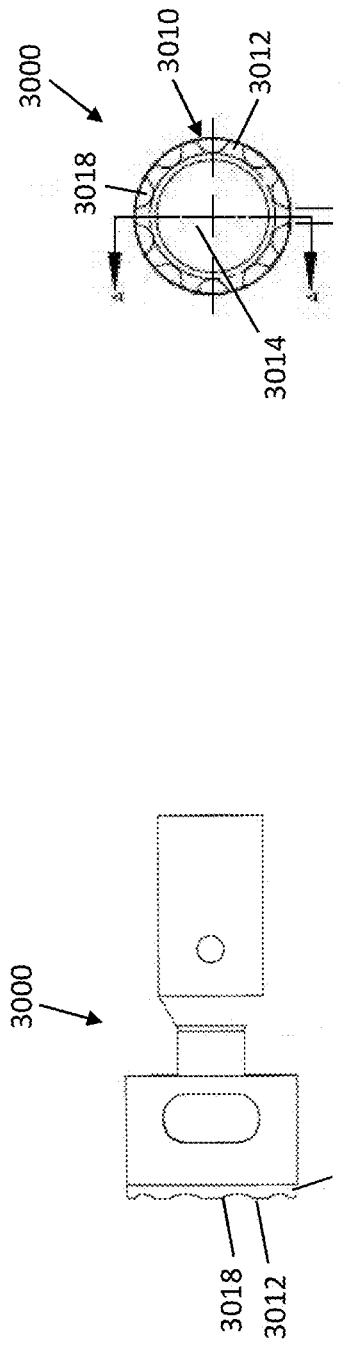
Figure 30E:
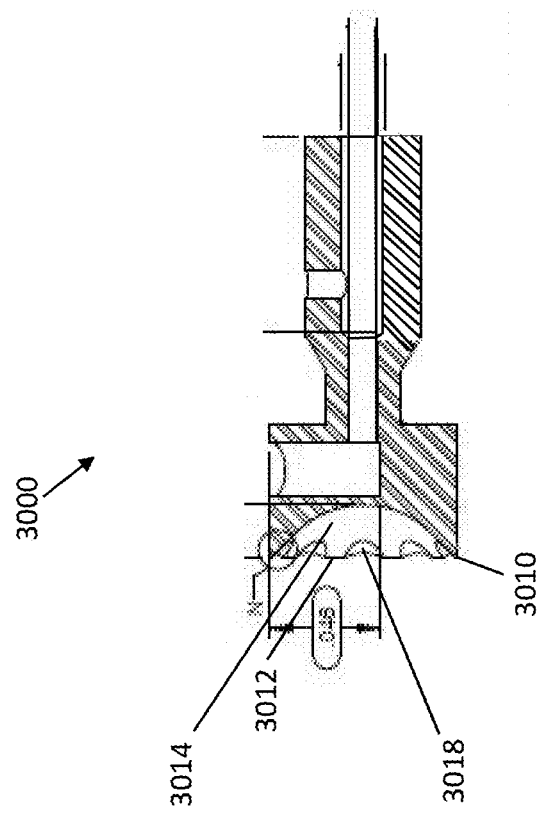
Figure 31B:
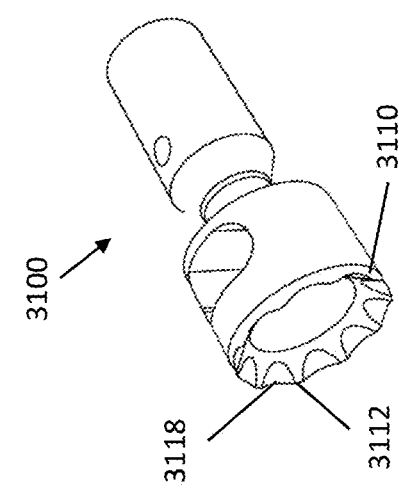
FIGS. 31A-31E illustrate an atherectomy catheter device including a cutter having a serrated annular cutting edge, a recessed bowl, and a plurality of segments according to one embodiment.
Figure 31D:
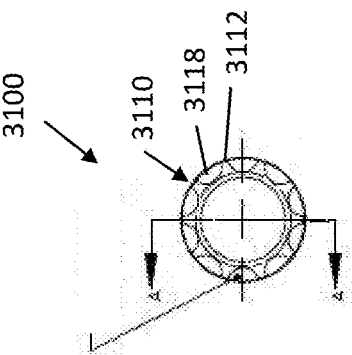
Figure 31A:
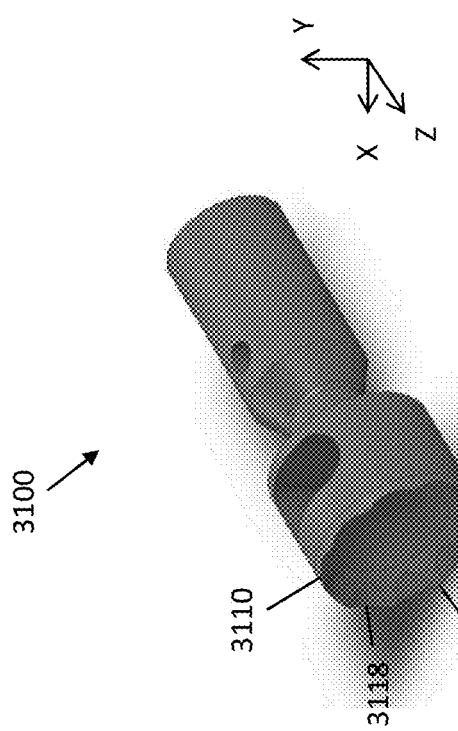
Figure 31C:
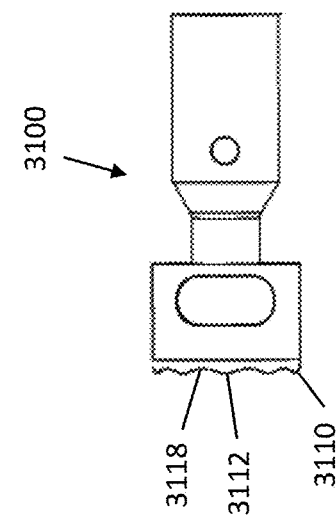
Figure 31E:
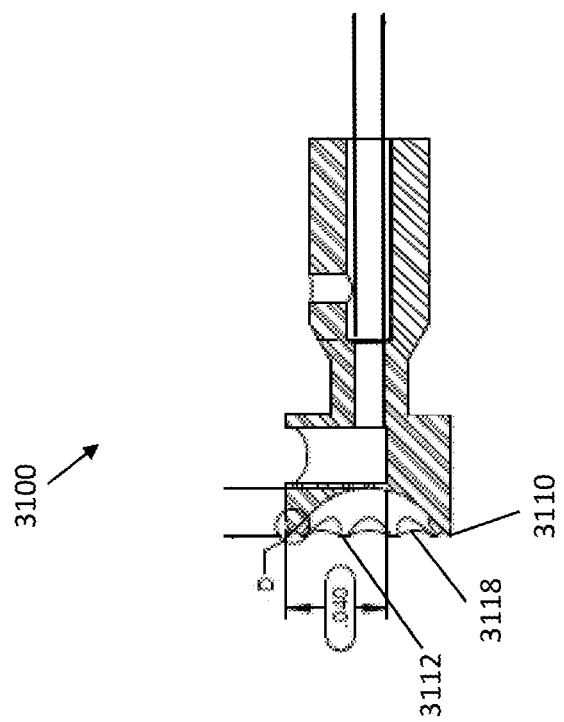

As shown in FIG. 28C, the serrated annular cutting edge 2810 can be angled radially inward relative an outer diameter of the cutter 2800 (and/or the elongate body of the catheter). The outer side wall of the cutter edge 2810 forms an angle β relative to a sidewall of the elongate body of the catheter 2800 along a longitudinal direction. The angle β can be between 2 to 12 degrees in some embodiments. For example, the angle β can be 5 degrees. The distal tip of the serrated annular cutting edge 2810 can extend radially inward relative an outer diameter of the elongate body by 2 degrees to 12 degrees. The angle β advantageously ensures that the cutting edge 2810 does not cut through the distal tip or nosecone of the catheter. The serrated annular cutting edge 2810 can be angled radially and converged to a center axis of the cutter 2800 with a converge angle between 4 degrees and 20 degrees. For example, the converge angle can be 10 degrees in some embodiments as shown in FIG. 28E.

FIGS. 29A-29E illustrate a cutter 2900 including a serrated annular cutting edge 2910 with teeth 2912 and a recessed bowl 2914. The atherectomy cutter 2900 can be similar to the cutter 2800 except that the cutter can include five grinding segments 2918 rather than seven. Further, each of the segments 2918 can be longer, e.g., extend a greater distance along the circumference of the cutting edge 2910, than in cutter 2800.

FIGS. 30A-30E illustrate a cutter 3000 including a serrated annular cutting edge 3010 with teeth 3012 and a recessed bowl 3014. The cutter 3000 can be similar to cutters 2800 and 2900 except that the cutter can include ten grinding segments 3018. The grinding segments 3018 can form a substantially half-circle shape.

FIGS. 31A-31E illustrate a cutter 3100. The cutter 3100 can be similar to cutter 3000 except that the grinding segments 3118 can be further closer to one another, thereby making the teeth 3112 shorter. For example, the cutting edge of each tooth 3112 of cutter 3100 can be approximately 0.1-0.3, such as approximately 0.25, of the length of cutting edge of each grinding segment 3118. In contrast, the cutting edge of each tooth 3012 can be approximately 0.4-0.6, such as 0.5 of the length of the cutting edge of each grinding segment 3018. In some embodiments, the cutter 3100 can also be smaller in size overall (e.g., be configured to sit within a 7 French catheter) than the cutter 3000 (which can be configured, for example, to sit within an 8 French catheter).

The cutters described herein can be used, for example, for above the knee atherectomy procedures. In such embodiments, the cutter can be designed to fit in an 8 French catheter and thus can have a diameter, for example, of between 0.07 inches and 0.9 inches, such as approximately 0.077 inches. The cutters described herein can also be used, for example, for below the knee atherectomy procedures. In such embodiments, the cutter can be designed to fit in a 7 French catheter and can have a diameter, for example, of between 0.05 inches and 0.07 inches, such as approximately 0.065 inches. The recessed bowl in the cutters described herein can advantageously help collect and push cut tissue or plaque into the collection chamber in the nosecone of the atherectomy device.

The cutters described can be useful for gripping on to and breaking apart calcified plaque deposits found within the arteries as well as softer forms of plaque that may be encountered. Because calcified plaque is much harder than its softer plaque counterparts, repeated use of the cutter for breakoff and clearing calcified plaque can easily lead to dull cutting edges that are less proficient at grabbing onto and breaking off calcified plaque during subsequent use. Thus, in some examples of the serrated cutter, the cutting edge or even the entire cutter region, including the cutting edge and the bowl, may be coated with or dipped in a hardening material. Suitable hardening coatings may include carbon composites such as tungsten carbide, graphene, and so forth. While the cutters described herein are shown with specific features, it is conceivable that different features from the different cutters described may be combined to form cutters having feature combinations that have not been specifically described herein.

In some embodiments, the cutters serrated cutters described herein can be configured to be interchangeable with one another and/or with non-serrated cutter so as to allow the operator to vary the aggressiveness of the cutter during use.

It should be understood that any feature of one embodiment of a cutter described herein can be added, removed, and/or combined with other embodiments.

Figure 13A:
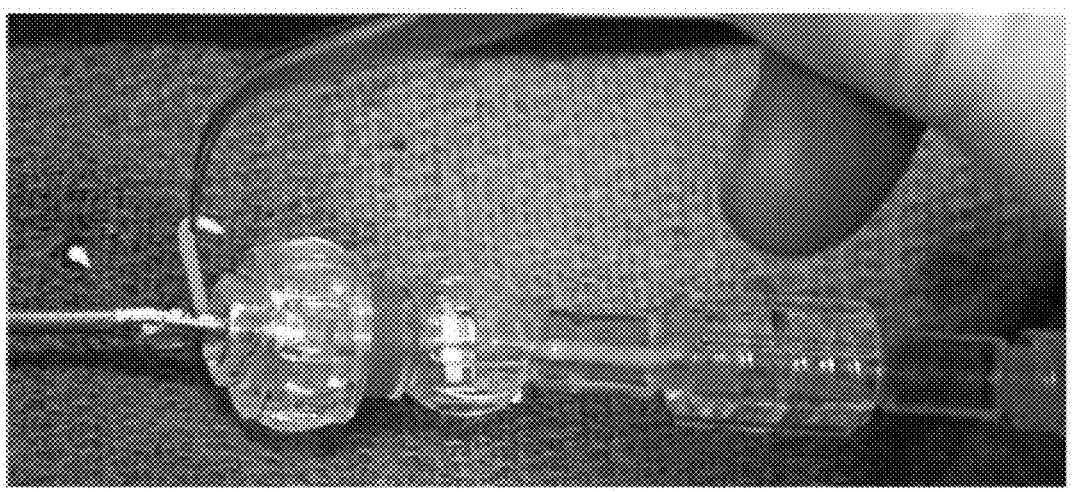
FIG. 13A shows the removal of a single, long strip of material cut from the tissue by an atherectomy catheter as described herein.
Figure 13B:
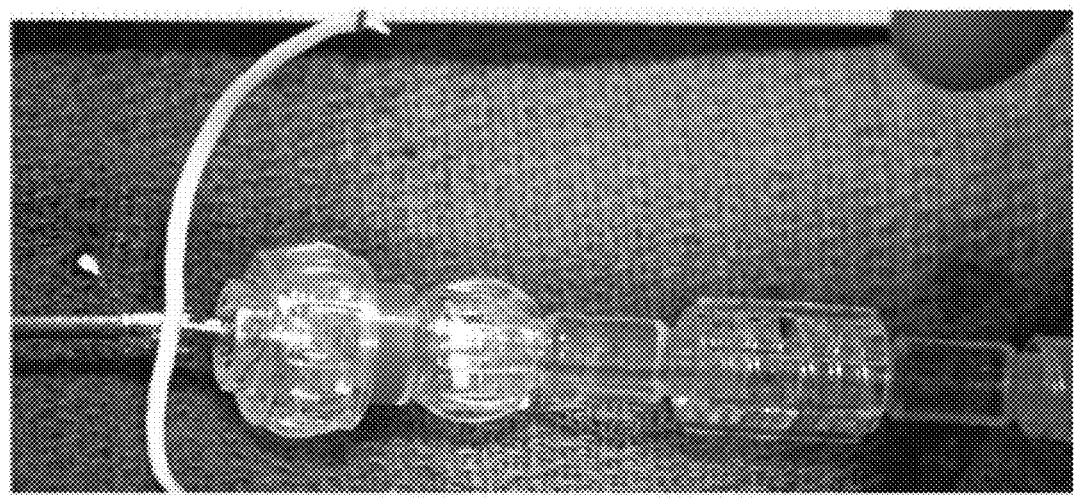
FIGS. 13B and 13C show the length of tissue removed.
Figure 13C:
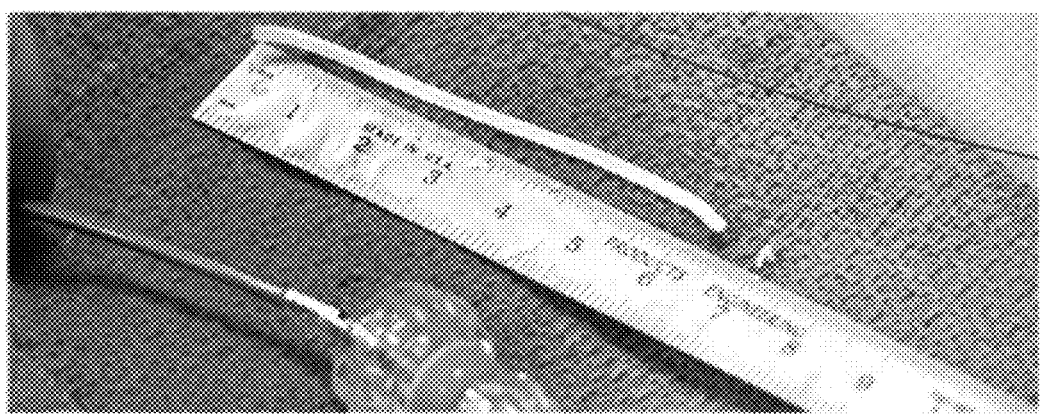

Advantageously, the atherectomy catheters described herein can be used to remove strips of tissue and/or to remove hard or calcified tissue. FIG. 13A shows the removal of a single, long strip of material cut from the tissue by an atherectomy catheter as described herein. FIGS. 13B and 13C show the length of tissue (weighting 70.4 mg) removed.

The atherectomy catheters described herein may additionally include any of the features described in the following co-pending applications: PCT Application No. PCT/US2013/031901, entitled "ATHERECTOMY CATHERES WITH IMAGING," and filed Mar. 15, 2013, and PCT Application No. PCT/US2013/032494, entitled "BALLOON ATHERECTOMY CATHERS WITH IMAGING" and filed Mar. 15, 2013, and PCT Application No. PCT/US17/22780, entitled "ATHERECTOMY CATHETERS AND OCCLUSION CROSSING DEVICES" and filed Mar. 16, 2017, all of which are incorporated by reference herein in their entireties.

The catheters described herein can be driven using a drive assembly. Exemplary drive assemblies are described in co-pending Patent Applications: PCT Application No. PCT/US13/32089, entitled "ATHERECTOMY CATHETER DRIVE ASSEMBLIES," filed Mar. 15, 2013, and U.S. patent application Ser. No. 13/654,357, titled "ATHERECTOMY CATHETERS AND NON-CONTACT ACTUATION MECHANISM FOR CATHETERS," filed Oct. 17, 2012, both of which are incorporated by reference in their entireties.

Also described herein are support arms for maintaining and positioning a medical device component, such as a controller or drive assembly of an atherectomy catheter, during related medical procedures. In particular, the support arm is able to attach easily to any rail in close proximity to the procedure table and to take multiple positions for providing convenient access to a catheter (e.g., atherectomy catheter) control unit.

Figure 32A:
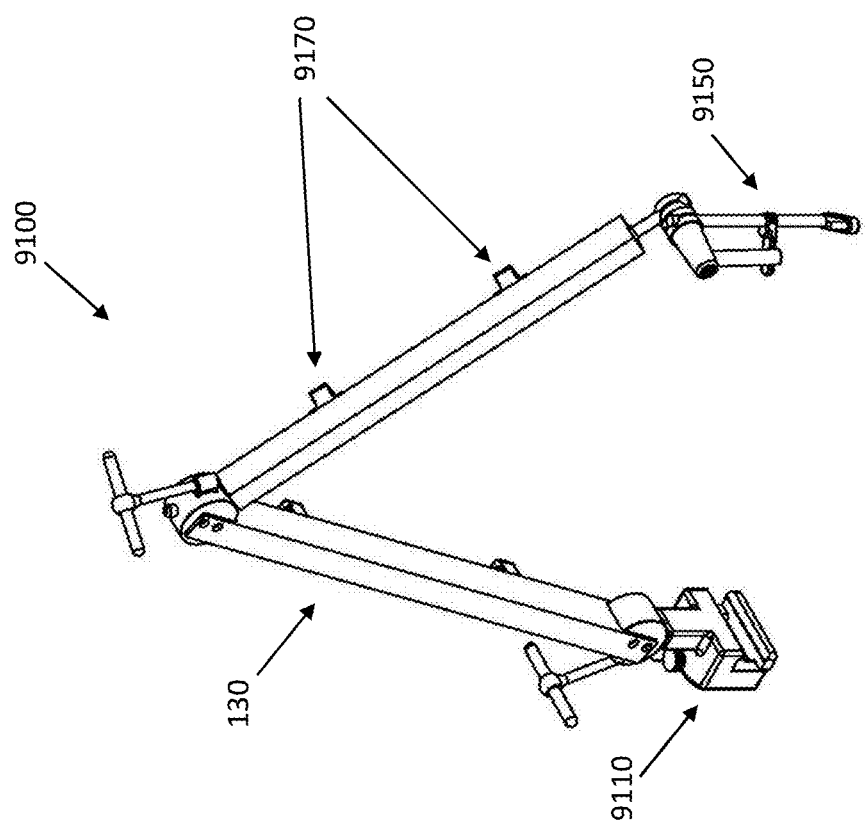
FIG. 32A is a perspective view of a support arm assembly.
Figure 32C:
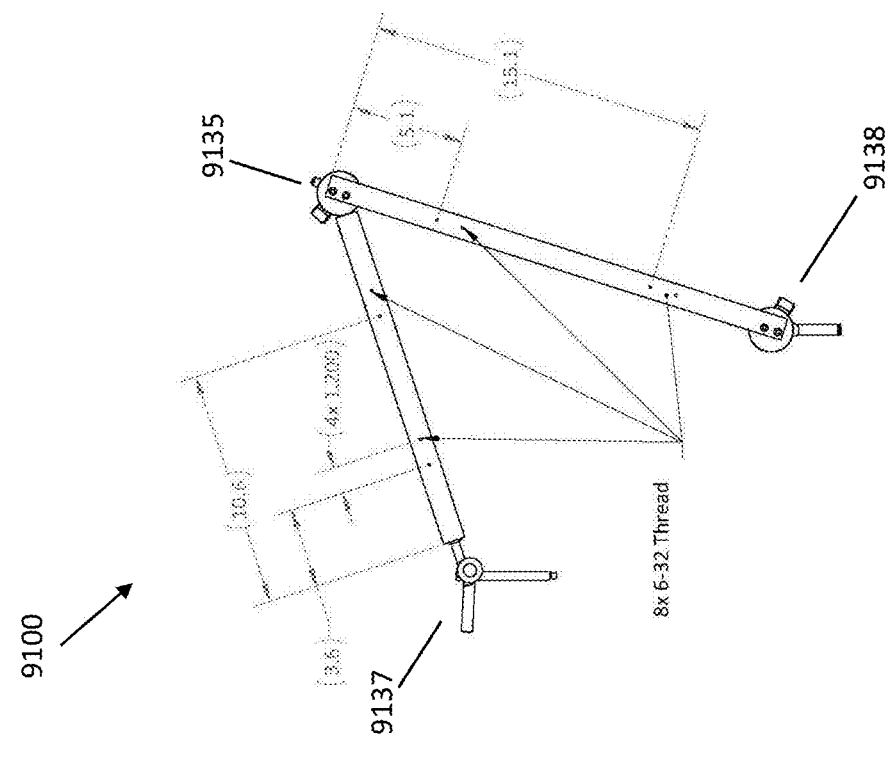
FIG. 32C is a top view of the support arm portion of the support arm assembly of FIG. 32A.
Figure 32B:
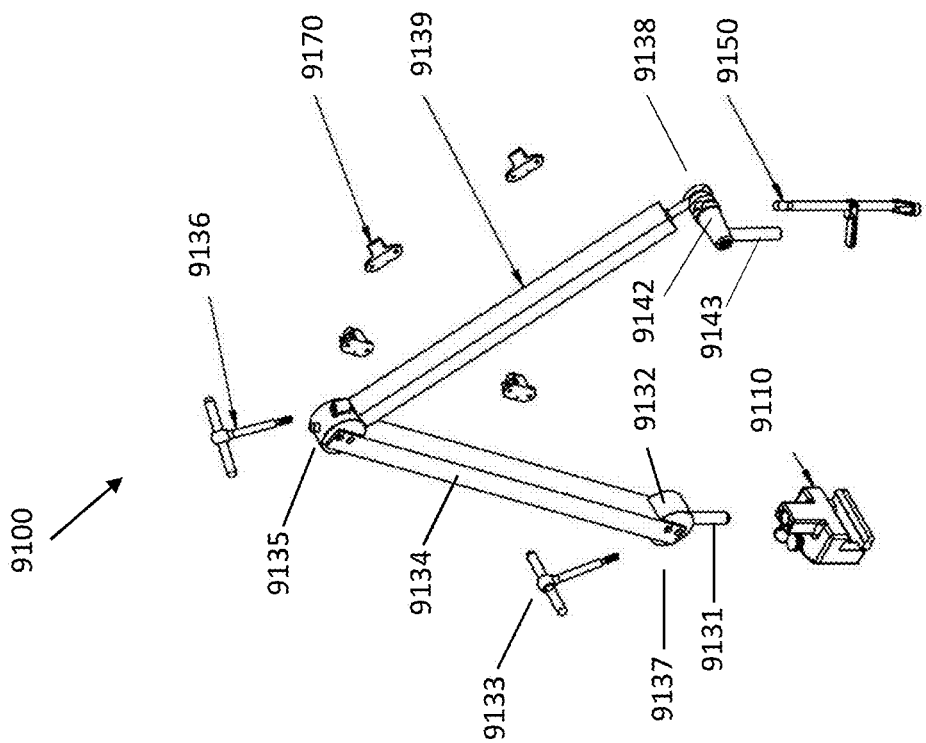
FIG. 32B is an exploded view of the support arm assembly of FIG. 32A.

An exemplary support arm assembly 9100 is shown in FIGS. 32A-32C. In general, the support arm assembly 9100 can include a clamp 9110, a support arm 9130 and a device mount 9150. In some embodiments, the assembly 9100 can also include a cable retainer 9170. The support arm 9130 has two ends. The clamp 9110 couples to one end of the support arm 9130, and the device mount 9150 couples to the other end.

The support arm 9130 may be releasably attached to clamp 9110. Support arm 9130 may swivel up to 9360 degrees with respect to clamp 9110. This allows the support arm 9130 to be easily positioned anywhere along the length of an operating or procedure table. The support arm 9130 may also be adjusted so that it can reach the width of any operating or procedure table. In use, the free end of the support arm 9130 is coupled to the device mount 9150. The free end of the support arm 9130 can allow for rotational freedom of the coupled device mount 9150 such that the device component being held by the device mount 9150 may be arranged in the most optimal position during a procedure.

As shown in FIG. 32B, the support arm 9130 can include two segments 9134 and 9139 joined by a segment joint 9135. While FIG. 32B shows segments 9134 and 9139 as being cuboid in shape, the segments can be any reasonable geometric shape, such as hexagonal or triangular prism, a cylindrical rod, and so forth. As shown in FIGS. 32A-32C, the segment joint 9135 provides a hinged connection between segment 9134 and segment 9139. The segment joint 9135, as shown, provides freedom to move along one axis. In other examples, the segment joint may be a joint that provides greater degrees of freedom such that one segment is able to rotate out of axis relative to the second segment.

Each segment 9134 and 9139 can include segment free ends 9137 and 9138. At segment free end 9137 is a clamp arm joint 9132. A clamp arm joint 9132 couples with the segment free end 9137 of segment 9134. Disposed on the clamp arm joint 9132 is a clamp coupling post 9131 for coupling to clamp 9110. In the figures, the clamp arm joint 9132 that joins clamp coupling post 9131 with segment 9134 is a hinged connection that allows for movement of the segment 9134 relative to the clamp coupling post 9131 in a fixed axis of rotation. In other examples, the coupling joint that connects one segment to the clamp coupling post may be a rotatable joint that is able to have multiple degrees of rotational freedom.

Disposed at the segment free end 9138 can be a device mount coupler 9142 that couples the segment 9139 to the device mount 9150. The device mount coupler 9142 shown in FIG. 32B is configured to rotate along one axis, but in other examples, the device mount coupler 9142 may rotate along multiple axes. The device mount coupler 9142 also includes a device mount adjustor 9143. The device mount adjustor 9143 is able to loosen or tighten the device mount coupler 9142 for positioning the device mount 9150 and maintaining the device mount 9150 once a desired position has been found.

Figure 33B:
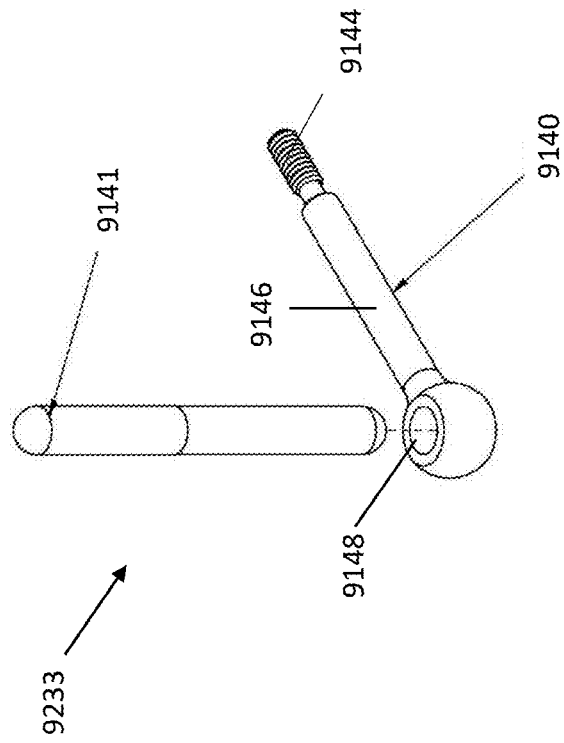
FIG. 33B is an exploded view of the adjustment knob screw of FIG. 33A.
Figure 33A:
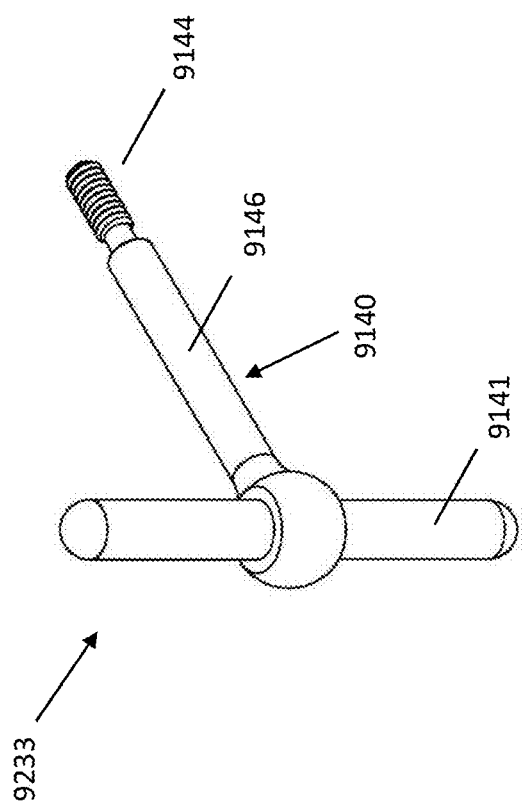
FIG. 33A is a perspective of an adjustment knob screw.
Figure 34B:
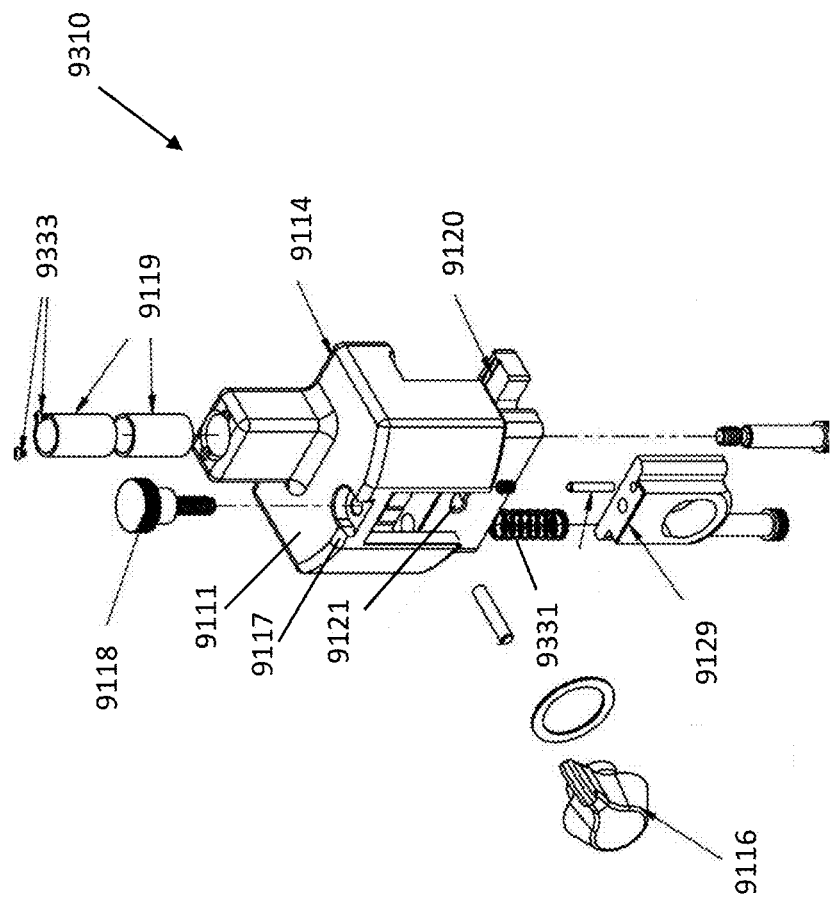
FIG. 34B is an exploded view of the side rail clamp of FIG. 34A.
Figure 34A:
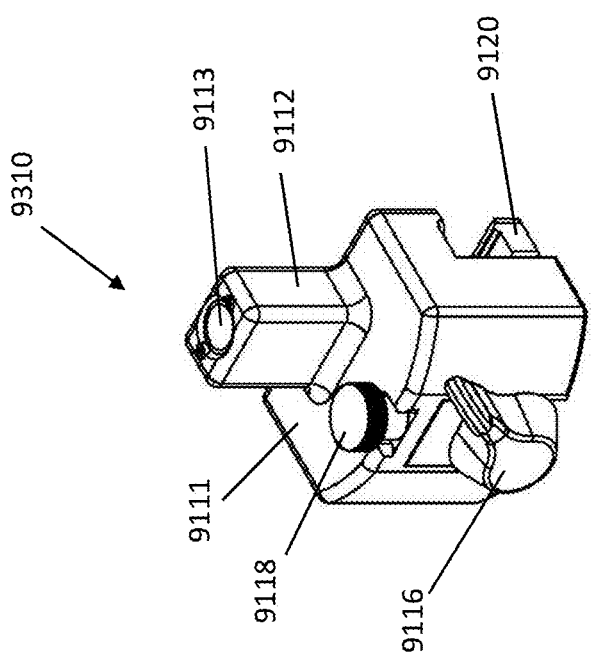
FIG. 34A is a perspective view of a side rail clamp.
Figure 34D:
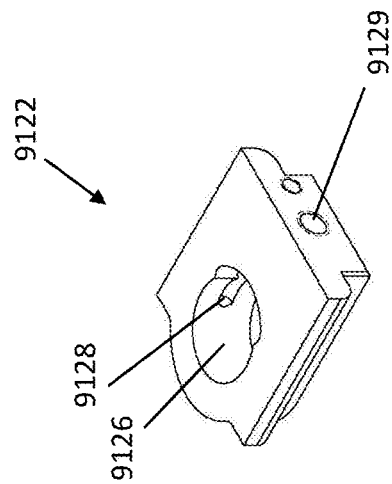
FIG. 34D is a perspective view of a side cam level adjustor of the side rail clamp of FIG. 34A.
Figure 34C:
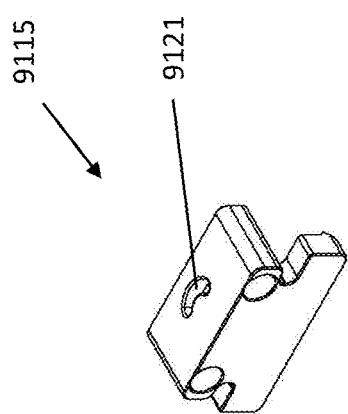
FIG. 34C is a perspective view of the bottom jaw of the side rail clamp of FIG. 34A.
Figure 34E:
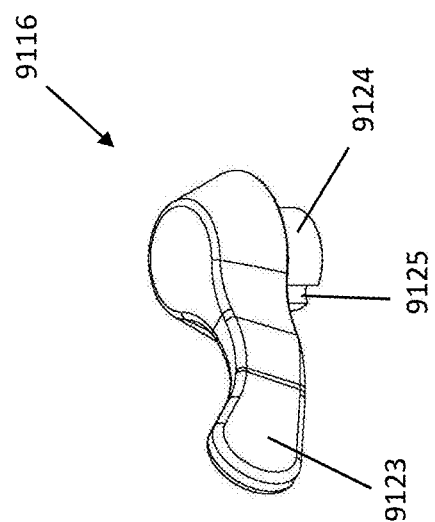
FIG. 34E is a perspective view of the side cam lever of the side rail clamp of FIG. 34A.

The support arm 9130 can also include friction adjustors 9133 and 9136. In some embodiments, the friction adjustors 9133 and 9136 can be identical. An exemplary embodiment of a friction adjustor 9233 (which can be used as a friction adjustor 9133 and/or 9136) is shown in FIGS. 33A-33B. The friction adjustor 9233 can each include an adjustment knob screw 9140 and an adjustment knob handle 9141. The adjustment knob handle 9141 is shown as having a rod-like structure of approximately 3.5 inches in length, but in other examples, the adjustment knob handle may be of either shorter or longer length and may be of other suitable shape such as a flat piece of material or a rod having various cross-sectional dimensions. The adjustment knob screw 9140 includes a screw portion 9144 at one end and a handle coupler 9145 at its opposing end joined by an adjustment knob screw stem 9146. The handle coupler 9145 as shown further includes a handle coupling aperture 9148 into which the adjustment knob handle 9141 may be inserted. While the figures show the adjustment knob handle 9141 as having a circular cross-section and the handle coupler aperture 9148 having a corresponding circular opening, it is possible for the adjustment knob handle to have any cross-sectional dimension and for the handle coupling aperture to have a corresponding aperture opening shape to accommodate the adjustment knob handle. In use, once the operator has positioned the support arm 9130 into a desired position, the operator may turn the adjustment knob handle 9141 such that the screw portion 9144 bears down on either the segment joint 9135 or the clamp arm joint 9132, locking the segments into a fixed position. The adjustment knob handle 9141 may be turned to loosen and reduce the amount of force that the screw portion 9144 of the adjustment knob screw 9140 applies to either the segment joint 9135 or the clamp arm joint 9132.

While FIGS. 32A-32C show the support arm segments as having approximately equal length, the segments may of differing length. In other examples, the support arm may include more than two segments or include many segments such that the medical device component may be more easily maneuvered or maneuvered with greater precision. In yet other examples, the support arm segments may have telescoping qualities such that each segment may be lengthened or shortened depending on the position desired.

Moreover, while FIGS. 32A-32C show a knob type adjustment for adjusting and maintaining the support arm segments, other types of adjustment units may also be used. These may include a flip type locking mechanism, a ratcheting system, or other type locking mechanism known in the art that is integrated into the body of the coupled segments.

Referring still to FIGS. 32A-32C, the clamp 9110 can be configured to couple the assembly 9100 to a bed rail or other solid support. The clamp 9110 can thus be configured to provide enough support and stability to hold both the support arm 9130 and a medical component coupled to the device mount 9150 steady during a procedure. As such, the clamp 9110 can be designed so as to withstand the weight of the support arm 9130, the device mount 9150, and the medical device within the mount 9150 even as the arm 9130 is maneuvered around. In some embodiments, the clamp 9110 securely attaches to a rail or other solid support when the medical device within the mount 9150 is greater than 5 pounds, greater than 10 pounds, or greater than 15 pounds, such as up to approximately 20 pounds. The clamp 9110 can be easy to adjust such that, with a single motion, a user is able to attach or release the clamp 9110 from a rail or a solid surface or support. In some embodiments, the clamp 9110 has an adjustable diameter of between 0.5 inch and 3 inches.

As shown in FIGS. 32A and 32B, the clamp 9110 can be coupled to the support arm 9130 through the clamp coupling post 9131. An exemplary embodiment of a clamp 9310 (which can be used as claim 9110) is shown in FIGS. 34A-34E. The clamp 9310 includes a clamp top jaw 9114, a clamp top cover 9111, a clamp bottom jaw 9120, and a clamp lever 9116. The jaws 9114, 9120 can be configured to move towards one another to clamp a device therebetween. The clamp top cover 9111 can include a support arm coupler 9112 and a cutout region 9117, both of which are disposed on the top surface of the clamp top cover 9111. The support arm coupler 9112 can further include a support arm coupling aperture 9113 that may be mated with the clamp coupling post 9131. The support arm coupler 9112 may also include sleeve bearings 9119 to provide better rotational movement by reducing friction between the clamp coupling post 9131 and the support arm coupler 9112. There may also be screws 9333 for retaining the sleeve bearings 9119 in place. The cutout region 9117 can be positioned opposite the support arm coupler 9112. The top piece cutout region 9117 can function to retain a course adjustment knob 9118.

In use, the distance between the clamp upper jaw 9114 and the clamp lower jaw 9120 may be adjusted to retain various sizes of rail or surface. Distances between the upper jaw 9114 and the lower jaw 9120 may range from 0.5-3 inches. In some embodiments, the operator may turn the course adjustment knob 9118 when it is coupled to the clamp 9110 to adjust the initial distance between the top jaw 9114 and the bottom jaw 9120.

In some embodiments, a lever 9116 can be configured to allow for vertical movement of the clamp lower jaw 9120. The lever 9116 includes a lever handle 9123 and a lever stem 9124. By toggling the lever handle 9123 from one side to another and back, the operator may adjust the distance between the clamp upper jaw 9114 and the clamp lower jaw 9120. The lever 9116 is in a shape that allows easy adjustment of the distance between the upper and lower jaws 9114, 9120 of the clamp 9110. The lever 9116 includes a lever stem 9124 that mates with a side cam lever adjustor 9122. The lever 9116 also includes a lever stem cutout 9125 that may be used to retain a post or dowel 9127 that allows for coupling to the side cam lever adjustor 9122. The side cam lever adjustor 9122 includes a side cam lever adjustor aperture 9126 that couples to lever stem 9124. Furthermore the side cam lever adjustor aperture 9126 may further include a side cam lever adjustor aperture cutout 9128 that serves to more precisely mate with the lever stem cutout 9125 of lever 9116 through the dowel 9127 such that when the lever handle 9123 of lever 9116 is moved from one side to the other, the dowel 9127 is moved within the side cam lever adjustor aperture cutout 9128 and through the clamp bottom piece aperture 9121 to move the bottom jaw piece 9115 up and down. The side cam lever adjustor 9122 may also include side cam lever adjustor coupling apertures 9129 for coupling to the upper jaw 9114 and the lower jaw 9120 pieces. The joining of the lever 9116 with the bottom jaw piece 9115 through the side cam lever adjustor 9122 may also include washers for cushioning the movement of the lever with respect to the side cam lever adjustor. The claim 9310 may also include a spring 9331 to provide a more even force distribution against the bottom jaw piece 9115 when actuated by the side cam lever adjustor 9122. The lever 9116, side cam lever adjustor 9122, and clamp lower jaw 9120 ensemble may further include other dowels, screws, and pins to provide smooth actuation of the clamp lower jaw 9120 when the lever 9116 is adjusted.

An alternative clamp design 9610 (that could be used as clamp 9110) is shown in FIGS. 37A-37B. The clamp 9610 functions in essentially the same manner as clamp 9210 for grabbing onto a rail or a surface. The primary difference between the clamps 9610 and 9210 is that in clamp 9610, a lever 9616 that actuates a lower jaw 9620 (to bring it closer to the upper jaw 9614) can be flipped from an up and down direction, while clamp 9210 actuates the clamp with a side to side motion of its lever.

Referring back to FIGS. 32A-32C, cable retainers 9170 (or clasps) can be used to maintain cables used for powering the medical device such that the cables do not become entangled. The cable retainers 9170 can also keep the cables away from the patient and/or prevent the cables from needlessly obstructing the medical personnel's view of the patient or treatment site during a procedure. As can be seen from FIGS. 32A and 32B, the series of cable management retainers 9170 may be disposed along the length of segments 9134 and 9139. The cable management retainers 9170 can be constructed to comfortably retain cables associated with the use of the medical device (e.g. power cables, signal cables, wires, and so forth). The cable management retainers 9170 can keep necessary cables associated with the medical device component clear of where healthcare professionals may be working.

An exemplary cable management retainers 9470 (which can be used as retainer 9170) is shown in FIGS. 35A-35C. The cable management retainer 9470 includes a cable management top cover 9171 coupled with a cable management bottom piece 9175. The cable management top cover 9171 includes a cable management top coupling channel 9172 that is capable of accepting a pin 9179. The cable management top cover 9171 also includes a cable management torsion spring groove 9173 that is able to mate with a torsion spring 9180. When in place, the torsion spring 9180 allows the cable management top cover 9171 to automatically snap back to a closed position after the cable management top cover 9171 has been flipped to an open position.

This prevents cables or wires from inadvertently slipping out of the cable management retainer 9470 during the medical procedure and interfering with the medical procedure at hand.

The cable management bottom piece 9175 includes at least two cable management bottom channels 9176 such that when the cable management top coupling channel is seated between the two cable management bottom channels 9176 and a pin 9179 is inserted through the each of the channels, the cable management top cover 9171 mates with the cable management bottom piece 9175 and is able to pivot at with respect to the cable management bottom piece 9175. The cable management bottom piece 9175 further includes a cable management bottom lip 9177. The cable management bottom lip 9177 has a slanted outer edge such that when the cable management top cover 9171 is in contact with the cable management bottom piece 9175, the slanted outer edge comes into contact with the shorter side of the tapered edge of the cable management top cover 9171. The cable management top cover 9171 can also be slightly tapered underneath. The advantage of this configuration is that a user can easily catch the longer side of the tapered edge of the cable management top cover 9171 with his finger and easily insert or remove cables of choice, even if wearing gloves. The cable management bottom piece 9175 also includes at least one cable management bottom screw aperture 9178, which allows the cable management clasp 9170 to be coupled to the support arm 9130 or other portion of the support arm assembly 9100.

Referring back to FIGS. 32A-32C, the device mount 9150 can be configured to couple with, and hold steady, a medical device component that is greater than 5 pounds, greater than 10 pounds, or greater than 15 pounds, such as up to 20 pounds. For example, the device mount 9150 can be configured to maintain a catheter drive controller during use of the catheter (e.g., an atherectomy catheter).

Figure 36B:
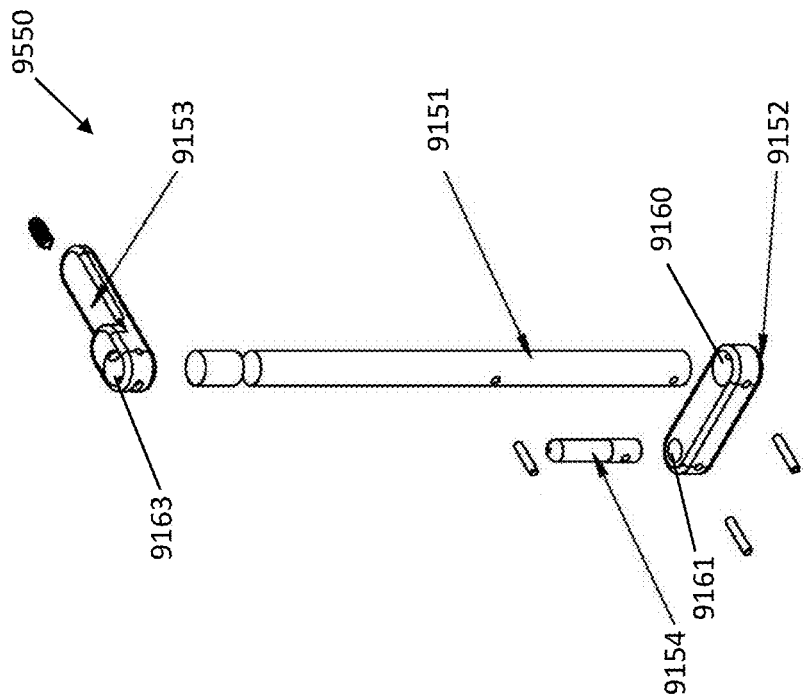
FIG. 36B is an exploded view of the catheter controller mount of FIG. 36A.
Figure 36A:
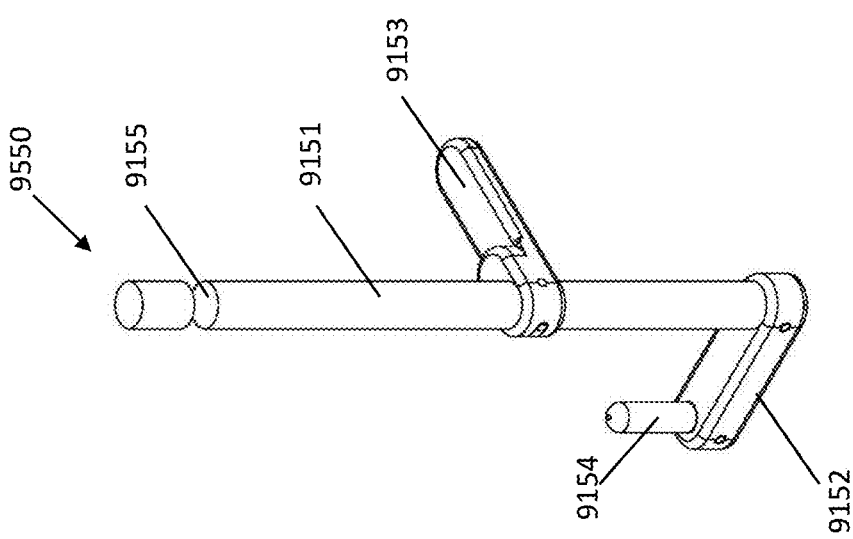
FIG. 36A is a perspective view of a catheter controller mount.

An exemplary device mount 9550 (which can be used as device mount 9150) is shown in FIGS. 36A-36B. The device mount 9550 includes a device mount stem 9151. At one end of the device mount stem 9151, a device mount base 9152 is attached. The device mount base 9152 extends perpendicularly away from the device mount stem 9151. Disposed on the end of the device mount base 9152 opposite where it couples to the device mount stem 9151, is a device mount post 9154 that extends in the direction of the device mount stem 9151. The device mount stem 9151 may include coupling pin apertures 9164 for coupling to the device mount base 9152 and the device mount latch 9153.

In the embodiment of the device mount 9550, the device mount base 9152 also includes a device mount base stem aperture 9160 for coupling to the device mount stem 9151 and a device mount base post aperture 9161 that couples to the device mount post 9154. The device mount post 9154 is configured to couple with the device component being supported so as to prevent the device component from detaching form the device mount 9550 during use and inadvertently injuring the patient. The device mount base 9152 may also include coupling pin apertures 9164 that may be tightened or loosened for either coupling to the device mount stem 9151 or the device mount post 9154.

The device mount 9550 also includes a device mount latch 9153 at an intermediate position along the device mount stem 9151. The device mount latch includes a device mount latch stem aperture 9162 for coupling to the device mount stem 9151. The device mount latch 9153 may be adjusted along the device mount stem 9151 such that when a device has been coupled to the device mount post 9154, the device mount latch 9153 may be lowered to contact the top surface of the device component, where then the device mount post 9154 may be tightened locking its position along the length of device mount stem 9151 for steadying the device component within device mount 9550. In some instances, the device component having a corresponding cavity for accepting the device mount post 9154 may be swiveled to obtain the best viewing angle. Once the desired orientation of the device component has been obtained, the device mount latch may be used to maintain the orientation of the device component during use. While not shown the device mount latch may include a cushioning layer on its surfaces that come into contact with the device component.

The end of the device mount stem 9151 that is configured to couple to the device mount adjustor 9143 of the support arm 9130 includes a device mount stem notch 9155. The device mount stem notch 9155 encompasses the entire circumference of the device mount stem 9151. The device mount stem notch 9155 allows the device mount 9150 to be snapped into, and held within, the device mount coupler 9142. The device mount coupler 9142 may have include internal mechanisms (not shown) that allow it to grip onto the device mount stem notch 9155 of the device mount 9150. The device mount 9550, when coupled to the support arm 9130, can rotate along at least one axis of rotation. The device mount 9150 is able to rotate about the long axis of the device mount stem 9151. In other examples, the device mount stem 9151 may be coupled to the device mount coupler 9142 by any suitable means known in the art including but not limited to hooks, clasps, clips, and so forth.

Figure 36C:
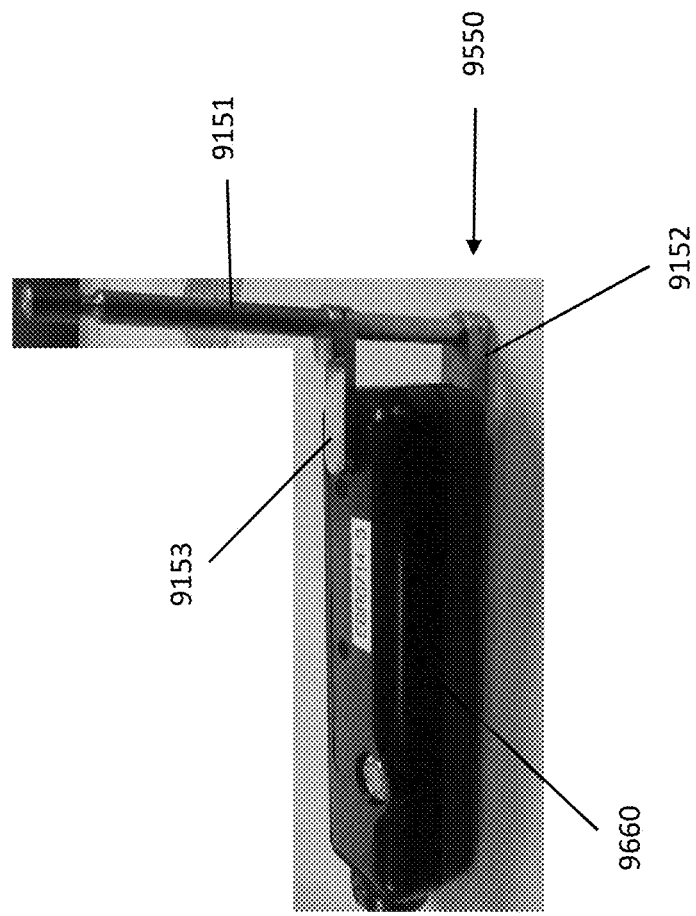
FIG. 36C shows the catheter controller mount of FIG. 36A coupled to a catheter controller.

FIG. 36C shows the device mount 9550 attached to a controller 9666, e.g., a controller for an atherectomy catheter. The device mount 9154 can mate with a slot in the controller 9666, and the controller 9666 can rest on the base 9152. The device mount latch 9153 can help maintain the controller 9666 within the device mount 9550. The device mount post 9154 height may range anywhere from approximately 1 cm to 3 cm. The device mount post 9154 advantageously does not interfere with the circuitry, layout, or function of the device component. The device mount 9550 is designed such that their weight when coupled to the device component provides reasonable counter weight to the support arm 9130 and thus does not over-stress the coupling between the clamp 9110 and its supporting element (e.g. bed rail). In some other examples, the device mount may include some other type of coupling mechanism. For example, the device mount base may include one or more protrusions or locking mechanism that are able to mate with features on the device component. The device mount base may include adjustable appendages that can grasp onto the device component or snap onto the device component. The device mount may include female couplers that are able to make with corresponding male couplers on the device component or vice versa.

Figure 38:
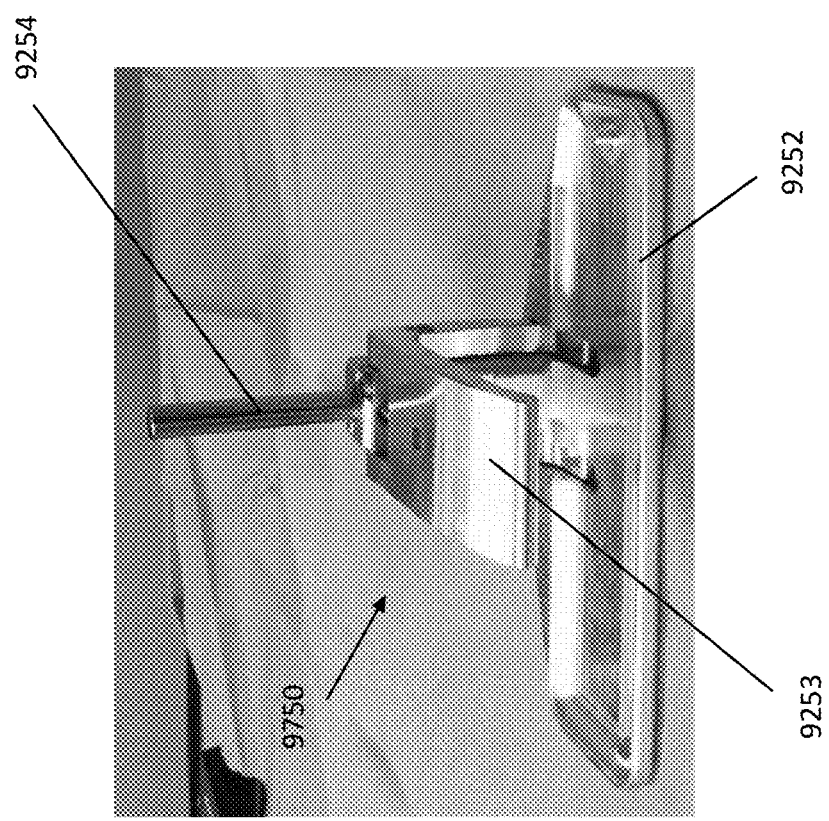
FIG. 38 shows another embodiment of a catheter controller mount.

FIG. 38 shows another embodiment of a device mount 9750. Instead of a device mount latch as that of device mount 9550, the device mount 9750 is in a "C" configuration, where the top portion includes a device mount flap 9253 and the bottom portion has a device mount support base 9252 that is able to support the dimensions of the device component instead of coupling to the device component through a single attachment point. The device mount flap 9253 may be adjustable in distance with respect to the device mount support base 9252. The device mount flap 9253 may be hingedly attached to the device mount support base 9252 such that it is able to hold the device component securely during use. It may also be possible for the device mount flap 9253 and the device mount support base 9252 to rotate about the longitudinal axis of a device mount post 9254.

Further, FIGS. 39A-39B show another embodiment of a device mount 9850. The device mount 9850 includes a base against which the controller 9866 sits. A device mount post 9854 can be configured to be rotated or screwed into a mating hole in the controller 9866 to hold it thereto.

Figure 40B:
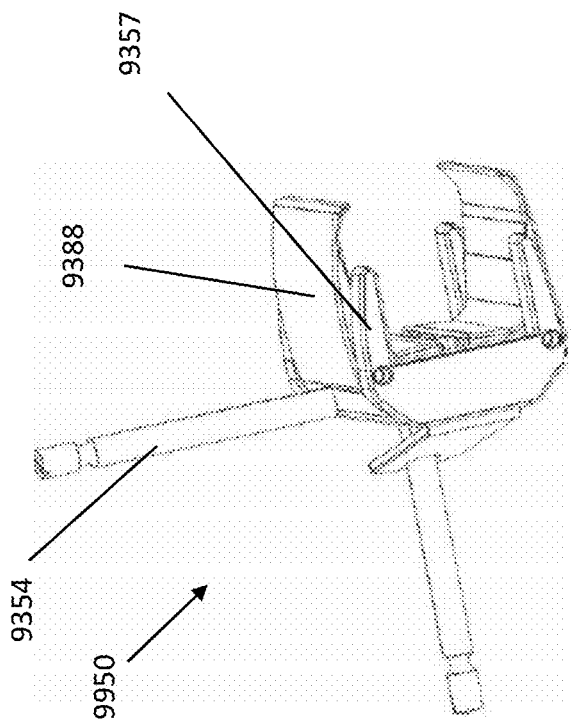
FIGS. 40A-40B show another embodiment of a catheter controller mount.
Figure 40A:
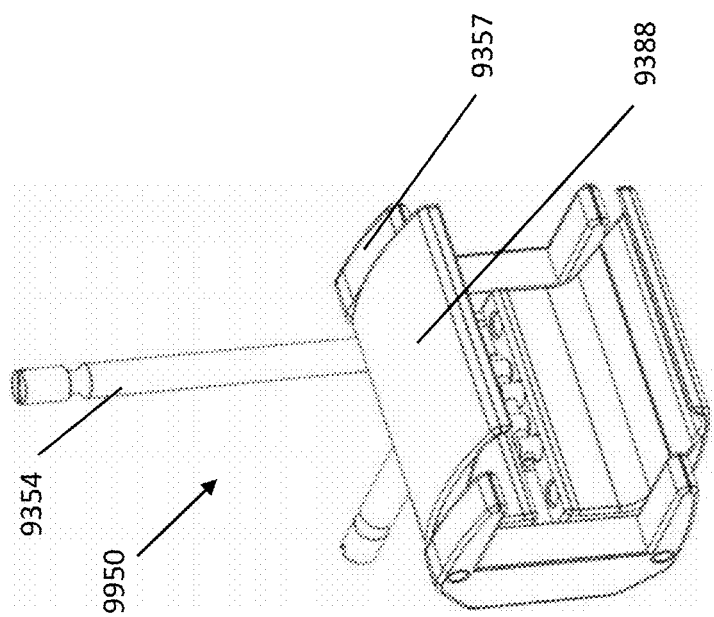
Figure 40C:
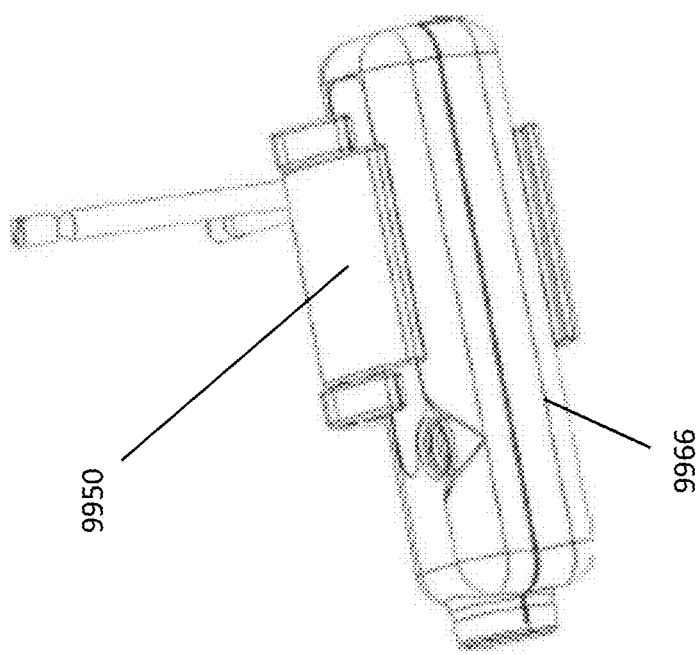
FIG. 40C shows the catheter controller mount of FIG. 40A coupled to a catheter controller.

FIGS. 40A-40C show yet another embodiment of a device mount 9950. FIGS. 40A-40B shows a device mount 9350 that is unattached, and FIG. 40C shows the device mount 9250 securely attached to a controller 9966. Similar to the device mount 9750, device mount 9950 has a "C"-shaped configuration with a device mount post 9354 for coupling to the support arm. The device mount 9350 has an outer C holder 9357 and an inner C clasp 9358. The inner C clasp 9358 may hingedly hold onto the device component during use. The distance between the two ends of the C clasp 9358 may also be adjusted to accommodate different device component heights.

Another exemplary device mount 91050 is shown in FIGS. 41A-41B. The device mount 91050 can be attached to a pivotable portion 91092 of a support arm 91000. Further, the device mount 91050 can include a base 91052 configured to sit horizontal such that the controller 91066 can rest thereon. Device mount posts 91054*a,b* can be configured to mate with corresponding apertures on the controller 91066 to hold it in place.

The device mounts, support arm assemblies, and clamping mechanisms described herein can all be designed to be able to balance the weight of the device component being held such that the clamp is able to maintain secure contact with the rail or surface onto which it is clamped.

The devices described herein may include additional features not shown in the figures. For example, the device mount flap and/or the device mount support base may include cushioning material on the surfaces that would contact the device component. In other instances, the device mount portions that would contact the device component may include materials having greater friction so that the device component would not easily slip from the device mount while being maneuvered. Device mounts described herein may also include springs known in the art of clips and clamps that aid with maintaining pressure on the device component during use.

As noted above, the devices and techniques described herein can be used with OCT imaging. Exemplary imaging systems are described in co-pending applications: U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; International Patent Application titled "OPTICAL COHERENCE TOMOGRAPHY WITH GRADED INDEX FIBER FOR BIOLOGICAL IMAGING," filed Mar. 15, 2013, Publication No. WO-2013-172972, all of which are incorporated by reference in their entireties.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the examples described herein, but only by the plain meaning of the claim terms employed.

What is claimed is:

1. An atherectomy catheter device, the device comprising:
   an elongate body; and
   a drive shaft extending proximally to distally within the elongate body; and
   a cutter attached to the driveshaft, the cutter including:
   a serrated annular cutting edge formed on a distal edge of the cutter, the serrated annular cutting edge including a plurality of convex portions, each of the plurality of portions having a convex shape with no sharp points along a distal-most circumference of the cutting edge,
   a recessed bowl extending radially inwards from the annular cutting edge to a center of the cutter, and
   a plurality of grinding segments positioned within the recessed bowl, each of the plurality of grinding segments comprising an inner edge that extends substantially straight from the serrated annular cutting edge to a center of the cutter, wherein each of the plurality of grinding segments is configured to break calcified and hard fibrous disease tissue in an artery.

2. The atherectomy catheter of claim 1, wherein each of the plurality of grinding segments forms one of the plurality of convex portions on the serrated annular cutting edge.

3. The atherectomy catheter of claim 1, wherein the cutter comprises at least 4 grinding segments.

4. The atherectomy catheter of claim 1, wherein each of the plurality of grinding segments is a flat facet.

5. The atherectomy catheter of claim 1, wherein each of the plurality of grinding segments is a curved facet.

6. The atherectomy catheter of claim 1, wherein each of the plurality of grinding segments are substantially square, rectangular, or trapezoidal in shape.

7. The atherectomy catheter of claim 1, wherein each of the plurality of grinding segments forms a convex portion of the serrated annular cutting edge.

8. The atherectomy catheter of claim 1, wherein the plurality of grinding segments are disposed symmetrically around a circumference of the recessed bowl.

9. The atherectomy catheter of claim 1, wherein the plurality of grinding segments are disposed asymmetrically around a circumference of the recessed bowl.

10. The atherectomy catheter of claim 1, wherein an outer wall of the serrated annular cutting edge is angled radially inward relative to an outer diameter of the elongate body.

11. The atherectomy catheter of claim 1, wherein the serrated annular cutting edge extends radially inward relative to an outer diameter of the elongate body by 2 degrees to 12 degrees.

12. The atherectomy catheter of claim 1, wherein the serrated annular cutting edge comprises a continuous wavy shape.

13. An atherectomy catheter device, the device comprising:
    an elongate body;
    a drive shaft extending proximally to distally within the elongate body; and
    a cutter attached to the driveshaft, the cutter including:
    a serrated annular cutting edge formed on a distal edge of the cutter, the serrated annular cutting edge including a plurality of convex portions, each of the plurality of portions having a convex shape along a distal-most circumference of the cutting edge, wherein an outer wall of the serrated annular cutting edge is angled radially inward relative to an outer diameter of the elongate body,
- a recessed bowl extending radially inwards from the annular cutting edge to a center of the cutter, and
- a plurality of grinding segments positioned within the recessed bowl, each grinding segment comprising an inner edge that extends substantially straight from the serrated annular cutting edge towards a center of the cutter.

14. The atherectomy catheter of claim 13, wherein each of the plurality of grinding segments extend at least 50% distally to proximally along the recessed bowl.

15. The atherectomy catheter of claim 13, wherein each of the plurality of grinding segments extend at least 70% distally to proximally along the recessed bowl.

16. The atherectomy catheter of claim 13, wherein a proximal end of the recessed bowl comprises a flat circular section.

17. The atherectomy catheter of claim 13, further comprising a plurality of neighboring portions,
- wherein each of the neighboring portions is between two of the grinding segments, and
- further wherein each of the neighboring portions forms a concave portion of the serrated annular cutting edge.

18. The atherectomy catheter of claim 13, wherein the serrated annular cutting edge comprises a continuous wavy shape.

19. The atherectomy catheter of claim 13, wherein the serrated annular cutting edge comprises at least 4 convex portions.

20. An atherectomy catheter device, the device comprising:
- an elongate body;
- a drive shaft extending proximally to distally within the elongate body; and
- a cutter attached to the driveshaft, the cutter including:
    - a serrated annular cutting edge formed on a distal edge of the cutter, the serrated annular cutting edge including a plurality of convex portions, each of the plurality of portions having a convex shape with no sharp points along a distal-most circumference of the cutting edge, wherein an outer wall of the serrated annular cutting edge is angled radially inward relative to an outer diameter of the elongate body,
    - a recessed bowl extending radially inwards from the annular cutting edge to a center of the cutter, and
    - a plurality of grinding segments positioned within the recessed bowl, each grinding segment comprising an inner edge that extends substantially straight from the serrated annular cutting edge to a center of the cutter,
- wherein the center of the cutter comprises a recessed flat section.

* * * * *